US010319478B2

(12) United States Patent
Fuertinger et al.

(10) Patent No.: US 10,319,478 B2
(45) Date of Patent: Jun. 11, 2019

(54) SYSTEM AND METHOD OF MODELING ERYTHROPOIESIS AND ITS MANAGEMENT

(75) Inventors: Doris Helene Fuertinger, Graz (AT); Franz Kappel, Graz (AT); Peter Kotanko, New York, NY (US); Nathan W. Levin, New York, NY (US); Stephan Thijssen, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 310 days.

(21) Appl. No.: 14/343,464

(22) PCT Filed: Sep. 7, 2012

(86) PCT No.: PCT/US2012/054264
§ 371 (c)(1),
(2), (4) Date: Mar. 7, 2014

(87) PCT Pub. No.: WO2013/036836
PCT Pub. Date: Mar. 14, 2013

(65) Prior Publication Data
US 2014/0200181 A1 Jul. 17, 2014

Related U.S. Application Data
(60) Provisional application No. 61/532,290, filed on Sep. 8, 2011.

(51) Int. Cl.
*G16H 50/50* (2018.01)
*G16H 50/20* (2018.01)
*A61K 38/18* (2006.01)
*G16H 50/80* (2018.01)
*G16H 20/17* (2018.01)
*G06F 19/00* (2018.01)

(52) U.S. Cl.
CPC ......... *G16H 50/50* (2018.01); *A61K 38/1816* (2013.01); *G16H 50/20* (2018.01); *G16H 50/80* (2018.01); *G06F 19/704* (2013.01); *G16H 20/17* (2018.01)

(58) Field of Classification Search
None
See application file for complete search history.

(56) References Cited
U.S. PATENT DOCUMENTS

| 8,382,696 B2 | 2/2013 | Beiriger et al. |
| 9,679,111 B2 | 6/2017 | Fuertinger et al. |
| 2002/0095258 A1* | 7/2002 | Agur .................. G06F 19/3481 702/19 |
| 2003/0134795 A1* | 7/2003 | Farrell ............... A61K 38/1816 514/7.7 |
| 2005/0075274 A1* | 4/2005 | Willmann ........... G06F 19/3437 514/1 |
| 2006/0047538 A1* | 3/2006 | Condurso ............. G06F 19/326 705/3 |
| 2006/0089592 A1* | 4/2006 | Kadhiresan ........... A61M 5/142 604/65 |
| 2007/0054331 A1* | 3/2007 | Kirnasovsky ...... G01N 33/5011 435/7.23 |
| 2007/0178167 A1 | 8/2007 | Andrijauskas |

(Continued)

FOREIGN PATENT DOCUMENTS
WO WO 2013/036836 3/2013

OTHER PUBLICATIONS

Fishbane, S. & Nissenson, a R. The new FDA label for erythropoietin treatment: how does it affect hemoglobin target? Kidney international 72, 806-813 (2007).*
Krzyzanski, W., Jusko, W. J., Wacholtz, M. C., Minton, N. & Cheung, W. K. Pharmacokinetic and pharmacodynamic modeling of recombinant human erythropoietin after multiple subcutaneous doses in healthy subjects. European Journal of Pharmaceutical Sciences 26, 295-306 (2005).*
Krzyzanski, W., Perez-Ruixo, J. J. & Vermeulen, A. Basic pharmacodynamic models for agents that alter the lifespan distribution of natural cells. Journal of Pharmacokinetics and Pharmacodynamics 35, 349-377 (2008).*
"Red Blood Cell Indices". from The Gale Encyclopedia of Medicine. (Gale Group, 2002). pp. 2837-2939.*
(Continued)

*Primary Examiner* — Soren Harward
(74) *Attorney, Agent, or Firm* — Hamilton, Brook, Smith & Reynolds, P.C.

(57) ABSTRACT

A method of adjusting a patient's undesired hematocrit and/or hemoglobin concentration to a value within a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, and employing the patient parameters and an initially selected EPO administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, the method includes employing the model with one or more different ESA administration regimens until the model predicts that the patient's hematocrit and/or hemoglobin concentration will be in the desired range at the predetermined time. The method then includes administering ESA to the patient with an ESA administration regimen predicted to adjust the patient's hematocrit and/or hemoglobin concentration to the desired range at the predetermined time. The method can be implemented in a computer system for adjusting a patient's undesired hematocrit and/or hemoglobin concentration to a desired range at a predetermined time with an erythropoiesis stimulating agent (ESA) regimen.

10 Claims, 29 Drawing Sheets

(56) References Cited

U.S. PATENT DOCUMENTS

| | | | |
|---|---|---|---|
| 2009/0171697 A1* | 7/2009 | Glauser | C12Q 1/6883 705/3 |
| 2010/0169063 A1* | 7/2010 | Yudkovitch | A61M 16/0051 703/11 |
| 2011/0004143 A1 | 1/2011 | Beiriger et al. | |
| 2011/0184379 A1* | 7/2011 | Van Antwerp | A61K 38/212 604/503 |
| 2012/0016686 A1* | 1/2012 | Ryan | G06F 19/3456 705/2 |
| 2012/0150141 A1 | 6/2012 | Weibel | |
| 2013/0085772 A1* | 4/2013 | Gaweda | G06F 19/3456 705/2 |
| 2013/0191097 A1* | 7/2013 | Hocum | G06F 19/12 703/11 |
| 2014/0128791 A1 | 5/2014 | Fuertinger et al. | |

OTHER PUBLICATIONS

Ackleh, A.S., et al., "A Finite Difference Approximation For A Coupled System Of Nonlinear Size-Structured Population," *Nonlinear Analysis*, 50:727-748, 2002.

Ackleh, A.S., et al., "A Structured Erythropoiesis Model With Nonlinear Cell Maturation Velocity And Hormone Decay Rate," *Mathematical Biosciences*, 204:21-48 (2006).

Adimy, M., et al., "Modeling Hematopoiesis Mediated By Growth Factors With Applications To Periodic Hematological Diseases," *Bulletin of Mathematical Biology*, 68:2321-2351 (2005).

Alfrey, C. P. and Fishbane, S., "Implications of Neocytolysis for Optimal Management of Anaemia in Chronic Kidney Disease," *Nephron Clinical Practice*, 106:149-156 (2007).

Banks, H.T., et al., "Modelling And Optimal Regulation Of Erythropoiesis Subject To Benzene Intoxication," *Mathematical Biosciences and Engineering*, 1:15-48 (Dec. 20, 2003).

Barosi, G., et al., "Erythropoiesis and Iron Kinetics," *British Journal of Haematology*, 40:3 503-504, Nov. 1978.

Belair, J., et al., "Age-Structured and Two-Delay Models for Erythropoiesis," *Mathematical Biosciences*, 128:317-346 (1995).

Besarab, A., et al., "The Effects of Normal as Compared with Low Hematocrit Values in Patients With Cardiac Disease Who Are Receiving Hemodialysis And Epoetin," *The New England Journal of Medicine*, 339:584-590 (Aug. 27, 1998).

Bratosin, D., et al., "Programmed Cell Death in Mature Erythrocytes: a Model for Investigating Death Effector Pathways Operating in the Absence of Mitochondria," *Cell Death Differentiation*, 8:1143-1156, (2001).

Collins, A. J., et al., "Epoetin Alfa use In Patients With ESRD: An Analysis Of Recent Use Prescribing Patterns And Hemoglobin Outcomes," *American Journal of Kidney Diseases*, 46:481-488 (2005).

Crauste, F., et al., "Mathematical Study of Feedback Control Roles And Relevance In Stress Erythropoiesis," *Journal of Theoretical Biology*, 263(3):303-316(2010).

Crauste, F., et al., "Adding Self-Renewal In Committed Erythroid Progenitors Improves The Biological Relevance Of A Mathematical Model Of Erythropoiesis,"*Journal Of Theoretical Biology*, 250:322-338 (2007).

Demin, I., et al., "A multi-scale model of erythropoiesis," *Journal of Biological Dynamics*, 4(1):59-70 (2010).

Demin, I., et al., "Spatial Distribution Of Cell Populations In The Process Of Erythropoiesis," *IEJPAM*, 1(2):143-161 (2010).

Fisher, J.W., "Erythropoietin: Physiology and Pharmacology Update," *Experimental Biology and Medicine*, 28:1-24 (2003).

Föller, M., et al., "Enhanced Susceptibility To Suicidal Death Of Erythrocytes From Transgenic Mice Overexpressing Erythropoietin ," *American Journal of Physiology—Regulatory, Integrative and Comparative Physiology*, 293:R1127-R1134 (2007).

Föller, M., et al., "Erthrocyte Programmed Cell Death," *IUBMB Life*, 60:661-668 (2008).

Foley, R. N., et al., "Erythropoietin Therapy, Hemoglobin Targets, And Quality Of Life In Healthy Hemodialysis Patients: A Randomized Trial," *Clinical Journal of the American Society of Nephrology*, 4:726-733 (2009).

Fuertinger, D. H.,. *A Model for Erythropoiesis*. PhD thesis, University of Graz, Austria, 2012.

Fuertinger, D. H., et al., "A Model of Erythropoiesis in Adults with Sufficient Iron Availability," *Journal of Mathematical Biology*, 66(6):1209-1240 (2013).

Fuertinger, D.H. and Kappel, F., A Parameter Identification Technique for Structured Population Equations Modeling Erythropoiesis in Dialysis Patients, Proceeding of the World Congress on Engineering and Computer Science 2013, Oct. 23-25, 2013 San Fancisco, CA, vol. 11:940-944.

Goodnough, L.T., et al., "Detection, Evaluation, And Management Of Iron-Restricted Erythropoiesis," *Blood*, 116:4754-4761 (2010).

Kalantar-Zadeh, K., et al., "Time-Dependent Associations Between Iron And Mortality In Hemodialysis Patients," *Journal of American Society of Nephrology*, 16:3070-3080 (2005).

Lang, F., et al., "Erythrocyte Ion Channels In Regulation Of Apoptosis," *Advances in Experimental Medicine and Biology*, 559:211-217 (2004).

Lang, F., et al., "Mechanisms And Significance Of Eryptosis," *Antioxidants & Redox Signaling*, 8:1183-1192, (2006).

Lang, F., et al,. "Eryptosis, a Window to Systemic Disease," *Eryptosis, Cellular Physiology and Biochemistry*, 22:373-380 (2008).

Loria, A., et al .,"Red Cell Life Span in Iron Deficiency Anaemia", *Brit. J. Haemat*, 13:294-302 (1967).

Mahaffy, J.M., et al., "Hematopoietic Model With Moving Boundary Condition And State Dependent Delay: Applications In Erythropoiesis," *Journal of Theoretical Biology*, 190:135-146 (1998).

Mahaffy, J.M., et al., "An Age-Structured Model For Erythropoiesis Following A Phlebotomy. Technical Report CRM-2598," Department of Mathematical Sciences, San Diego State University, San Diego, CA 92182-0314, Feb. 1999.

Myssina, S., et al., "Inhibition Of Erythrocyte Cation Channels By Erythropoietin,"*Journal of American Society of Nephrology*, 14:2750-2757 (2003).

Polenakovic, M. and Sikole, A., "Is Erythropoietin A Survival Factor For Red Blood Cells?," *Journal of American Society of Nephrology*, 7:1178-1182 (1996).

Pollak, V., et al.,"The Importance Of Iron In Long-Term Survival Of Maintenance Hemodialysis Patients Treated With Epoetim-Alfa And Intravenous Iron: Analysis Of 9.5 Years Of Prospectively Collected Data", *BMC Nephrology*, 10(6): 12 pages (2009).

Roeder, I. and Loeffler, M., "A Novel Dynamic Model Of Hematopoietic Stem Cell Organization Based On The Concept Of Within-Tissue Plasticity," *Experimental Hematology*, 30:853-861 (2002).

Roeder., I., "Quantitative Stem Cell Biology: Computational Studies In The Hematopoietic System," *Current Opinion in Hematology*, 13:222-228 (2006).

Schmidt, J. A., et al., "Control of erythroid differentiation: Possible role of the transferrin cycle," *Cell*, 46:41-51 (1986).

Schwartz, A. B., et al., "One year of rHuEPO therapy prolongs RBC survival may stabilize RBC membranes despite natural progression of chronic renal failure to uremia and need for dialysis," *ASAIO Transactions*, 36:M691-M696 (1990).

Stefanelli, M., et al., "Quantitation of Reticuloendothelial Iron Kinetics in Humans," *The American Journal of Physiology*, 247:842-849 (1984).

Udden, M. M., et al., "Decreased Production Of Red Blood Cells In Human Subjects Exposed To Microgravity," *The Journal of Laboratory and Clinical Medicine*, 125:442-449 (1995).

Werre, J. M., et al., "The Red Cell Revisited. Matters Of Life And Death," *Cellular and Molecular Biology*, 50 (2):139-145 (2004).

Wichmann, H.E., et al., "A Mathematical Model Of Erythropoiesis In Mice And Rats. Part 2. Stimulated Erythropoiesis," *Cell and Tissue Kinetics*, 22:31-49 (1989).

Wish, J. B., "Assessing Iron Status: Beyond Scrum Ferritin And Transferrin Saturation," *Clinical Journal of the American Society of Nephrology*, 1:S4-S8 (2006).

(56) References Cited

OTHER PUBLICATIONS

Weighting, D. M. and Andrews, N. C., "Iron Homeostasis and Erythropoiesis," *Current Topics in Developmental Biology*, 82:141-159 (2008).
Zwaal, R. F., et al., "Surface Exposure Of Phosphatidylserine In Pathological Cells," *Cellular and Molecular Life Sciences*, 62:971-988 (2005).
Notification Concerning Transmittal of International Preliminary Report On Patentability for PCT/US2012/054264, "System and Method of Modeling Erythropoiesis and Its Management", dated Mar. 20, 2014.
Bernard, P.J., "International Committee for Standardization in Haematology: Recommended methods for measurement of red-cell and plasma volume," *J Nucl Med*, 21(8):793-800 (1980).
Albert S. N., "Blood Volume Measurement," *Nuclear Medicine In Vitro*, 2 ed., Philadelphia: JB Lippincott Co., (1983).
Babitt, J. L., and Lin, H. Y., "Molecular Mechanisms of Hepcidin Regulation: Implications for the Anemia of CKD," *American Journal of Kidney Diseases*, 55(4):726-741 (Apr. 2010).
Banks, H.T., et al., "A semigroup formulation of a nonlinear size-structured distributed rate population model," *Control and Estimation of Distributed Parameter Systems: Nonlinear Phenomena* (Desch, W., Kappel, F., and Kunisch, K. (eds.), International Series of Numerical Mathematics (ISNM), vol. 118, pp. 1-19, Birkhauser, Basel (1994).
Bernard P. J., "Measurement of red-cell and plasma volumes," *Nouv Rev Fr Hematol*, 36(2):155-157 (1994).
Chan, R.Y., et al., "Regulation of transferrin receptor mrna expression. Distinct regulatory features in erythroid cells," *European Journal of Biochemistry*, 220:683-692 (1994).
Chang C. C., et al., "Changes of red blood cell surface markers in a blood doping model of neocytolysis," *J Investig Med*, 57(5):650-654 (2009).
Crepaldi, C., et al., "Iron management in hemodialysis patients: Optimizing outcomes in Vicenza, Italy," *Hemodialysis International*, 7(3):216-221 (2003).
Crichton, R., "Iron Metabolism," *Molecular Mechanisms to Clinical Consequences*, 3rd ed. New York, Wiley (2009).
Drüeke, T.B., et al. "Normalization of Hemoglobin Level in Patients with Chronic Kidney Disease and Anemia," *The New England Journal of Medicine*,355(20):2071-2084 (2006).
Feagan, C.J., et al., "Erythropoietin with iron supplementation to prevent allogenic blood transfusion in total hip joint arthroplasty," Annals of Internal Medicine, 133:845-854 (2000).
Finch, C.A., "Erythropoiesis, erythropoietin, and iron," *Blood, the Journal of American Society of Hematology*, 60(6):1241-1246 (1982).
Finch, S., et al., "Iron metabolism. Hematopoiesis following phlebotomy. Iron as a limiting factor," *The Journal of Clinical Investigation*, 29:1078-1086 (1950).
Fleming, M. D., "The regulation of hepcidin and its effects on systemic and cellular iron metabolism, Hematology," *J. Amer. Soc. Hematology*, pp. 151-158 (2008).
Fowler, W.M., and Barner, a.P., "Rate of hemoglobin regeneration in blood donors," *J. Amer. Medical Ass.*, 118:421-427 (1942).
Franzone, P.C., et al., "A mathematical model of iron metabolism," *Journal of Mathematical Biology*, 15:173-201 (1982).
Gifford, S.C., et al., "A detailed study of time-dependent changes in human red blood cells: from reticulocyte maturation to erythrocyte senescence," *British Journal of Haematology*, 135:395-404 (2006).
Goodnough L.T., et al., "Detection, evaluation and management of preoperative anaemia in the elective orthopaedic surgical patient: NATA guidelines," *British Journal of Anaesthesia*, 106(1):13-22 (2011).
Goodnough, L.T., "The role of iron in erythropoiesis in the absence and presence of erythropoietin therapy," *Nephrology Dialysis Transplantation*, 17:14-18 (2002).
International Search Report and Written Opinion issued in International Application No. PCT/US2012/054264; Title: System and Method of Modeling Erythropoiesis and its Management, dated Aug. 14, 2013; Date of Completion of Search: Aug. 6, 2013.

Jaspan, D., "Erythropoietic therapy: Cost efficiency and reimbursement," *Amer. J. Health Syst. Pharm.*, 65:19-29 (2007).
Kaufman, J.S., et al., "Subcutaneous Compared with Intravenous Epoetin in Patients Receiving Hemodialysis," *The New England Journal of Medicine*, 339(9):578-583 (1998).
Messana, J.M., "Association of Quarterly Average Achieved Hematocrit with Mortality in Dialysis Patients: A Time-Dependent Comorbidity-Adjusted Model," *American Journal of Kidney Diseases*, 53(3):503-512 (Mar. 2009).
Nadler, S.B., et al., "Prediction of blood volume in normal human adults," *Surgery*, 51:224-232 (1962).
Nemeth E., et al., "Hepcidin, a putative mediator of anemia of inflammation, is a type II acute-phase protein," Blood, 101(7):2461-2463 (2003).
Nooney, G.C., "An erythron-dependent model of iron kinetics," *Biophysical Journal*, 6:601-609 (1965).
Nooney, G.C., "Iron kinetics and erythron development," Biophysical Journal, 5:755-765 (1965).
Parfrey, P.S., "Target Hemoglobin Level for EPO Therapy in CKD," *American Journal of Kidney Diseases*, 47(1):171-173 (2006).
Pfeffer, M.A., et al., "A Trial of Darbepoetin Alfa in Type 2 Diabetes and Chronic Kidney Disease," *The New England Journal of Medicine*, 361(21):2019-2032 (2009).
Ofman, J. et al. "Proposed Coverage Decision Memorandum for the Use of Erythropoiesis Stimulating Agents in Cancer and Related Neoplastic Conditions," Centers for Medicare and Medicaid Services; Administrative File: CAG #000383N; May 14, 2007.
Ponka, P., "Tissue-specific regulation of iron metabolism and heme synthesis: Distinct control mechanisms in erythroid cells," *Blood*, 89:1-25 (1997).
Ponka, P., et al., "The transferrin receptor: role in health and disease," *The International Journal of Biochemistry & Cell Biology*, 31:1111-1137 (1999).
Pottgiesser, T., et al., "Recovery of hemoglobin mass after blood donation, Transfusion," 48:1390-1397 (2008).
Rice, L., "Neocytolysis on descent from altitude: A newly recognized mechanism," *Annals Internal Medicine*, 134:652-656 (2001).
Rice, L., and Alfrey, C.P., "The negative regulation of red cell mass by neocytolysis: Physiologic and pathophysiologic manifestations," *Cellular Physiology and Biochemistry*, 15:245-250 (2005).
Rice, L., et al., "Neocytolysis contributes to the anemia of renal disease," *Amer. J. Kidney Diseases*, 33:59-62 (1999).
Rice, L., et al., "Neocytolysis on descent from altitude: A newly recognized mechanism," Annals Internal Medicine, 134:652-656 (2001).
Schaefer, R.M. and Schaefer, L., "Iron monitoring and supplementation: How do we achieve the best results?," *Nephrology Dialysis Transplantation*, 13:9-12 (1998).
Strippoli, G.F.M., et al., "Hemoglobin Targets for the Anemia of Chronic Kidney Disease: A Meta-analysis of Randomized, Controlled Trials," *Journal of the American Society of Nephrology*, 15:3154-3165 (2004).
Strocchi A., "A Simple Carbon Monoxide Breath Test to Estimate Erythrocyte Turnover," *J. Lab Clin Med*, 120(3):392-399 (1992).
Volkova, N., et al., "Evidence-Based Systematic Literature Review of Hemoglobin/Hematocrit and All-Cause Mortality in Dialysis Patients," 47(1):24-36 (2006).
Willekens, F.L., et al. "Quantification of loss of haemoglobin components from the circulating red blood cell in vivo," *European Journal of Haematology*, 58:246-250 (1997).
Willekens, F.L., et al., "Hemoglobin loss from erythrocytes in vivo results from spleen-facilitated vesiculation," *Blood*, 101:747-751 (2003).
Wu, H., et al. "Generation of committed erythroid BFU-E and CFU-E progenitors does not require erythropoietin or the erythropoietin receptor," *Cell*, 83(1):59-67 (1995).
Formanowica, D., et al., "Petri Net Based Model of the Body Iron Homeostasis", *Journal of Biomedical Informatics*, 40: 476-485 (2007).
Kemna, E., et al., "Time-Course Analysis of Hepcidin, Serum Iron, and Plasma Cytokine Levels in Humans Injected with LPS", *Blood*, 106(5): 1864-1866 (2005).

(56) References Cited

OTHER PUBLICATIONS

Final Office Action for U.S. Appl. No. 14/072,506, "System and Method of Modeling Erythropoiesis Including Iron Homeostasis", dated Sep. 16, 2016.
Non-final Office Action for U.S. Appl. No. 14/072,506, "System and Method of Modeling Erythropoiesis Including Iron Homeostasis", dated May 31, 2016.
Fuertinger, D.H. and Kappel, F., "A Numerical Method for Structured Population Equations Modeling Control of Erythropoiesis" 1st IFAC Workshop on: Control of Systems Governed by Partial Differential Equation, Paris France, 4 pages (2013).
Loeffler, M., et al., "Mathematical model of erythropoiesis in mice and rats, Part 1, Structure of the model," Cell and Tissue Kinetics, 22:13-30 (1989).
Nemeth, E., et al., "Hepcidin Regulates Cellular Iron Efflux by Binding to Ferroportin and Inducing Its Internalization" Science, 306:2090-2093 (2004).
Advisory Action for U.S. Appl. No. 14/072,506, "System and Method of Modeling Erythropoiesis Including Iron Homeostasis", dated Feb. 13, 2017.
Notice of Allowance for U.S. Appl. No. 14/072,506, "System and Method of Modeling Erythropoiesis Including Iron Homeostasis", dated Mar. 2, 2017.
Singh, A.K., et al,, "Correction of Anemia with Epoetin Alfa in Chronic Kidney Disease," The New England Journal of Medicine,355(20):2085-2098 (2006).

\* cited by examiner $$\frac{\partial}{\partial t}p(t,\mu^p) + \frac{\partial}{\partial \mu^p}p(t,\mu^p) = \beta^p p(t,\mu^p),$$

$$\frac{\partial}{\partial t}q(t,\mu^q) + \frac{\partial}{\partial \mu^q}q(t,\mu^q) = (\beta^q - \alpha^q(E(t)))\, q(t,\mu^q),$$

$$\frac{\partial}{\partial t}r(t,\mu^r) + \frac{\partial}{\partial \mu^r}r(t,\mu^r) = \beta^r r(t,\mu^r),$$

$$\frac{\partial}{\partial t}s(t,\mu^s) + v^s(E(t))\frac{\partial}{\partial \mu^s}s(t,\mu^s) = -\alpha^s s(t,\mu^s),$$

$$\frac{\partial}{\partial t}m(t,\mu^m) + \frac{\partial}{\partial \mu^m}m(t,\mu^m) = -\alpha^m(E(t),\mu^m)\, m(t,\mu^m),$$

$$\dot{E}^{end}(t) = \frac{1}{TBV}E^{end}_{in}(t) - c^{end}_{deg}E^{end}(t),$$

$$\dot{E}^{ex}(t) = \frac{1}{TBV}E^{ex}_{in}(t) - c^{ex}_{deg}E^{ex}(t),$$

where $$\alpha^q(E(t)) = \frac{a_1 - b_1}{1 + e^{k_1 E(t) - c_1}} + b_1,$$

$$v^s(E(t)) = \frac{a_2 - b_2}{1 + e^{-k_2 E(t) + c_2}} + b_2,$$

and $$\alpha^m(E(t),\mu^m) = \begin{cases} \alpha^m_r + \min\left(\frac{c_E}{E(t)^{k_E}}, b_E\right) & \text{for } E(t) < \tau_E, \mu^{m,n}_{min} \leq \mu^m \leq \mu^{m,n}_{max}, \\ \alpha^m_r & \text{otherwise,} \end{cases}$$

with boundary conditions $$p(t,0) = S_0,$$
$$q(t,\mu^q_{min}) = p(t,\mu^p_{max}),$$
$$r(t,\mu^r_{min}) = q(t,\mu^q_{max}),$$
$$v^s(E(t))s(t,\mu^s_{min}) = r(t,\mu^r_{max}),$$
$$m(t,0) = v^s(E(t))s(t,\mu^s_{max}),$$
$$m(0,\mu^m) = m_0(\mu^m),$$

and initial values $$p(0,\mu^p) = p_0(\mu^p),$$
$$q(0,\mu^q) = q_0(\mu^q),$$
$$r(0,\mu^r) = r_0(\mu^r),$$
$$s(0,\mu^s) = r_0(\mu^s),$$
$$E^{end}(0) = E^{end}_0,$$
$$E^{ex}(0) = E^{ex}_0.$$

FIG. 3

| Parameter | Meaning | Value and Unit |
|---|---|---|
| $\beta^p$ | proliferation rate for BFU-E cells | 0.2 1/d |
| $\beta^q$ | proliferation rate for CFU-E cells | 0.57 1/d |
| $\beta^r$ | proliferation rate for erythroblasts | 1.024 1/d |
| $\mu^p_{max}$ | maximal maturity for BFU-E cells | 7 d |
| $\mu^q_{min} = \mu^p_{max}$ | minimal maturity for CFU-E cells | 7 d |
| $\mu^q_{max}$ | maximal maturity for CFU-E cells | 13 d |
| $\mu^r_{min} = \mu^q_{max}$ | minimal maturity for erythroblasts | 13 d |
| $\mu^r_{max}$ | maximal maturity for erythroblasts | 18 d |
| $\mu^s_{min} = \mu^r_{max}$ | minimal maturity for marrow reticulocytes | 18 d |
| $\mu^s_{max}$ | maximal maturity for marrow reticulocytes | 20 d |
| $\alpha^s$ | rate of ineffective erythropoiesis | 0.089 1/d |
| $\alpha^m_r$ | intrinsic mortality rate for erythrocytes | 0.005 1/d |
| $a_1, b_1$ | constants for the sigmoid apoptosis rate for CFU-E cells | 0.35, 0.07 1/d |
| $c_1, k_1$ | constants for the sigmoid apoptosis rate for CFU-E cells | 2, 0.07 ml/mU |
| $a_2, b_2$ | constants for the sigmoid maturation velocity for marrow reticulocytes | 2, 0.35 |
| $c_2, k_2$ | constants for the sigmoid maturation velocity for marrow reticulocytes | 2.3, 0.1 ml/mU |
| $a_3, b_3$ | constants for the sigmoid function governing the release of EPO from the kidneys | 90, 10 mU/(ml×d) |
| $c_3, k_3$ | constants for the sigmoid function governing the release of EPO from the kidneys | 9.1, 0.1 ml |
| $\mu^{m,n}_{min}$ | lower bound of erythrocytes which are possibly exposed to neocytolysis | 14 d |
| $\mu^{m,n}_{max}$ | lower bound of erythrocytes which are possibly exposed to neocytolysis | 21 d |
| $\mu_{max}$ | maximal life span for erythrocytes | 120 |
| $c_E$ | constant in the mortality rate for erythrocytes | 3.5 $mU^3/ml^2$ |
| $\tau_E$ | EPO threshold for neocytolysis | 9.8 mU/ml |
| $c^{end}_{deg}$ | degradation rate of EPO released by the kidney | 25/24 1/d |
| $c^{ex}_{deg}$ | degradation rate of administered EPO (Epoetin alfa) | 8.5/24 1/d |
| $S_0$ | number of cells committing to the erythroid lineage | $10^8$ |
| TBV | total blood volume | 5000 ml |

FIG. 4A

| Parameter | Meaning | Value and Unit |
|---|---|---|
| $\beta^p$ | proliferation rate for BFU-E cells | 0.6 1/d |
| $\beta^q$ | proliferation rate for CFU-E cells | 1.2 1/d |
| $\beta^r$ | proliferation rate for erythroblasts | 0.723 1/d |
| $\mu^p_{max}$ | maximal maturity for BFU-E cells | 3 d |
| $\mu^q_{min} = \mu^p_{max}$ | minimal maturity for CFU-E cells | 3 d |
| $\mu^q_{max}$ | maximal maturity for CFU-E cells | 5 d |
| $\mu^r_{min} = \mu^q_{max}$ | minimal maturity for erythroblasts | 5 d |
| $\mu^r_{max}$ | maximal maturity for erythroblasts | 13 d |
| $\mu^s_{min} = \mu^r_{max}$ | minimal maturity for marrow reticulocytes | 13 d |
| $\mu^s_{max}$ | maximal maturity for marrow reticulocytes | 15 d |
| $\alpha^s$ | rate of ineffective erythropoiesis | 0.09 1/d |
| $\alpha^m_r$ | intrinsic mortality rate for erythrocytes | 0.002 1/d |
| $a_1, b_1$ | constants for the sigmoid apoptosis rate for CFU-E cells | 0.5, 0 1/d |
| $c_1, k_1$ | constants for the sigmoid apoptosis rate for CFU-E cells | 0.5, 0.01 ml/mU |
| $a_2, b_2$ | constants for the sigmoid maturation velocity for marrow reticulocytes | 2, 0.35 |
| $c_2, k_2$ | constants for the sigmoid maturation velocity for marrow reticulocytes | 2.3, 0.2 ml/mU |
| $a_3, b_3$ | constants for the sigmoid function governing the release of EPO from the kidneys | 810, 90 mU/(ml×d) |
| $c_3, k_3$ | constants for the sigmoid function governing the release of EPO from the kidneys | 9.1, 0.2 ml |
| $\mu^{m,n}_{min}$ | lower bound of erythrocytes which are possibly exposed to neocytolysis | 14 d |
| $\mu^{m,n}_{max}$ | lower bound of erythrocytes which are possibly exposed to neocytolysis | 21 d |
| $\mu_{max}$ | maximal life span for erythrocytes | 120 |
| $c_E$ | constant in the mortality rate for erythrocytes | $3.5\ mU^3/ml^2$ |
| $\tau_E$ | EPO threshold for neocytolysis | 80 mU/ml |
| $c^{end}_{deg}$ | degradation rate of EPO released by the kidney | 25/24 1/d |
| $c^{ex}_{deg}$ | degradation rate of administered EPO (Epoetin alfa) | 8.5/24 1/d |
| $S_0$ | number of cells committing to the erythroid lineage | $0.083 \times 10^8$ |
| TBV | total blood volume | 5000 ml |

FIG. 4B

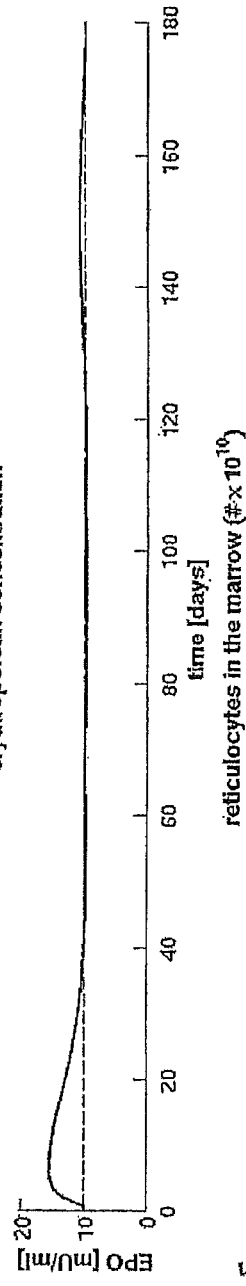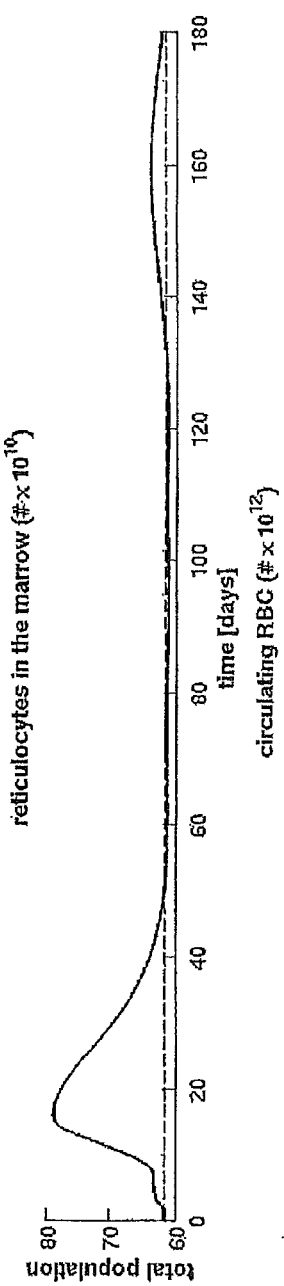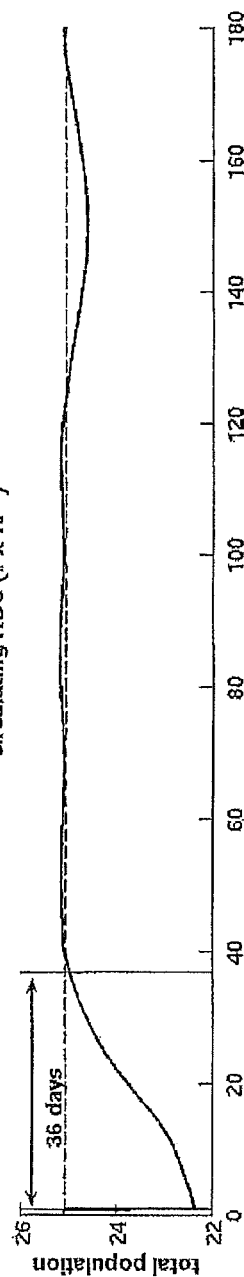
FIG. 7A
FIG. 7B
FIG. 7C

SYSTEM AND METHOD OF MODELING ERYTHROPOIESIS AND ITS MANAGEMENT

RELATED APPLICATION

This application is the U.S. National Stage of International Application No. PCT/US2012/054264, filed Sep. 7, 2012, which designates the U.S., published in English, and claims the benefit of U.S. Provisional Application No. 61/532,290, filed on Sep. 8, 2011. The entire teachings of the aforementioned applications are incorporated herein by reference.

BACKGROUND OF THE INVENTION

Red blood cells (erythrocytes) are essential for the transport of oxygen through the body. An understanding of the regulation of red blood cell production, called erythropoiesis, is important for the treatment of patients in a variety of clinical situations. Patients that are scheduled for elective surgery, such as hip or transplant surgery, can be prescribed an erythropoiesis stimulating agent (ESA) to compensate for the expected loss of blood, thus obviating the need for allogenic blood transfusions by raising the patient's hematocrit and/or hemoglobin concentration to a desired range at the predetermined time, in expectation of the surgery. Erythropoiesis stimulating agents, including recombinant human erythropoietin, exert hematological effects analogous to the hormone erythropoietin (EPO), which is released into the blood stream by the kidneys based on a negative feedback mechanism that reacts to the partial pressure of oxygen in the blood. ESA treatment regimens are also prescribed for patients who suffer from insufficient erythropoiesis, such as cancer patients recovering from the effects of chemotherapy, and chronic kidney disease patients whose kidneys can no longer produce sufficient amounts of EPO. The dose and frequency of administration of an ESA treatment regimen are often determined based on the prior experience of the physician and on established guidelines, because predictive models of erythropoiesis under an ESA treatment regimen are not readily available.

Therefore, there is a need for a predictive model of erythropoiesis under various ESA treatment regimens.

SUMMARY OF THE INVENTION

A model for erythropoiesis in humans is provided that is based on structured population models for the different cell stages in development, from stem cells in bone marrow to erythrocytes in the blood stream.

In one embodiment, a method of adjusting a patient's hematocrit and/or hemoglobin concentration to a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, and employing the patient parameters and an initially selected EPO administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, the method includes employing the model with one or more different ESA administration regimens until the model predicts that the patient's hematocrit and/or hemoglobin concentration will be in the desired range at the predetermined time. The method then includes administering ESA to the patient with the ESA administration regimen predicted to adjust the patient's hematocrit and/or hemoglobin concentration to the desired range at the predetermined time. The patient parameters can include the starting hematocrit and/or hemoglobin concentration in the patient's blood, the total blood volume of the patient, the lifespan of red blood cells (RBCs) of the patient, the mean corpuscular volume of the RBCs, and the rate of neocytolysis in the patient's blood.

The predetermined time can be, for example, in a range of between about 5 days and about 200 days into the ESA administration regimen. In some embodiments, the patient undergoes a medical procedure prior, during, or after initiation of an ESA administration regimen, including medical procedures such as blood donation, surgery, and dialysis, or any combination thereof. For dialysis patients, the desired hematocrit can be, for example, in the range of between about 28 percent and about 36 percent and the desired hemoglobin concentration can be, for example, in a range of between about 9.5 g/dL and about 12 g/dL.

In yet another embodiment, a computer system for adjusting a patient's hematocrit and/or hemoglobin concentration to a desired range at a predetermined time with an erythropoiesis stimulating agent (ESA) regimen includes a user input means for determining patient parameters from a user, a digital processor coupled to receive determined patient data from the input means, wherein the digital processor executes a modeling system in working memory, and an output means coupled to the digital processor, the output means provides to the user the patient's hematocrit and/or hemoglobin concentration under the ESA administration regimen at the predetermined time. The modeling system employs the patient parameters and an initially selected EPO administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, employs the model with one or more different ESA administration regimens until the model predicts that the patient's hematocrit and/or hemoglobin concentration will be in the desired range at the predetermined time.

In still another embodiment, a method of determining a patient's hematocrit and/or hemoglobin concentration within a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, and employing patient parameters and an initially selected EPO administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, the method includes employing the model with one or more different ESA administration regimens until the model predicts that the patient's hematocrit and/or hemoglobin concentration will be in the desired range at the predetermined time. The method then can include administering ESA to the patient with the ESA administration regimen predicted to adjust the patient's hematocrit and/or hemoglobin concentration to the desired range at the predetermined time.

This invention has many advantages, including the achievement of an ESA regimen needed for a desired hematocrit and/or hemoglobin concentration for a patient, thereby, on the one hand, alleviating insufficient erythropoiesis, and, on the other hand, preventing excessively high ESA dose levels that raise the patient's blood pressure and increase the patient's risk of stroke and cardiovascular disease.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3 sets forth model equations according to this invention.

FIG. 4A is a list of definitions for model parameters for the equations set forth in FIG. 3.

FIG. 4B is a list of model parameters for the equations set forth in FIG. 3 considering a shortened transit time of progenitor cells.

FIGS. 5C-1, 5C-2, and 5C-3 set forth graphs of sigmoidal functions used to describe the rate of apoptosis of CFU-E cells (FIG. 5C-1), the maturation velocity of reticulocytes (FIG. 5C-2), and the release of EPO by the kidneys (FIG. 5C-3).

FIGS. 7A-7C set forth graphs simulating the effect of donation of 550 ml of blood on: 7A: EPO concentration as a function of time, 7B: total population of reticulocytes in the bone marrow as a function of time, and 7C: total population of RBC as a function of time, according to the model of this invention.

DETAILED DESCRIPTION OF THE INVENTION

Figure 1A:
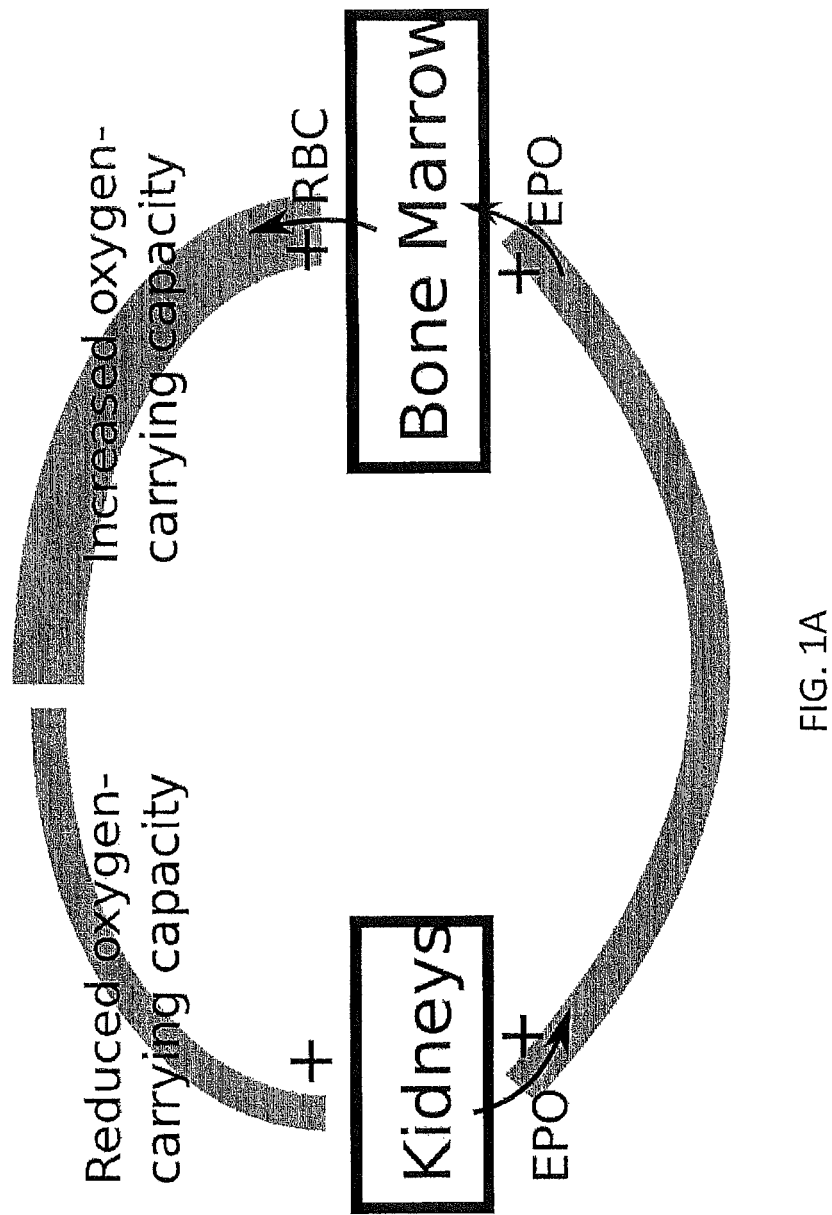
FIG. 1A is a schematic illustration of how a reduced oxygen carrying capacity stimulates the kidneys to release more EPO, and an elevated EPO level results in more erythrocytes developing in the bone marrow, thus, increasing the oxygen carrying capacity.

Red blood cells (erythrocytes) are essential for the distribution of oxygen through the body to organs and tissues. They take up oxygen in the lungs and deliver it to tissues while squeezing through the capillaries. To fulfill this task properly, they are highly specialized. For instance, being shaped like biconcave disks optimizes the oxygen exchange. Furthermore, they give up their nuclei, organelles, and mitochondria in order to provide more space for hemoglobin, the molecule which oxygen binds to. Erythrocytes are very deformable and can therefore pass capillaries half their diameter. During microcirculation, they have to withstand high shear stresses, rapid elongation, folding, and deformation. Over time, the cell membrane is damaged by these extraordinary stresses. Because of the lack of nuclei and organelles, red blood cells cannot divide or repair their cell membranes. Senescent erythrocytes lose their flexibility due to their fragmented membranes. These stiff cells could do harm to small capillaries or even clog them. To avoid this potential harm, old erythrocytes are recognized by phagocytes and destroyed. This phagocytosis mainly takes place in the spleen and cells of the reticulo-endothelial system (RES). See Jandl, J. H., Blood: Textbook of Hematology, 2$^{nd}$ Ed. Little, Brown and Company, 1996 (hereinafter "Jandl").

To compensate for phagocytosis of senescent red blood cells, it is necessary to build new erythrocytes continuously. The maturation of undifferentiated stem cells to mature erythrocytes is called erythropoiesis and takes place in the bone marrow. Erythropoiesis not only has to compensate for the continuous loss of old erythrocytes, but also for the additional loss of cells due to random breakdown, as well as due to internal and external bleeding. Furthermore, the number of red blood cells has to be adjusted to varying environmental conditions, as for instance a transition from low to high altitudes or vice versa, by increasing the rate of erythropoiesis, or, conversely, by neocytolysis, a process believed to be wherein macrophages start to phagocytose young erythrocytes (neocytes).

During the process of erythropoiesis, the cell population undergoes a series of proliferations and differentiations. Starting from multipotential stem cells, erythroid cells mature to BFU-Es (earliest stage of erythroid committed cells), CFU-Es, different stages of erythroblasts, and finally reticulocytes. The reticulocytes are released from the bone marrow into blood and mature within 1-2 days to erythrocytes (see FIG. 1B).

The primary control of erythropoiesis is governed by the hormone erythropoietin (EPO). EPO is released into the blood stream by the kidneys based on a negative feedback mechanism that reacts to the partial pressure of oxygen in blood. The concentration of EPO affects the number of circulating red blood cells by determining the number of cells that mature into erythrocytes, either by recruitment or by preventing apoptosis (programmed cell death), and by affecting the velocity of maturing of progenitor and precursor cells. Thus, disturbances in oxygen delivery can be adjusted for by an adaptive resetting of the rate of erythropoiesis. Additionally, as already mentioned above, there exists a physiological process which affects the selective degradation of young erythrocytes in situations of red cell excess, called neocytolysis. Neocytolysis seems to be triggered by a drop in the EPO level. See Rice, L., and Alfrey, C. P., The negative regulation of red cell mass by neocytolysis: Physiologic and pathophysiologic manifestations, Cellular Physiology and Biochemistry, 2005, Vol. 15, pp. 245-250 (hereinafter "Rice 2005"); Rice, L., Alfrey, C. P., Driscoll, T., Whitley, C. E., Hachey, D. L., and Suki, W., Neocytolysis contributes to the anemia of renal disease, Amer. J. Kidney Diseases, 1999, Vol. 33, pp. 59-62 (hereinafter "Rice 1999"); and Rice, L., W. Ruiz, W., Driscoll, T., Whitley, C. E., Tapia, R., Hachey, D. L., Conzales, G. F., and Alfrey, C. P., Neocytolysis on descent from altitude: A newly recognized mechanism, Annals Internal Medicine. 2001, Vol. 134, pp. 652-656 (hereinafter "Rice 2001").

Another critical factor for effective erythropoiesis is the availability of iron which is indispensable for hemoglobin synthesis. If the body is not able to provide sufficient iron for this process, then ineffective erythropoiesis will result. See Finch, S., Haskins, D., and Finch, C. A., Iron metabolism. Hematopoiesis following phlebotomy. Iron as a limiting factor, The Journal of Clinical Investigation. 1950, Vol. 29, pp. 1078-1086; and Lichtman, M. A., E. Beutler, E., Kipps, T. J., Seligsohn, U., Kaushansky, K., and Prchal, J. T. (editors), Williams Hematology, 7th edition, New York, McGraw-Hill, 2005 (hereinafter "Williams Hematology"). In normal subjects, the total iron content of the body stays within narrow limits (iron overload is toxic). Once an atom of iron enters the body it is conserved with remarkable efficiency and can remain in the body for more than ten years. Iron is lost via loss of cells (especially epithelial cells), bleeding and loss of very small amounts via urine and sweat. The balance of iron content is achieved by absorption and not by control of excretion. If the plasma concentration of iron is too low, then the level of the hormone hepcidin is decreased. The consequence of a lower hepcidin level is that more iron is taken up via the duodenum and more iron is released from macrophages and from the stores. See Crichton, R., Iron Metabolism. From Molecular Mechanisms to Clinical Consequences, New York, J. Wiley, 2009; and Fleming, M. D., The regulation of hepcidin and its effects on systemic and cellular iron metabolism, Hematology, J. Amer. Soc. Hematology, 2008, pp. 151-158. Patients suffering from inflammation, such as dialysis patients, typically have higher hepcidin levels. Increasing iron availability in inflamed dialysis patients can be achieved by an increase of parenteral iron by increasing dose, frequency, or both, and by reducing inflammation by diagnosis and treatment of sources of inflammation, e.g., barrier breakdown (i.e., skin, periodontal disease, intestinal congestion), pulmonary or urinary tract infection, thrombosed fistulas or catheter, and by subsequent specific therapy, e.g., antibiotics, catheter removal, aseptic techniques when manipulating in-dwelling catheters, and surgical debridement of skin ulcers.

Since individual cells in the various cell populations which have to be considered have to be distinguished according to their age, age-structured population models are needed in order to describe the development of the cell populations. Besides these age-structured population models, the model of this invention includes a feedback loop including erythropoietin. In the model development below, iron supply is fixed to a rate which corresponds to a sufficient supply of iron one would expect in a healthy person (without iron deficiency).

In one embodiment, a method of adjusting a patient's hematocrit and/or hemoglobin concentration to a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, and employing the patient parameters and an initially selected EPO administration regimen in the model to predict the patient's hematocrit and/or hemoglobin concentration at the predetermined time with the initially selected ESA administration regimen. Examples of ESAs are provided in Table 1 (adapted from Phurrough S, Jacques L, Ciccanti M, Turner T, Koller E, Feinglass S: "Proposed Coverage Decision Memorandum for the Use of Erythropoiesis Stimulating Agents in Cancer and Related Neoplastic Conditions"; Centers for Medicare and Medicaid Services; Administrative File: CAG #000383N; May 14, 2007). See also Pfeffer, M. A., Burdmann, E. A., Chen, C-Y., Cooper, M. E., de Zeeuw, D., Eckardt, K-U., Feyzi, J. M., Ivanovich, P., Kewalramani, R., Levey, A. S., Lewis, E. F., McGill, J. B., McMurray, J. J. V., Parfrey, P., Parving, H-H., Remuzzi, G., Singh, A. K., Solomon, S. D., Toto, R., A Trial of Darbepoetin Alfa in Type 2 Diabetes and Chronic Kidney Disease, The New England Journal of Medicine, 2009, 361(21), pp. 2019-2032; and Singh, A. K., Szczech, L., Tang, K. L., Barnhart, H., Sapp, S., Wolfson, M., Reddan, D., Correction of Anemia with Epoetin Alfa in Chronic Kidney Disease, The New England Journal of Medicine, 2006, 355(20), pp. 2085-2098 (hereinafter "Singh et al."). Note that unlike other ESAs listed in Table 1, Peginesatide is not a biologically derived EPO, it is a synthetic peptide that stimulates EPO receptors.

TABLE 1

Erythropoiesis Stimulating Agents: EPO = erythropoietin.

| Compound | Drug Names | Manufacturer |
| --- | --- | --- |
| EPO α | Epogen ® | Amgen |
| EPO α | Procrit ® | Amgen |
| EPO α (w/o serum albumin) | Eprex ® Epypo ® Epopen ® Epoxitin ® Globuren ® | J&J subsidiary (Otho Biologics) |
| EPO β | (Neo)Recormon | Roche |
| EPO β | Erantin ® | Boehringer Mannheim (Spain), Roche (Spain) |
| EPO β | Epoch ® | Chugai |
| EPO δ in human cell lines | Dynepo Gene Activated EPO | Aventis Transkaryotic Therapies |
| EPO Ω | Epomax ® Hemax ® Hemax ®-Eritron ® | Baxter |
| Modified EPO α Darbepoietin | Aranesp ® | Amgen |

TABLE 1-continued

Erythropoiesis Stimulating Agents: EPO = erythropoietin.

| Compound | Drug Names | Manufacturer |
| --- | --- | --- |
| Modified EPO α Darbepoietin | Nespo ® | Amgen |
| Modified EPO β Continuous EPO Receptor Activator (Pegylation) | Mircera ® | Roche |
| Peginesatide | Omontys ® | Affymax |

Optionally, if the patient's hematocrit and/or hemoglobin concentration is not predicted by the model to be in the desired range at the predetermined time with the initially selected ESA administration regimen, the method includes employing the model with one or more different ESA administration regimens until the model predicts that the patient's hematocrit and/or hemoglobin concentration will be in the desired range at the predetermined time. The method then includes administering ESA to the patient with an ESA administration regimen predicted to adjust the patient's hematocrit and/or hemoglobin concentration to a value within the desired range at the predetermined time. The patient parameters can include the starting hematocrit and/or hemoglobin concentration in the patient's blood, the total blood volume of the patient, the lifespan of red blood cells (RBCs) of the patient, the mean corpuscular volume of the RBCs, and the rate of neocytolysis in the patient's blood. The starting hematocrit and/or hemoglobin concentration in the patient's blood can be obtained from routine laboratory measurements known in the art. The total blood volume (BV) of the patient can be estimated as described further below, or measured by use of radio-labeling red blood cells with chromium-51 to estimate red blood cell volume (RCV) and using the formula $$BV=RCV/(0.9*Hctv)$$

where Hctv is the venous hematocrit, obtained from routine laboratory measurements known in the art. See Albert S. N., Blood volume measurement, In: Nuclear Medicine In Vitro. 2 ed. Philadelphia: JB Lippincott Co., 1983; Bernard P. J., Measurement of red-cell and plasma volumes, Nouv Rev Fr Hematol 1994, 36(2), pp. 155-157; and International Committee for Standardization in Haematology: Recommended methods for measurement of red-cell and plasma volume, J Nucl Med 1980, 21(8), pp. 793-800. The lifespan of RBCs of the patient can be estimated from endogenous alveolar carbon monoxide concentrations. See Strocchi A., Schwartz S., Ellefson M., Engel R. R., Medina A., Levitt M. D., A simple carbon monoxide breath test to estimate erythrocyte turnover, J Lab Clin Med 1992, 120(3), pp. 392-399. The mean corpuscular volume can be obtained from routine laboratory measurements known in the art. The rate of neocytolysis in the patient's blood can be estimated from correlations with reduced expression of CD44 (homing-associated cell adhesion molecule) and CD71 (transferrin receptor). See Chang C. C., Chen Y., Modi K., Awar O., Alfrey C., Rice L., Changes of red blood cell surface markers in a blood doping model of neocytolysis, J Investig Med 2009, 57(5), pp. 650-654.

The model of this invention can track the patient's predicted hematocrit and/or hemoglobin concentration over time, such as between about 5 days and about 200 days of the ESA administration regimen. The predetermined time can be any future time after an ESA administration regimen is selected and the predicted regimen is initiated. In some embodiments, the patient undergoes a medical procedure prior, during, or after the ESA administration regimen, such as blood donation, surgery, and dialysis, or any combination thereof. For dialysis patients, the desired hematocrit is typically in the range of between about 28 percent and about 36 percent and the desired hemoglobin concentration is typically in a range of between about 9.5 g/dL and about 12 g/dL. See Driieke, T. B., Locatelli, F., Clyne, N., Eckardt, K-U., Macdougall, I. C., Tsakiris, D., Burger, H-U., Scherhad, A., Normalization of Hemoglobin Level in Patients with Chronic Kidney Disease and Anemia, The New England Journal of Medicine, 2006, 355(20), pp. 2071-2084; Parfrey, P. S., Target Hemoglobin Level for EPO Therapy in CKD, 2006, American Journal of Kidney Diseases, 47(1), pp. 171-173; Strippoli, G. F. M., Craig, J. C., Manno, C., Schena, F. P., Hemoglobin Targets for the Anemia of Chronic Kidney Disease: A Meta-analysis of Randomized, Controlled Trials, Journal of the American Society of Nephrology, 2004, 15, pp. 3154-3165 (hereinafter "Strippoli et al."); Volkova, N., Arab, L., Evidence-Based Systematic Literature Review of Hemoglobin/Hematocrit and All-Cause Mortality in Dialysis Patients, 2006, 47(1), pp. 24-36. For elective orthopaedic surgery patients, the desired hemoglobin concentration for males and females is typically greater than or equal to 13 g/dL, and 12 g/dL, respectively. See Goodnough L. T., Maniatis A., Earnshaw P., Benoni G., Beris P., Bisbe E., Fergusson D. A., Gombotz H., Habler O., Monk T. G., Ozier Y, Slappendel R., and Szpalski M., Detection, evaluation and management of preoperative anaemia in the elective orthopaedic surgical patient: NATA guidelines, British Journal of Anaesthesia 106 (1) pp. 13-22 (2011).

In another embodiment, a method of determining a patient's hematocrit and/or hemoglobin concentration within a desired range at a predetermined time with an erythropoiesis stimulating agent (ESA) regimen includes obtaining patient parameters required for input into a model for predicting the patient's hematocrit and/or hemoglobin concentration at a predetermined time with a selected ESA administration regimen, and employing the patient parameters and an initially selected EPO administration regimen in the model to predict the patient's hematocrit and/or hemoglobin concentration at the predetermined time with the initially selected ESA administration regimen. Optionally, if the patient's hematocrit and/or hemoglobin concentration is not predicted by the model to be in the desired range at the predetermined time, or a different ESA administration regimen is desired due to other considerations, the method includes employing the model with one or more different ESA administration regimens until the model predicts that the patient's hematocrit and/or hemoglobin concentration will be in the desired range at the predetermined time. The method then can include administering ESA to the patient with the ESA administration regimen predicted to adjust the patient's hematocrit and/or hemoglobin concentration to a value within the desired range at the predetermined time.

An erythrocyte that reaches an age of 120 days, has traveled approximately 480 kilometers, making about 170,000 circuits, in each cycle enduring osmotic swelling and shrinkage and a number of deformations while passing through capillaries. The accumulated damage to the membrane of the RBC is believed to lead to the destruction of the cell.

About two decades ago it was observed that erythrocytes actually undergo suicidal death. The suicidal death of erythrocytes is called eryptosis. This term was chosen in order to point out the differences from and similarities to apoptosis, the programmed cell death of nucleated cells. Although, there exist a number of studies concerning eryptosis and some parts are understood in great detail the precise process and mechanisms remain elusive.

Stimulation of eryptosis is governed by a complex signaling network and involves activation of cation channels. (F. Lang, C. Birka, S. Myssina, K. S. Lang, P. A. Lang, V. Tanneur, C. Duranton, T. Wieder, and S. M. Huber. Erythrocyte ion channels in regulation of apoptosis. *Advances in Experimental Medicine and Biology,* 559:211-217, 2004). Shortly before they are phagocytosed by macrophages, which takes place mainly in the spleen, one can observe distinctive cell shrinkage, plasma membrane microvesiculation and an exposure of phosphatidylserine (PS) on the cell surface. These PS-exposing erythrocytes are recognized, engulfed and degraded by macrophages. (D. Bratosin, J. Estaquier, F. Petit, D. Arnoult, B. Quatannens, J. P. Tissier, C. Slomianny, C. Sartiaux, C. Alonso, J. J. Huart, J. Montreuil, and J. C Ameisen. Programmed cell death in mature erythrocytes: a model for investigating death effector pathways operating in the absence of mitochondria. *Cell Death Differ,* 8(12):1143-1156, December 2001).

The normal lifespan and senescence can be either accelerated or delayed by environmental signals. Triggers of eryptosis include osmotic shock, oxidative stress, prostaglandin E2, energy depletion, chlorpromazine, aluminum, mercury, etc. Diseases which are associated with an early expression of PS and thus accelerated eryptosis are, for instance, iron deficiency, sepsis, hemolytic uremic syndrome and sickle-cell anemia. (R. F. Zwaal, P. Comfurius, and E. B. Bevers. Surface exposure of phosphatidylserine in pathological cells. *Cellular and molecular life sciences,* 62:971-988, 2005). On the other hand eryptosis may be inhibited by erythropoietin, adenosine, catecholamines, nitric oxide and activation of G-kinase. (M. Föller, S. M. Huber, and F. Lang. Erthrocyte programmed cell death. *IUBMB LIfe,* 60:661-668, 2008). Thus, EPO seems not only to increase the number of circulating erythrocytes by preventing apoptosis of progenitor cells but also by prolonging the lifespan of circulating RBC by inhibiting the cation channels. (F. Lang, K. S. Lang, P. A. Lang, S. M. Huber, and T. Wieder. Mechanisms and significance of eryptosis. *Antioxidants & Redox Signaling,* 8:1183-1192, 2006; A. B. Schwartz, B. Kelch, L. Terzian, J. Prior, K. E. Kim, E. Pequinot, and B. Kahn. One year of rHuEPO therapy prolongs RBC survival may stabilize RBC membranes despite natural progression of chronic renal failure to uremia and need for dialysis. *ASAIO transactions,* 36:M691-M696, 1990). The cation channels are volume-sensitive and after activation of the channel phosphatidylserine asymmetry breaks down. Binding of erythropoietin to RBC and inhibition of the channels may contribute to an increase in the erythrocyte number during erythropoietin therapy. (S. Myssina, S. M. Huber, C. Birka, P. A. Lang, K. S. Lang, B. Friedrich, T. Risler, T. Wieder, and F. Lang Inhibition of erythrocyte cation channels by erythropoietin. *Journal of American Society of Nephrology,* 14:2750-2757, 2003). Surprisingly, it was recently observed, that erythrocytes from erythropoietin overexpressing mice die faster ex vivo. (M. Foeller, R. S. Kasinathan, S. Koka, S. M. Huber, B. Schuler, J. Vogel, M. Gassmann, and F. Lang. Enhanced susceptibility to suicidal death of erythrocytes from transgenic mice overexpressing erythropoietin. *American Journal of Physiology—Regulatory, Integrative and Comparative Physiology,* 293:R1127-R1134, 2007). This observation leaves room for discussion. It has been suggested that: "Possibly, erythropoietin stimulates the expression of genes in progenitor cells, which foster eryptosis and thus accelerate erythrocyte death as soon as the erythropoietin concentrations decline." (See F. Lang, E. Gulbins, H. Lerche, S. M. Huber, D. S. Kempe, and M. Föller. Eryptosis, a window to systemic disease. *Cellular Physiology and Biochemistry*, 22:373-380, 2008).

Erythropoiesis and its Regulatory Mechanisms

The daily production rate in a healthy adult totals about $200 \times 10^9$ red blood cells under normal conditions. This number can vary due to varying internal and environmental conditions. The body has to be able to adapt the number of erythrocytes to situations of anemia and/or hypoxia (e.g. after bleeding, due to a shortened RBC lifespan, due to an enhanced eryptosis, . . . ) as well as to situations of excessive red blood cells (e.g., high altitude dwellers descending to sea level).

The production of new erythrocytes takes place in the bone marrow. Undifferentiated stem cells in the bone marrow commit to the erythroid lineage and undergo a series of proliferations and differentiations. The earliest stage of erythroid committed cells are called BFU-Es (Burst-Forming Unit Erythroid). Within a few days the BFU-Es mature to CFU-Es (Colony-Forming Unit Erythroid), then they undergo different stages of erythroblasts and finally they become reticulocytes. The reticulocytes are released to the blood stream and within 1-2 days they appear as mature erythrocytes. (See Williams Hematology). Throughout the description below, the term progenitor cells is used to refer to BFU-E and CFU-E cells and the term precursor cells is used to subsume proerythroblasts, basophilic erythroblasts, orthochromatophilic erythroblasts and bone marrow reticulocytes.

The primary control of erythropoiesis is governed by the hormone erythropoietin. EPO is produced mainly by peritubular cells in the renal cortex based on a negative feedback mechanism. The kidneys detect the partial pressure of oxygen in blood and react by releasing more EPO if the oxygen content is too low and vice versa. The concentration of EPO affects the number of circulating RBC by determining the number of cells that mature into erythrocytes. Erythropoietin plays a role in the recruitment of stem cells to the erythroid lineage, prevents apoptosis of progenitor cells and affects the maturation velocity of progenitor and precursor cells. Thus, disturbances in oxygen delivery can be adjusted for by an adaptive resetting of the rate of erythropoiesis, as shown in FIG. 1A. Additionally, there exists a physiological process, wherein macrophages start to phagocytose young erythrocytes (neocytes), which is called neocytolysis. Neocytolysis seems to be triggered by a drop in the EPO level and helps to regulate situations of excessive red cell mass. (See Rice 2001). Further, recent studies suggest that the concentration of EPO in blood influences the clearance of senescent RBCs and that EPO can prolong the lifespan of erythrocytes by inhibiting cation channels.

Progenitor and Precursor Cells

Once a stem cell committed to the erythroid lineage, the cell can not regress or switch to another hematopoietic lineage, but can only develop to an erythrocyte. The number of stem cells which enter the different hematopoietic lineages is determined by interleukines and growth factors. The immature erythrocyte undergoes a number of changes in structure, appearance and its requirements during the process of differentiation and proliferation. BFU-E cells, the first committed erythroid cells, express only a very small number of EPO-receptors (EpoR) and therefore they are almost EPO-independent for their survival. Within a few days they develop into CFU-E cells.

As cells mature to CFU-Es the number of EpoR on the cell surface increases distinctly and the cells become absolutely dependent on erythropoietin to prevent them from apoptosis. (H. Wu, X. Liu, R. Jaenisch, and H. F. Lodish. Generation of committed erythroid BFU-E and CFU-E progenitors does not require erythropoietin or the erythropoietin receptor. *Cell*, 83(1):59-67, 1995) (hereinafter "Wu et al."). Under normal conditions, large numbers of generated CFU-E are not surviving. After that very EPO-sensitive phase the density of EpoRs declines sharply on early erythroblasts and EpoRs almost disappear at the stage of orthochromatophilic erythroblasts. (J. P. Greer, J. Foerster, G. M. Rodgers, F. Paraskevas, B. Glader, D. A. Arber, and R. T. Jr. Means. *Wintrobe's Clinical Hematology*, volume 1. Lippincott Williams & Wilkins, 12th edition, 2009) (hereinafter "Wintrobe's Clinical Hematology"). Under high levels of EPO the marrow transit time of precursor cells is shortened and high EPO levels result in release of still immature reticulocytes, which are referred to as stress reticulocytes. (See Williams Hematology).

Figure 1B:
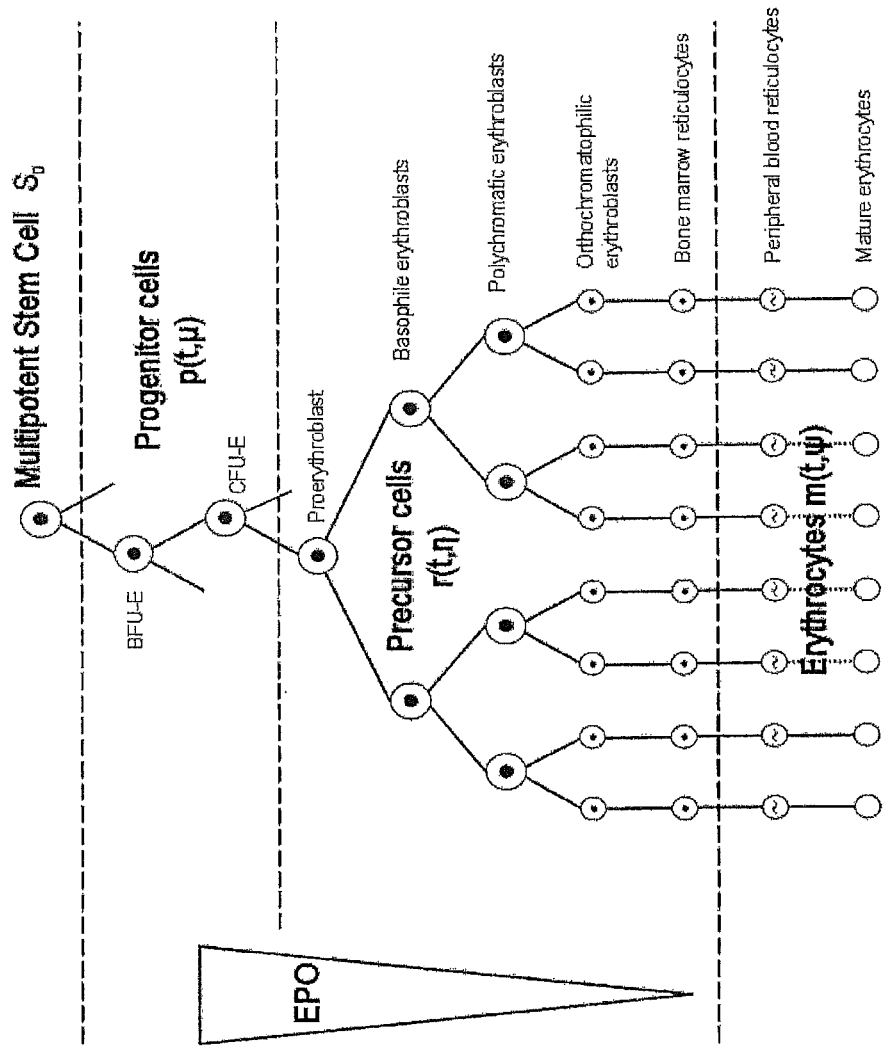
FIG. 1B is a schematic illustration of cell stages during erythropoiesis in a human being.
Figure 2:
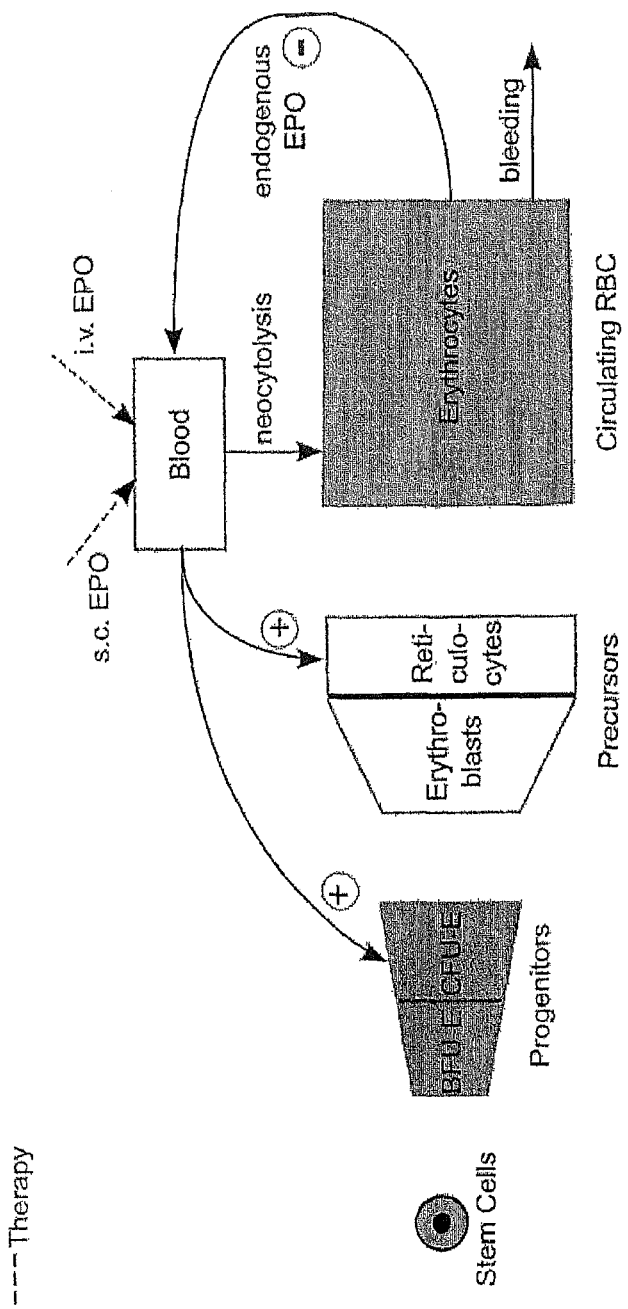
FIG. 2 is a schematic illustration of the organizational diagram of the model according to this invention.

One significant difference between progenitor and precursor cells is the synthesis of hemoglobin. Unlike progenitor cells, all types of precursor cells synthesize heme and the increased demand for iron for this process is reflected by a sharp increase in the number of transferrin receptors (TfR) in proerythroblasts (transferring receptors are the only path of iron uptake). TfRs reach their peak in intermediate erythroblasts and decline afterward and mature bone marrow reticulocytes express only a few TfRs (in comparison). A diagram of the different erythroid cell types is shown in FIG. 1B.

Neocytolysis

The body has to be able to deal with situations of too few circulating erythrocytes as well as with excessive red blood cells. Whereas it is very effective to change the rate of erythropoiesis to adapt the system to situations when red cell numbers are low, this is not an adequate regulatory mechanism in situations of red cell mass excess. This is because a decrease in the rate of erythropoiesis takes relatively long to have a noticeable effect on the number of circulating red blood cells, due to the long lifespan of erythrocytes.

A mere 20 years ago preventing apoptosis of red cell progenitors had been thought to be the sole regulating effect of EPO. Because this would only allow for a slow adaptation in situations of too many RBC, the control of the body of red cell mass would be coarse. A decline in erythropoietin level results in more progenitor cells dying but a suppression of the hormone has no effect on maturation of erythroid precursors. Thus, no decrement in the erythrocyte production would be observable within one week after EPO has declined. However, studies done on residents at very high altitude who rapidly descended to sea level, showed a decrease in red cell mass of 10-18% in the first 7-10 days. (See Rice 2001). Persons living in hypoxic environments, like high altitude, are normally polycythemic. Thus, their hematocrit is too high under normal conditions and as a consequence the release of EPO is suppressed.

Further investigations of situations where EPO levels are lower than normal (polycythemic high altitude dwellers, anemia of renal failure, human model based on EPO administration then withdrawal), suggest that a suppression of EPO leads to selective hemolysis of young red blood cells. (See Rice 2005). This process is called neocytolysis, to stress the fact that young erythrocytes (=neocytes) are uniquely susceptible (C.-C. Chang, Y. Chen, K. Modi, O. G. Awar, C. P. Alfrey, and L. Rice. Changes of red blood cell surface markers in a blood doping model of neocytolysis.

*Journal of Investigative Medicine*, 57:650-654, 2009; Rice 2005; M. M. Udden, Pickett M. H. Driscoll, T. B., C. S. Leach-Huntoon, and C. P. Alfrey. Decreased production of red blood cells in human subjects exposed to microgravity. *The Journal of Laboratory and Clinical Medicine*, 125:442-449, 1995).

Neocytolysis is initiated by a fall in erythropoietin levels and in Rice 2005 it was shown that, for instance, low doses of EPO administered to high altitude dwellers on descent, completely abrogated neocytolysis. At the moment it remains unclear whether it is the rate of decline in EPO level or the drop of EPO beneath a certain threshold that acts as a trigger for neocytolysis. (C. P. Alfrey and S. Fishbane. Implications of neocytolysis for optimal management of anaemia in chronic kidney disease. *Nephron Clinical Practice*, 106:149-156, 2007 (hereinafter "Alfrey et al."); Rice 1999).

The current approach to treatment of anemia with ESAs deviates significantly from the normal internal systemic process. Neocytolysis, for instance, contributes to renal anemia. It is precipitated by the pathologic endogenous erythropoietin deficiency of renal disease and the short bursts in EPO concentration followed by sharp declines in serum levels due to administration of the hormone (especially during intravenous (i.v.) administration). It would be desirable to choose dosing schedules such that neocytolysis is minimized or totally prevented. (See Alfrey et al.; Rice 1999). A mathematical model could be very useful to define better administration schemes which stimulate erythropoiesis in a more natural way and abrogate neocytolysis.

Iron and Erythropoiesis

Erythropoiesis is a very complex process and even though erythropoietin is the key regulator, there are other proteins (e.g., interleukins, ...) and substances (e.g., iron, folic acid, vitamin $B_{12}$, ...) that are needed for an optimal erythropoiesis. For instance, one very critical factor for an effective production of red blood cells is iron. The metal is indispensable for hemoglobin synthesis and the hemoglobin protein is the actual oxygen transporter in erythrocytes. The molecule makes up about 97% of the dry weight of red blood cells. If the body is not able to provide sufficient iron for the production of erythrocytes, then impaired erythropoiesis will result. (S. Finch, D. Haskins, and C. A. Finch. Iron metabolism. Hematopoiesis following phlebotomy. Iron as a limiting factor. *The Journal of Clinical Investigation*, 29:1078-1086, 1950; Williams Hematology). In general, a healthy adult has difficulty providing sufficient iron to support production rates greater than three times basal. Higher rates may be possible when administering EPO and iron and in some diseases, e.g. hemochromatosis. (L. T. Goodnough. The role of iron in erythropoiesis in the absence and presence of erythropoietin therapy. *Nephrology Dialysis Transplantation*, 17:14-18, 2002 (hereinafter "Goodnough 2002"); C. A. Finch. Erythropoiesis, erythropoietin, and iron. *Blood. The Journal of American Society of Hematology*, 60(6):1241-1246, 1982) (hereinafter "Finch 1982"). An undersupply of iron additionally leads to an increase in the number of hypochromic RBC. Hypochromic cells (i.e., cells in which the amount of hemoglobin is lower than the normal 26 pg) are small, have a reduced oxygen carrying capacity and are relatively fragile (D. M. Wrighting and N. C. Andrews. Iron Homeostasis and erythropoiesis. *Current Topics in Developmental Biology*, 82:141-159, 2008), and thus are likely to die earlier than normochromic erythrocytes. (A. Loría, L. Sánchez-Medal, R. Lisker, E. De Rodríguez, and J. Labardini. Red cell life span in iron deficiency anaemia. *Br J Haematol*, 13(3):294-302, May 1967).

Erythroid precursor cells are the most avid consumers of iron in the body. (P. Ponka and C. N. Lok. The transferring receptor: role in health and disease. *The International Journal of Biochemistry & Cell Biology*, 31:1111-1137, 1999). The immature erythrocyte has only a few days time to synthesize all the hemoglobin which the mature cell contains. Hemoglobin is a metalloprotein. Its name refers to the special structure. A hemoglobin molecule consists of four subunits each composed of a globular protein embedding a heme group, and every heme group in turn contains one iron atom. Erythroid cells rely completely on transferrin receptors to take up iron. (R. Y. Chan, C. Seiser, H. M. Schulman, L. C. Kuhn, and P. Ponka. Regulation of transferrin receptor mrna expression. distinct regulatory features in erythroid cells. *European Journal of Biochemistry*, 220:683-692, 1994). Contrary to progenitor cells, all types of precursor cells synthesize heme and the increased demand for iron for this process is reflected by a sharp increase in the number of TfR in proerythroblasts. Transferrin receptors reach their peak in intermediate erythroblasts followed by a decrease with further maturation.

In precursor cells heme is essential for maintaining a "normal" number of TfR. Studies showed that inhibition of heme synthesis strongly inhibited TfR expression. It seems that there exists a positive feedback mechanism in which heme promotes a high rate of transferrin receptor synthesis. A high number of transferrin receptors enhances iron uptake and that in turn keeps hemoglobin synthesis at high levels. (P. Ponka. Tissue-specific regulation of iron metabolism and heme synthesis: Distinct control mechanisms in erythroid cells. *Blood*, 89:1-25, 1997). There is evidence that precursor cells which have a low hemoglobin content are still able to proliferate but do not differentiate and undergo apoptosis. (J. A. Schmidt, J. Marshall, M. J. Hayman, P. Ponka, and H. Beug. Control of erythroid differentiation: Possible role of the transferrin cycle. 46:41-51, 1986).

Anemia of Renal Disease

Anemia affects almost all patients with chronic kidney disease. It is caused by failure of renal excretory and endocrine function. It often develops once renal function decreases to 50% and the degree of anemia increases with severity of renal failure. (G. F. Strippoli, J. C. Craig, C. Manno, and F. P. Schena. Hemoglobin targets for the anemia of chronic kidney disease: A meta-analysis of randomized, controlled trials. *Journal of American Society of Nephrology*, 15:3154-3165, 2004). Anemia develops because of deficiency in endogenous erythropoietin production by the kidneys (note that even non functioning kidneys produce some EPO and can maintain hemoglobin levels higher than those found in anephric patients), increased blood losses (gastrointestinal bleeding (purpura, gastrointestinal and gynecologic bleeding occur in one third to one half of all CKD patients (J. B. Wish. Assessing iron status: Beyond serum ferritin and transferring saturation. *Clinical Journal of the American Society of Nephrology*, 1:S4-S8, 2006)), frequent blood sampling, blood left in the dialyzer, multiple vascular access surgeries, ...), functional or absolute iron deficiency and decreased red cell survival. Furthermore, neocytolysis contributes to renal anemia and it explains the often demonstrable hemolytic component and the worsening of hemolysis with more pronounced renal disease. A description of neocytolysis is provided above. It further explains the responsiveness of hemolysis to ESA therapy and the increased efficiency of subcutaneous compared to intravenous therapy, because in s.c. administration nadirs in EPO levels which precipitate neocytolysis are avoided. (See Rice 1999). In general, renal anemia is normocytic and normochromic and the number of reticulocytes is normal or slightly decreased, which is inappropriate in the context of a reduced RBC population. Certain deficiency states, especially iron, but also folate or vitamin $B_{12}$ deficiency may alter the nature of the anemia. (See Finch 1982; M. Polenakovic and A. Sikole. Is erythropoietin a survival factor for red blood cells? *Journal of American Society of Nephrology,* 7:1178-1182, 1996).

Untreated anemia is associated with decreased oxygen delivery to the tissues. For compensatory reasons, cardiac output increases, resulting in left ventricular hypertrophy. Cardiac disease is the most common cause of death among patients who are on maintenance dialysis. Partial correction of anemia in these patients was shown to reduce cardiac ischemia and ameliorate cardiomegaly, thus, reducing cardiac related morbidity. (A. Besarab, W. K. Bolton, J. K. Browne, J. C. Egrie, A. R. Nissenson, D. M. Okamoto, S. J. Schwab, and D. A. Goodkin. The effects of normal as compared with low hematocrit values in patients with cardiac disease who are receiving hemodialysis and epoetin. *The New England Journal of Medicine,* 339:584-590, 1998). Further consequences of uncorrected anemia are decreased cognition and mental acuity and overall decrease in patient welfare.

ESA Therapy

Erythropoiesis stimulating agents have been used to treat anemia in patients suffering from chronic renal failure for more than two decades. Optimal hemoglobin targets are still a matter of discussion. Studies have shown (see e.g. Singh et al.; Strippoli et al.; R. N. Foley, B. M. Curtis, and P. S. Parfrey. Erythropoietin therapy, hemoglobin targets, and quality of life in healthy hemodialysis patients: A randomized trial. *Clinical Journal of the American Society of Nephrology,* 4:726-733, 2009 (hereinafter "Foley et al.")) that a partial correction of anemia is preferable to a full correction. A number of complications can occur in patients with CKD when they have near-normal/normal hemoglobin levels, i.e., higher vascular access thrombosis, hypertension and greater requirements for antihypertensives, cardiovascular events, earlier need for renal replacement therapy and higher mortality. Normal hemoglobin levels for women are in a range of between about 12 g/dl and 16 g/dl, and in a range of between about 13 g/dl and about 17.5 g/dl for men.

Defining an optimal hemoglobin target is not the only issue regarding ESA therapy. Another problem is: how can the target hemoglobin be achieved and how to keep the patient near this hemoglobin level over a long time period? The dose and frequency of administration of an ESA treatment regimen are most often determined based on the prior experience of the physician and on established guidelines. This approach bears some limitations and level of hemoglobin tends to fluctuate greatly and cycling phenomena are observed. An analysis of 31,267 patients on hemodialysis in the Fresenius Medical Care-North America database found that only 5% of patients persistently remained within a desired Hb range of 11-12 g/dl for a period of 6 months. (A. J. Collins, R. M. Brenner, J. J. Ofman, E. M. Chi, N. Stuccio-White, M. Krishnan, C. Solid, N. J. Ofsthun, and J. M. Lazarus. Epoetin alfa use in patients with esrd: an analysis of recent us prescribing patterns and hemoglobin outcomes. *American Journal of Kidney Diseases,* 46:481-488, 2005) (hereinafter "Collins et al."). Fishbane et al. ((S. Fishbane and J. S. Berns. Hemoglobin cycling in hemodialysis patients treated with recombinant human erythropoietin. *Kidney International,* 68:1337-1343, 2005)) analyzed data of dialysis patients collected over five years in a hospital and came to a similar conclusion. More than 90% of the patients experienced hemoglobin cycling. The authors state that changes in ESA dose were the most important driver and were associated with hemoglobin excursion in about 80% of cases. The ESA dose adjustment protocol that was used was similar to the protocol used in most dialysis centers (see Tables A1-A8 for an example of a typical dose adjustment protocol).

Therapy with ESAs is quite different than biological erythropoietin secretion. In hemodialysis patients, i.v. administration route is primarily used, because of the availability of venous access. Intravenous treatment involves short, intermittent, non-physiologic bursts of EPO concentration. The bursts are followed by a fast decline to very low levels of EPO. These fluctuations in plasma concentration do not coincide, either temporally or in magnitude, with physiologic perturbations. Therefore, it may not be surprising that Hb levels fluctuate widely and that it is extremely difficult for physicians to adjust dosing schemes such that no cycling phenomena occur. Note that fluctuations in hemoglobin result in varying oxygen delivery to vital organs. Consequences include repeated episodes of relative ischemia and compensatory mechanisms in organs (e.g. heart) that may result in disordered growth signals, pathologic organ function and worsened patient outcomes. (See Fishbane et al.).

A predictive model of erythropoiesis can help deal with this situation. For instance, a physician can try different ESA treatment regimens and observe their effects on hemoglobin levels over the next few months. Dosing regimens can be tested/chosen with regard to avoidance of neocytolysis, minimal amounts of ESA administered and avoidance of cycling patterns in Hb concentration.

Iron Therapy

Patients with anemia of chronic kidney disease have to be followed for symptoms of iron deficiency. (J. W. Fisher. Erythropoietin: Physiology and pharmacology update. *Experimental Biology and Medicine,* 28:1-24, 2003). 80-90% of dialysis patients on ESA therapy will require iron at some stage. (R. M. Schaefer and L. Schaefer. Iron monitoring and supplementation: How do we achieve the best results? *Nephrology Dialysis Transplantation,* 13:9-12, 1998). This very pronounced need for supplementary iron has different reasons. On one hand iron stores can be depleted (absolute iron deficiency). Iron loss in hemodialysis patients (due to continuous gastrointestinal, purpural and gynecological bleeding, frequent blood sampling, surgeries, . . . ) is about 1500-3000 mg/year, as compared to iron loss for a healthy adult that is about 400-800 mg/year, and can be even higher under certain circumstances. Hence, the daily need for iron can be well above the absorptive capacity of the intestinal. This is aggravated by the fact that the uptake via the duodenum is often impaired in these patients. On the other hand, a functional iron deficiency is often observed in renal anemia. During ESA therapy, the number of erythroid progenitor and precursor cells in the bone marrow increase drastically and this imposes a lot of stress on systemic iron homeostasis. Supply and demand often do not match. It is difficult, even for healthy persons, to increase the rate at which iron is released from stores and is recycled from hemoglobin to deliver enough iron to the bone marrow to keep up with supraphysiologic rates of RBC production during ESA treatment. Matters are further complicated in chronic kidney disease because of inflammation, which frequently occurs with various degrees of severity. Thus, iron utilization is regularly decreased in renal insufficiency. See above for a detailed description of the effects of inflammation on systemic iron homeostasis.

In the pre-ESA era iron overload, because of successive blood transfusions, was a major cause of morbidity in dialysis patients. Its significance in the post-EPO era remains unclear. (K. Kalantar-Zadeh, D. L. Regidor, C. J. McAllister, B. Michael, and Warnock D. G. Time-dependent associations between iron and mortality in hemodialysis patients. *Journal of American Society of Nephrology*, 16:3070-3080, 2005). A continuous administration of i.v. iron certainly results in overfilled iron-stores and imposes serious health risks. Hence, decisions on when to supply the patient with i.v. iron and when to withdraw therapy have to be thoroughly evaluated. A mathematical model can help keep track of the current iron status of a patient and can help to make decisions on adaptations of treatment.

Finally, there is a very complex interaction between hemoglobin cycling and iron storage whose dynamical behavior under ESA and iron treatment, even for an experienced physician, is barely predictable. In Alfrey et al., the authors suggest that: "[ . . . ] the current therapeutic paradigm of hemoglobin monitoring, iron treatment, and rHuEPO treatment results in recurrent nonphysiologic cycling of hemoglobin levels in hemodialysis patients."

Mathematical Model of Erythropoiesis in an Adult

The model developed below focuses on the effects of erythropoietin on erythroid cells. Hence, throughout this development, an impairment of erythropoiesis because of an under supply with iron is ruled out. Despite this limitation, the mathematical model developed in this chapter is applicable for a number of different situations, as long as it is reasonable to assume that erythropoiesis is sufficiently supplied with iron. For instance, the model presented here is able to describe the recovery of red cell mass after blood donation, the reaction of the body to presurgical administration of ESAs and changes in the number of erythrocytes of polycythemic high altitude dwellers descending to sea level. This model is only applicable for a small subpopulation of dialysis patients. If iron deficiency is treated by administering iron, and therefore erythropoiesis is sufficiently supplied with it, the model can be applied to a larger subgroup of dialysis patients. Furthermore, this model helps to understand the most important dynamics that need to be considered for red blood cell production.

The model is based on structured population models describing the different erythroid cell stages. Five different population classes of cells are considered: BFU-E, CFU-E, erythroblasts, marrow reticulocytes and mature erythrocytes circulating in the bloodstream (including peripheral reticulocytes). Individual cells are distinguished according to their maturity, which can also be referred to as cell age. The commitment to the erythroid lineage is an irreversible event. A differentiated cell cannot regress or switch into another differentiation pathway. Thus, once a multipotent stem cell is committed to the erythroid lineage, it undergoes the complete series of differentiations until it becomes a mature red blood cell, or it dies eventually during this process. While maturing the cell divides a number of times. Hence, age-structured population models of the form $$\frac{\partial}{\partial t} u(t, \mu) + v(E(t)) \frac{\partial}{\partial \mu} u(t, \mu) = (\beta - \alpha(E(t), \mu)) u(t, \mu),$$

are used in order to describe the development of the cell populations. Here u(t, μ) denotes the population density of the cell population at time t with maturity μ. Further, β(•) and α(•) describe the proliferation rate and rate of apoptosis, respectively, of the cells. The function α(•) a priori depends on the maturity μ and the concentration of EPO E(t), respectively, at time t. The function v describes the maturation velocity and depends on the concentration E(t).

For the different population classes, the characteristic properties (proliferation rate, rate of apoptosis and maturation velocity) change depending on erythropoietin, because while maturing the cell changes its morphological characteristics, such as, the number of EPO- and transferrin-receptors expressed on the surface.

In the following sections, the assumptions that were made for the different population classes are listed, briefly described and the mathematical equations that arise in consequence are stated.

Progenitor Cells: BFU-E and CFU-E Cells

Assumptions:
1. The number of cells, which commit to the erythroid lineage, is constant.
2. Cells normally stay in this stage for 13 days (7 days BFU-E and 6 days CFU-E).
3. EPO has no effect on the number of divisions or the rate of apoptosis of BFU-E.
4. The proliferation rate of CFU-E cells is constant,
5. whereas the rate of apoptosis depends highly on EPO levels.
6. The maturation velocities of BFU-E and CFU-E cells are constant.

The process by which stem cells are recruited into proliferating progenitor population remains unclear. There are several hypotheses including an environmental dependency, that it is a random event, etc. For the moment the inventors assume that the number of stem cells entering the erythroid lineage is independent of EPO and thus constant. The change in population of the progenitor cells over time are described considering two different classes of cells: namely BFU-E and CFU-E cells.

The earliest identifiable erythroid progenitor cell is the Burst-forming Unit Erythroid (BFU-E). At first, these cells express only a very small number of EPO receptors on the surface. (See Wintrobe's Clinical Hematology). Thus, it is reasonable to assume EPO has no effect on proliferation or apoptosis of these cells. (See Wu et al.). In culture it lasts around 6-7 days until human BFU-E have all the functional characteristics of the next cell stage—called CFU-E (Colony-forming Unit Erythroid) (See Williams Hematology) (Assumption 2). Morphologically it is difficult to distinguish between those two types of cells because there are cells in between these two developmental stages which show characteristic properties between BFU-E and CFU-E. Therefore, a distinction is valid but artificial.

The BFU-E cell class is described by the following population equation $$\frac{\partial}{\partial t} p(t, \mu^p) + \frac{\partial}{\partial \mu^p} p(t, \mu^p) = \beta^p p(t, \mu^p), \quad (1)$$

$$p(t, 0) = S_0,$$

$$p(0, \mu^p) = p_0(\mu^p),$$

where p(t, $\mu^p$) is the population density of the cell class at time t with maturity $\mu^p$, $0 \leq \mu^p \leq \mu^p_{max} = 7$, t>0. Further, $\beta^p$ is a constant proliferation rate and $\alpha^p \equiv 0$ (Assumption 3), $S_0$ describes the number of cells committing to the erythroid lineage (Assumption 1) and $p_0$ ($\mu^p$) is the population density at t=0.

Once a cell reaches the maximum age for BFU-E cells, it leaves this population class and enters the CFU-E class. Consequently, there is a continual flux of cells from one population class to the next one. CFU-E are more rapidly dividing cells than BFU-E. (See Wu et al.). During this stage, cells are very sensitive to EPO levels and under normal conditions large numbers of generated CFU-E are not surviving. (See Wintrobe's Clinical Hematology). CFU-E are highly dependent on EPO to prevent them from apoptosis, i.e., the mortality for this population class depends on the EPO concentration. Altogether, the following equations for the second class are obtained:

$$\frac{\partial}{\partial t}q(t,\mu^q) + \frac{\partial}{\partial \mu^q}q(t,\mu^q) = (\beta^q - \alpha^q(E(t)))q(t,\mu^q), \quad (2)$$

$$q(t, \mu^q_{min}) = p(t, \mu^p_{max}),$$

$$q(0, \mu^q) = q_0(\mu^q),$$

where $q(t, \mu^q)$ is the population density of the CFU-E class at time t with maturity $\mu^q$, t>0 and $7=\mu^q_{min} \leq \mu^q \leq \mu^q_{max}=13$. Further on, $\beta^q$ stands for a constant proliferation rate (Assumption 4), $\alpha^q(E(t))$ denotes the apoptosis rate depending on the EPO-concentration (Assumption 5), $q(t, \mu^q_{min})=p(t, \mu^p_{max})$ describes the number of cells leaving the BFU-E cell stage and entering the CFU-E cell stage and $q_0(\mu^q)$ is the population density at t=0.

A sigmoid function is used to describe the rate of apoptosis, $$\alpha^q(E(t)) = \frac{a_1 - b_1}{1 + e^{k_1 E(t) - c_1}} + b_1 \quad (3)$$

where E(t) is the EPO concentration at time t and $a_1$, $b_1$, $c_1$ and $k_1$ are positive constants and $a_1 > b_1$. The function $\alpha^q$ monotonically decreases with increasing EPO concentration. Thus, a higher level of EPO causes more cells to survive.

Note, because of Assumption 6 the inventors can define $v^p = v^q \equiv 1$, for all t≥0, and thus, the maturity or cell age of progenitor cells, respectively, actually coincides with the age of the cell.

Precursor Cells: Erythroblasts and Marrow Reticulocytes
Assumptions:
7. Cells stay in this stage for 6-8 days (5 days erythroblasts and 1-3 days marrow reticulocytes).
8. The class erythroblasts consists of all cell stages from proerythroblast to orthocromatophilic erythroblast.
9. EPO has no effect on the number of divisions or the rate of apoptosis of erythroblasts. The proliferation rate of erythroblasts is assumed to be constant.
10. The maturation velocity of erythroblasts is constant.
11. Reticulocytes mature but do not proliferate.
12. The maturation velocity of reticulocytes depends on EPO.
13. A constant portion of marrow reticulocytes is phagocytosed.

After a CFU-E differentiates to a proerythroblast, it takes about another 6-8 days until the cell is released from the bone marrow into the bloodstream. (See Jandl). The various stages of maturation from proerythroblast to orthochromatophilic erythroblast (see FIG. 1B) are referred to as erythroblasts. The cells undergo several mitotic divisions until at the stage of orthochromatophilic erythroblast they lose their ability to divide and enter a maturation period. The erythroblastic pyramids appear normal, with no evidence of additional mitotic divisions, when production increases, i.e., the inventors assume proliferation of erythroblasts to be independent of EPO levels and define it to be constant. See Williams Hematology.

Hence, the erythroblast class can be described by the following equation $$\frac{\partial}{\partial t}r(t,\mu^r) + \frac{\partial}{\partial \mu^r}r(t,\mu^r) = \beta^r r(t,\mu^r), \quad (4)$$

$$r(t, \mu^r_{min}) = q(t, \mu^q_{max}),$$

$$r(0, \mu^r) = r_0(\mu^r),$$

where $r(t, \mu^r)$ is the population density of the erythroblasts at time t with maturity $\mu^r$, t>0 and $13=\mu^r_{min} \leq \mu^r \leq \mu^r_{max}=18$. Further, $\beta^r$ is a constant proliferation rate and $\alpha^r \equiv 0$ (Assumption 9), the maturation velocity $v^r \equiv 1$ (Assumption 10), $r(t, \mu^r_{min})=q(t, \mu^q_{max})$ describes the number of cells leaving the CFU-E stage and entering the erythroblasts cell stage and $r_0(\mu^r)$ is the population density at t=0.

The differentiating process from orthochromatophilic erythroblasts to marrow reticulocytes involves the extrusion of the cell nucleus. Reticulocytes are not capable of cell divisions (Assumption 11), i.e., $\beta^s \equiv 0$. In this model, the inventors do not account for an impaired erythropoiesis due to iron deficiency. Still, even when the erythroid cells in the bone marrow are sufficiently supplied with iron, not all precursor cells survive. Some of the reticulocytes die before they are released to the blood stream. (G. Barosi, M. Cazzola, C. Berzuini, S. Quaglini, and M. Stefanelli. Classification of anemia on the basis of ferrokinetic parameters. *British Journal of Haematology*, 61:357-370, 1985; M. Stefanelli, D. P. Bentley, I. Cavill, and H. P. Roeser. Quantitation of reticuloendothelial iron kinetics in humans. *The American Journal of Physiology*, 247:842-849, 1984). This is why Assumption 13 is made.

A raised EPO concentration shortens the marrow transit time of precursor cells. If the EPO level is elevated marrow reticulocytes are released prematurely. The inventors account for this by allowing the maturation velocity of reticulocytes to vary depending on erythropoietin concentration. Thus, although the maximum cell age of marrow reticulocytes is fixed the actual transit time for the cells varies between 1-3 days. Hence, the transit time for precursor cells is between 6-8 days (Assumption 7).

The population equation referring to marrow reticulocytes is $$\frac{\partial}{\partial t}s(t,\mu^s) + v^s(E(t))\frac{\partial}{\partial \mu^s}s(t,\mu^s) = -\alpha^s s(t, \mu^s), \quad (5)$$

$$v^s(E(t))s(t, \mu^s_{min}) = r(t, \mu^r_{max}),$$

$$s(0, \mu^s) = r_0(\mu^s),$$

where $s(t, \mu^s)$ is the reticulocytes population density at time t with maturity $\mu^s$, t>0 and $18=\mu^s_{min} \leq \mu^s \leq \mu^s_{max}=20$. Further on, $v^s$ is the maturation velocity depending on EPO (Assumption 12), $\alpha^s$ denotes the rate with which reticulocytes are phagocytosed (Assumption 13), $v^s(E(t))s(t, \mu^s_{min})=r(t,$ $\mu_{max}{}^r$) describes the number of cells leaving the erythroblast cell stage and entering the reticulocyte cell stage, $r_0(\mu^s)$ is the population density at t=0.

A sigmoid function is used to describe the changes in maturation velocity $v^s$, $$v^s(E(t)) = \frac{a_2 - b_2}{1 + e^{-k_2 E(t) + c_2}} + b_2, \quad (6)$$

where E(t) is the EPO concentration at time t and $a_2$, $b_2$, $c_2$ and $k_2$ are positive constants with $a_2 > b_2$. The maturation velocity increases with a rising concentration of EPO. Note, a slower maturation velocity causes the cells to reach the maximum cell age $\mu^s_{max}$ at a later point, whereas a faster maturation velocity shortens the transit time, i.e., the cells reach $\mu^s_{max}$ earlier.

Erythrocytes

Assumptions:

14. Erythrocytes and blood reticulocytes are subsumed in one class.
15. Cells mature but do not proliferate.
16. There is a fixed random daily break-down of red blood cells (not to be confused with loss of erythrocytes due to senescence).
17. A drop in EPO concentration beneath a threshold precipitates neocytolysis.
18. Erythrocytes with age between 14-21 days are likely to be affected by neocytolysis.
19. Cells are phagocytosed when they reach the maximum age.
20. The maximum age of erythrocytes in a healthy person is 120 days.

The reticulocytes are released from the bone marrow into the blood stream and within 1-2 days they mature to erythrocytes. Circulating red blood cells have no nuclei and therefore they are not able to proliferate and they are not able to repair themselves. Thus, the life span of these cells is limited. In healthy adults the average life span is about 120 days (see e.g., Jandl), but it can significantly shorten in some pathologies. If not otherwise stated the inventors use 120 days to be the maximal age of erythrocytes for the model. Cells can be lost for different reasons:

due to internal or external bleeding,
because of random daily-breakdown,
because neocytolysis is triggered,
and last but not least, because of eryptosis of senescent cells.

Altogether, the following equation is obtained for red blood cells:

$$\frac{\partial}{\partial t} m(t, \mu^m) + \frac{\partial}{\partial \mu^m} m(t, \mu^m) = -\alpha^m(E(t), \mu^m) m(t, \mu^m), \quad (7)$$

$$m(t, 0) = v^s(E(t)) s(t, \mu^s_{max}),$$

$$m(0, \mu^m) = m_0(\mu^m),$$

where $m(t, \mu^m)$ is the population density for the erythrocyte class at time t with maturity $\mu^m$, t>0 and $0 = \mu^m_{min} \leq \mu^m \leq \mu^m_{max} = 120$ (Assumption 20). Moreover, $m(t, 0) = v^s(E(t)) s(t, \mu^s_{max})$ describes the number of reticulocytes entering the blood stream and $m_0(\mu^m)$ is the population density at t=0. In the population equation $\alpha^m(E(t), \mu^m)$ denotes a random daily break-down and neocytolysis $$\alpha^m(E(t), \mu^m) = \quad (8)$$

$$\begin{cases} \gamma^m(\mu^m) + \min\left(\frac{c_E}{E(t)^{k_E}}, b_E\right) & \text{for } E(t) < \tau_E, \mu_{min}^{m,n} \leq \mu^m \leq \mu_{max}^{m,n} \\ \gamma^m(\mu^m) & \text{otherwise,} \end{cases}$$

where $b_E$, $c_E$, $k_E$ are positive constants, $\tau_E$ is the threshold beneath which neocytolysis is triggered (Assumption 17), and $[\mu_{min}^{m,n}, \mu_{max}^{m,n}] = [14, 21]$ (Assumption 18) is the age interval during which cells are affected by neocytolysis, and $t \geq 0$. Since it is assumed that a cell is phagocytosed when it reaches its maximum age (Assumption 19), the mortality rate $\gamma^m(\mu^m)$ to be chosen such that $\gamma^m(\mu^m) = \alpha^m_{rand}$ for $\mu_{min}^m \leq \mu^m \leq \mu_{max}^m - \delta$ with $\delta > 0$ sufficiently small and $\int_{\mu_{max}-\delta}^{\mu_{max}^m} \gamma^m(\mu^m) = \infty$. Here $\alpha^r_{rand}$ is a random daily breakdown (Assumption 16). A possible choice for $\gamma^m(\mu^m)$ is $$\gamma^m(\mu^m) =$$

$$\begin{cases} \alpha^m_{rand} & \text{for } \mu^m \in [\mu^m_{min}, \mu^m_{max} - \delta] \\ \frac{3\alpha^m_{rand}\delta^2}{(\mu^m)^2 - 2(\mu^m_{max} + \delta)\mu^m + (\mu^m_{max} + 2\delta)\mu^m_{max}} & \text{for } \mu^m \in [\mu^m_{max} - \delta, \mu^m_{max}] \\ \infty & \text{for } \mu^m \geq \mu^m_{max} \end{cases}$$

Additionally, it is possible to add a further term $\alpha_{bleed}^m(t)$ to the mortality rate in case of bleeding.

Erythropoietin

Assumptions:

21. Release of EPO is controlled by a negative feedback mechanism according to the oxygen content.
22. Oxygen carrying capacity is directly proportional to the number of erythrocytes.
23. The degradation rate of EPO is constant.
24. There is a slight delay in reaction of the EPO production rate to the number of RBC but this is negligible compared to the duration of development of erythrocytes.

The kidneys adjust the release of EPO according to the oxygen carrying capacity of the blood. If blood oxygen content is lower than normal, then EPO production increases and vice versa. Thus, the production of EPO is controlled by a negative feedback mechanism and allows for more red blood cells to be developed in case of an undersupply of the body with oxygen by opposing programmed cell death of erythroid progenitor cells. Additionally, if EPO decreases beneath a certain threshold, neocytolysis is triggered, the process wherein macrophages start to phagocytose young erythrocytes (neocytes).

A sigmoid function which depends on blood oxygen partial pressure is used to model the feedback involving the release of erythropoietin $E_{in}^{end}(t)$ from the kidneys into plasma. As a consequence of Assumption 22 the amount of $E_{in}^{end}(t)$ of EPO released by the kidney per unit time can be directly computed by use of the total population of erythrocyte M(t). Recall that this class consists of all circulating red blood cells (Assumption 14):

$$E_{in}^{end}(t) = \frac{a_3 - b_3}{1 + e^{k_3 \tilde{M}(t) - c_3}} + b_3,$$

where $\tilde{M}(t) = 10^{-8} M(t)/TBV$ is a scaled erythrocytes "concentration". Note, that $M(t) = \int_0^{\mu_{max}^m} m(t, \mu^m) d\mu^m$ and TBV is the total blood volume. The constants $a_3$, $b_3$, $c_3$, $k_3$ are positive and satisfy $a_3>b_3$. The function $E_{in}^{end}$ (t) is monotonically decreasing. Thus, the release of EPO increases if the number of circulating red blood cells decreases (Assumption 21). The dynamics of the endogenous EPO concentration $E^{end}(t)$ in plasma are described by the following ordinary differential equation:

$$\frac{d}{dt}E^{end}(t) = \frac{1}{TBV}E_{in}^{end}(t) - c_{deg}^{end}E^{end}(t),$$

where $E^{end}(t)$ is the endogenous EPO concentration in plasma, $E_{in}^{end}$ is the amount of EPO released by the kidneys and $c_{deg}^{end}$ describes the constant degradation rate of endogenous EPO (Assumption 23).

The degradation rate for exogenous EPO $c_{deg}^{ex}$ differs from the one for endogenous EPO and varies according to the kind of ESA administered. Therefore, an additional ODE is needed to describe the change in the plasma concentration of an ESA $$\frac{d}{dt}E^{ex}(t) = \frac{1}{TBV}E_{in}^{ex}(t) - c_{deg}^{ex}E^{ex}(t),$$

where $E_{in}^{ex}$ (t) is the rate at which the artificial hormone is administered and $c_{deg}^{ex}$ is the rate with which the exogenous hormone is degraded. In intravenous administration, the total amount of the agent is injected into a vein, within a very short time interval. In this case $E_{in}^{ex}(t)$ can be approximated by $E_0^{ex}(t)\delta_{t_0}(t)$, where $E_0^{ex}$ is the amount of artificial hormone administered and $\delta_{t_0}(t)$ is the Dirac delta impulse located at $t_0$, the time when the administration takes place. The overall concentration of EPO in blood consists of the naturally produced erythropoietin in the body and the administered ESA $$E(t)=E^{ex}(t)+E^{in}(t).$$

Revisited Model

The model assumptions and equations changed a number of times during the modeling process. Extensive discussion with physicians and molecular biologists resulted in adaptions of existing assumptions and adding of new ones. Some modeling ideas were incorporated in the model and kept, others were scrapped after some test simulations. The model presented above, is the version with which almost all simulations below were done.

Some assumptions were revisited very recently and had not been included in the simulations presented below. Nevertheless, for the sake of completeness the changes made are listed here.

Assumptions revisited:
25. The number of cells which commit to the erythroid lineage, is EPO dependent.
26. Cells normally stay in this stage for 8 days (3 days BFU-E and 5 days CFU-E).
27. Under high levels of EPO, stress reticulocytes are released.

It is recommended to change Assumption 1 and 2 to Assumption 25 and 26. The number of stems cells which become BFU-E cells per unit time can then be described by a sigmoidal function $$S_0(t) = \frac{a_4-b_4}{1+e^{-k_4 E(t)+c_4}}+b_4,$$

where E(t) is the EPO concentration and $a_4$, $b_4$, $c_4$ and $k_4$ are constants. Note, the inventors define $a_4=1.2b_4$, because there is evidence that the maximum stem cell increase can be by about 20%. Assumption 26 implies that the cell age ranges for progenitor cells have to be changed to $\mu_{max}^p=\mu_{min}^q=3$ and $\mu_{max}^q=8$. Further Assumption 27 should be added to the list of assumptions for precursor cells above. This assumption can be understood as follows: when the EPO concentration increases above a certain threshold $\tau_s$ the whole reticulocyte population class is released to the bloodstream and the class is skipped, i.e., cells that mature to marrow reticulocytes are immediately released from the bone marrow, as long as EPO levels remain above the threshold.

Computation of Hematocrit and Hemoglobin Concentrations

In order to compute the hematocrit (HCT) and the hemoglobin concentration (Hb) for a subject from the model output (which is the number of red blood cells circulating in blood), estimates of the total blood volume of the subject are needed. The Nadler and Allen formula (see Nadler, S. B., Hidalgo, J. U., and Bloch, T., Prediction of blood volume in normal human adults, Surgery, 1962, Vol. 51, pp. 224-232) can be used to estimate the total blood volume (TBV) of a healthy subject according to her/his weight and height:

♀: TBV[ml]=183.3+356.1×(height[m])³+33.08× weight[kg],

♂: TBV[ml]=604.1+366.9×(height[m])³+32.19× weight[kg].

The TBV for a dialysis patient can be measured by radiolabeling red blood cells with chromium-51 as described above. Using these estimates for the total blood volume, the hematocrit (HCT) and the hemoglobin concentration (Hb) can be computed for a patient from the number of red blood cells circulating in blood via the following formulae:

$$HCT[\%] = \frac{(M(t) \times MCV[fl])}{TBV[ml]},$$

where $M(t)=\int_0^{\mu_{max}^m} m(t, \mu^m)d\mu^m$ is the total number of erythrocytes circulating in blood and MCV is the mean corpuscular volume of a RBC which is obtained from measurement, and $$Hb\left[\frac{g}{l}\right] = 1000 \times \frac{M(t) \times MCH[pg]}{TBV[ml]},$$

where MCH is the mean cellular hemoglobin, which is also obtained via measurements.

Implementation in a Computer Network

Figure 17:
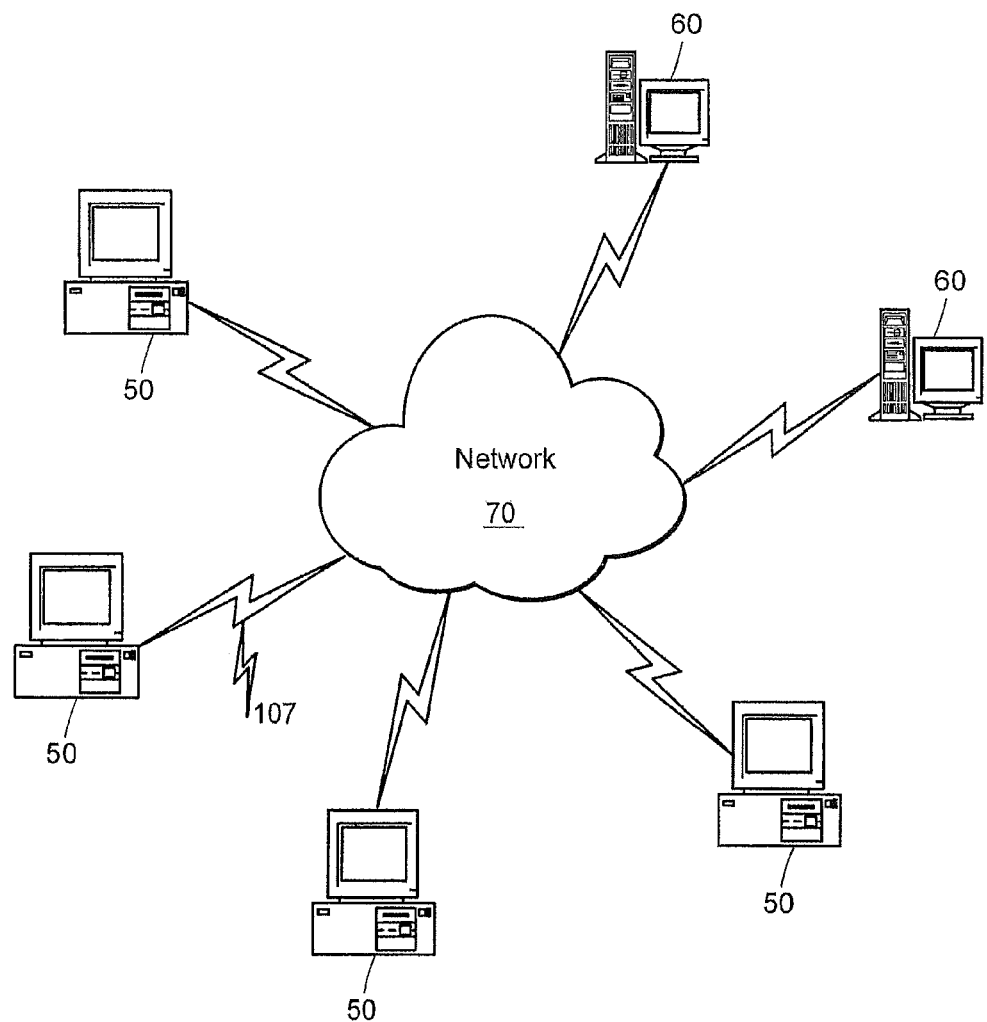
FIG. 17 is a schematic view of a computer network in which the present invention may be implemented.

FIG. 17 illustrates a computer network or similar digital processing environment in which the present invention may be implemented.

Computer(s)/devices 50 and server computer(s) 60 provide processing, storage, and input/output devices executing application programs and the like. Computer(s)/devices 50 can also be linked through communications network 70 to other computing devices, including other devices/processes 50, digital processor dialysis machines 50A, and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 18:
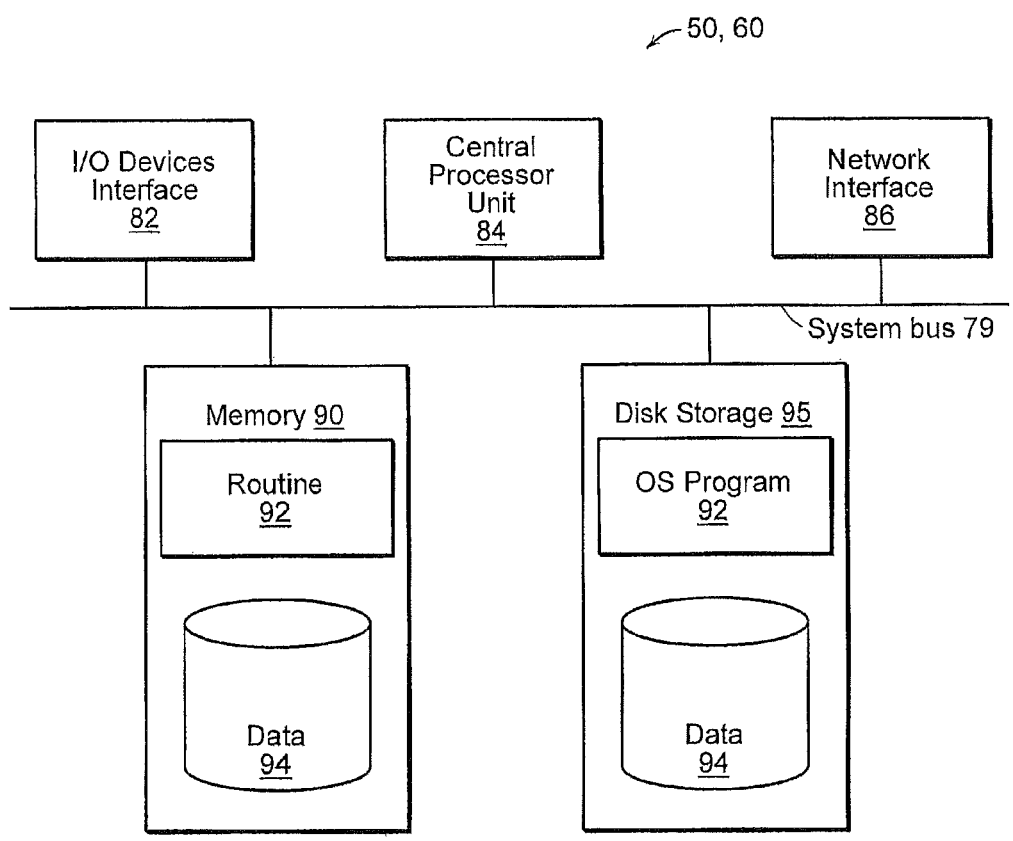
FIG. 18 is a block diagram of a computer of the network of FIG. 17.

FIG. 18 is a diagram of the internal structure of a computer (e.g., processor/device 50, digital processor dialysis machines 50A, or server computers 60) in the computer system of FIG. 17. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 17). Memory 90 provides volatile storage for computer software instructions 92 and data 94 used to implement an embodiment of the present invention (e.g., Eqs. shown in FIG. 3 or any other erythropoiesis modeling engine detailed above). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

EXEMPLIFICATION

The erythropoiesis model, presented here, consists of five partial differential equations (PDEs), several ordinary differential equations (ODEs) and some auxiliary equations which determine the dynamics and the feedback of the system. Altogether there are 30 parameters to which values have to be assigned. In general, the parameters of a model are estimated using data measured in the system. It is important to have measurements for different outputs and during situations where the system is perturbed in some way, because measurements taken in a "steady state", in general, contain very little information. Further requirements to do a proper parameter identification are that measurements are taken with a certain frequency, i.e., there have to be enough data points, and that the measurements are of a certain quality, i.e., the measurement error should be small. If these conditions are satisfied, it is possible to estimate (some of) the parameters of the model using mathematical routines and to properly validate the model. Unfortunately, in physiology, mathematicians and engineers normally face very bad data situations. In general, data is scarce, only very few things can be measured and the quality of the measurements is often not satisfying. Thus, parameter identification itself poses very interesting mathematical problems in these situations and is subject to current research and constantly developed.

In the course of this work, parameter identification was not used to estimate model parameters. However, to run simulations one needs to assign values to the parameters. Thus, literature values were used to make a first educated guess of the parameters of the models. For instance, the inventors found in Williams Hematology a table of the erythroid pools in adults. In this book the number of different erythroid cell types for a healthy adult per kg body weight are given. The cell populations for a 75 kg male adult were calculated according to this table and used to estimate the model parameters for the steady state. For a list of the calculated values see Table 1. In addition, some other considerations were also used, as for instance, the fact that in a healthy adult, the production rate can increase about 3-fold and that, by providing drugs (ESAs and iron), this can further increase to about 5-fold. (See Goodnough 2002; Finch 1982). The parameter values used for the simulations are listed in the corresponding sections.

TABLE 1

Number of different erythroid cell types in a healthy adult

| Cell Type | Observed ($\times 10^8$/kg) | 75 kg |
|---|---|---|
| Proerythroblasts | 1 | $75 \times 10^8$ |
| Erythroblasts | 49 | $36.75 \times 10^{10}$ |
| Marrow Reticulocytes | 82 | $61.5 \times 10^{10}$ |
| Red Blood Cells (incl. blood reticulocytes) | 3331 | $24.98 \times 10^{12}$ |

Simulations of Concrete Real Situations

In this section outputs of the model for different situations are compared to data found in literature. Particular attention is paid that the model is only used to simulate situations for which it is feasible, i.e., situations were it can be assumed that iron supply of erythropoiesis is sufficient.

Figure 5A:
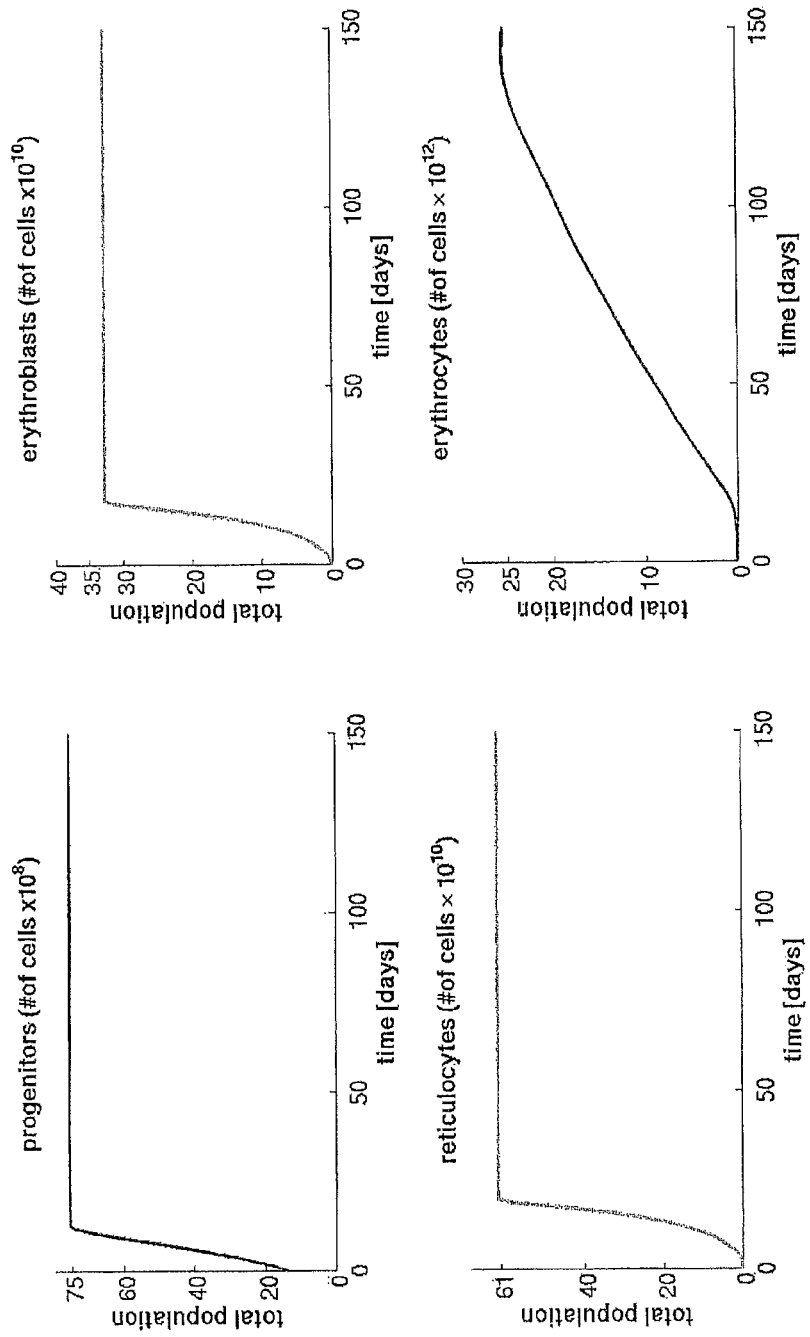
FIG. 5A sets forth graphs of simulations with the model of this invention for a hypothetical 75 kg male starting with $1 \times 10^8$ cells and with feedback control not taken into account.
Figure 5B:
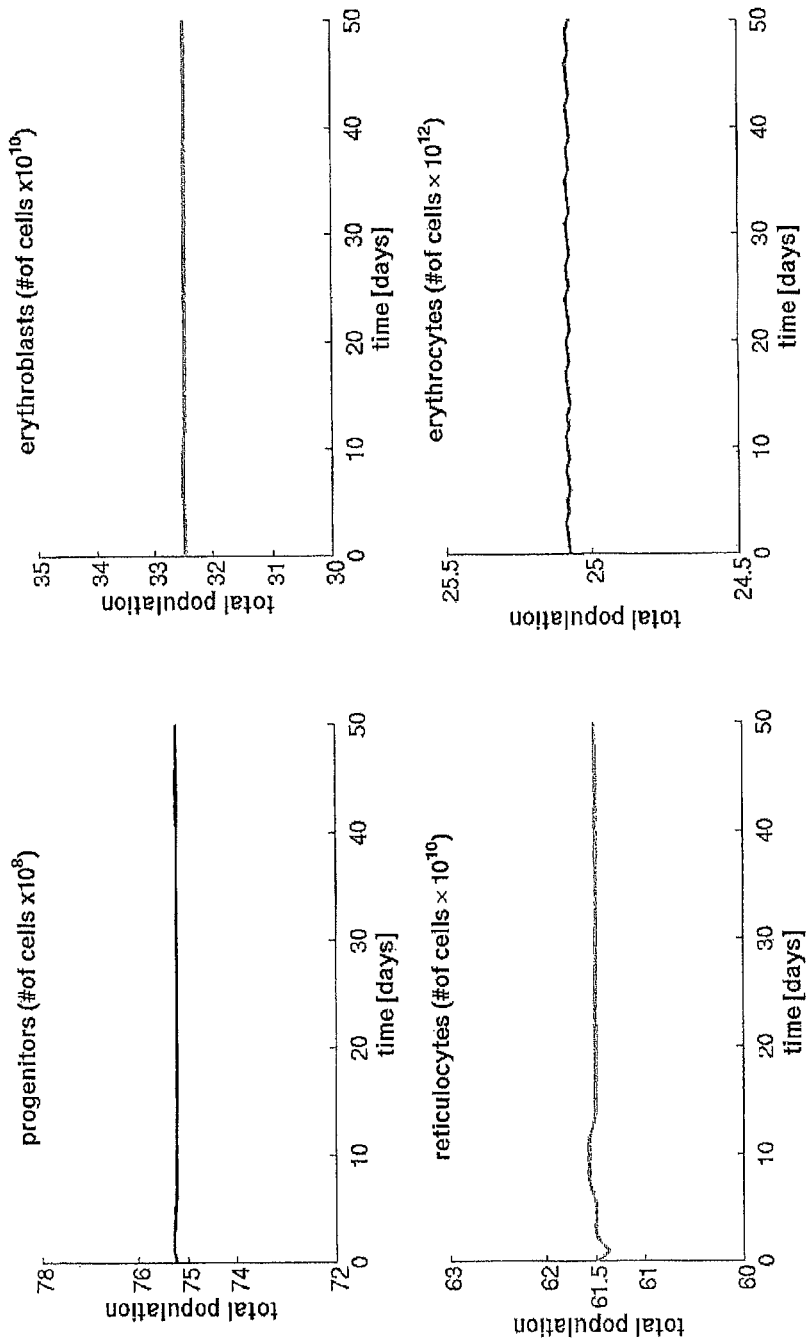
FIG. 5B sets forth graphs of simulations with the model of this invention for a hypothetical 75 kg male starting near the equilibrium with feedback control taken into account.
Figures 2, 5C:
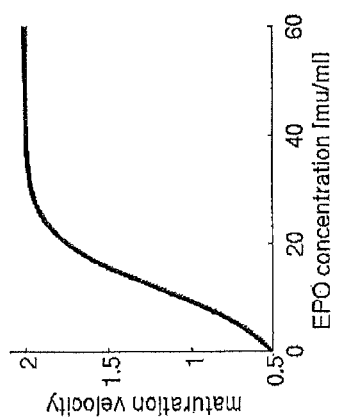
Figures 1, 5C:
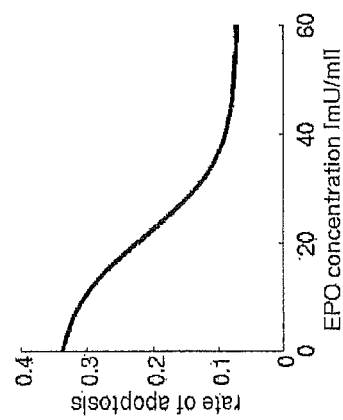

We start by trying to simulate the steady state situation in a healthy adult using the model, i.e., iron is not considered to be a limiting factor for erythropoiesis and the feedback is turned off. The inventors guessed the parameters according to the method previously described. Plots of the model output are presented in FIG. 5A. Each cell population is started with $1 \times 10^8$ cells, therefore, the model needs some time to reach its equilibrium. Satisfied with the performance of the model in the steady state, the parameters for the feedback rule and the auxiliary equations were set. The values were chosen such that solutions stay near the desired equilibrium, when started near the steady state, and that the solutions always tend to the steady state, as shown in FIG. 5B. In FIG. 5C plots for the three sigmoidal functions (FIGS. 5C-1, 5C-2, and 5C-3) describing the rate of apoptosis of CFU-E cells, the maturation velocity of reticulocytes and the release of EPO by the kidneys, respectively, are shown.

Note, all subsequent simulations were done using the parameter values obtained by the procedure described above, if not stated otherwise. Thus, for all settings the precise same set of parameters has been used. In particular, parameters have not been adapted for a specific simulation, in order to improve data fitting. For a list of the parameter values see FIG. 4A.

After all parameter values of the model were assigned, the inventors ran some simulations and compared the model output with data found in literature. The inventors used data collected in several studies regarding different situations: excess of red cell mass, recovery after blood loss and administration of ESAs to increase the erythrocyte population.

High Altitude Dwellers

Exceeding red blood cell mass, as well as a low number of erythrocytes, is detrimental for the body. But whereas the feedback through erythropoietin acting on progenitor and precursor cells is reasonably fast in case of a decreased number of red blood cells, it is very slow when red cell mass is inappropriately high. This is because even if the production of precursor cells is distinctly reduced the immediate effect on the number of erythrocytes circulating in the blood is only a small one. This is due to the relatively long life span of erythrocytes of about 120 days. Thus, if the feedback acting on the erythroid cells in the bone marrow would be the only control loop, correction of exceeding cell mass would be very slow. This suggests that there is need for an additional mechanism which acts more effectively in situations of too many circulating red blood cells. Indeed, physiologists became aware of such a mechanism only two decades ago. This mechanism is called neocytolysis, referring to the fact that especially young red blood cells, so called neocytes, are prone to it. It is suggested, that under suppression of EPO, when plasma concentration drops beneath a certain threshold, active hemolysis of neocytes is triggered. Neocytolysis is probably responsible for the anemia of astronauts returning from space mission (C. P. Alfrey, M. M. Udden, C. Leach-Huntoon, T. Driscoll, and M. H. Pickett. Control of red blood cell mass in spaceflight. *Journal of Applied Physiology*, 81:98-104, 1996; M. M. Udden, Pickett M. H. Driscoll, T. B., C. S. Leach-Huntoon, and C. P. Alfrey. Decreased production of red blood cells in human subjects exposed to microgravity. *The Journal of Laboratory and Clinical Medicine*, 125:442-449, 1995.) Further, it can be observed in high altitude dwellers descending to sea level (see Rice 2001), and it is believed to contribute to red blood cell degradation in patients treated with ESAs. (see Alfrey et al.; C.-C. Chang, Y. Chen, K. Modi, O. G. Awar, C. P. Alfrey, and L. Rice. Changes of red blood cell surface markers in a blood doping model of neocytolysis. *Journal of Investigative Medicine*, 57:650-654, 2009; Rice 1999).

Figure 6A:
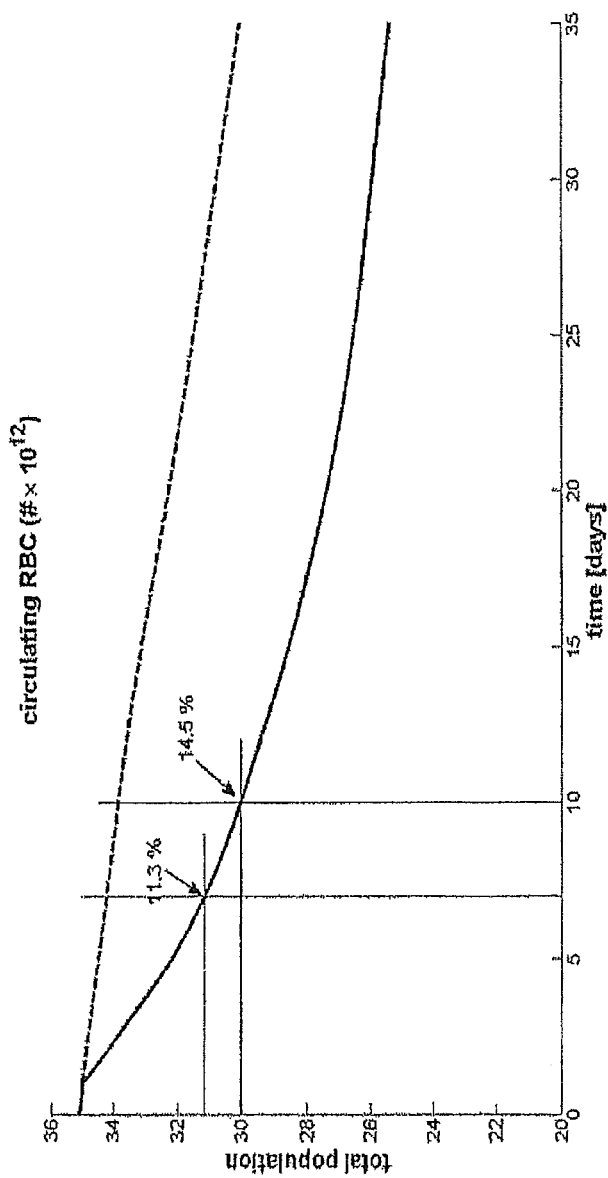
FIGS. 6A-6C set forth graphs of the total population of circulating RBC as a function of time illustrating the effect of neocytolysis in the development of erythrocytes in a high altitude dweller descending to a lower altitude during 6A: days 0-35, 6B: days 0-10, and 6C: days 10-35, according to the model of this invention.
Figure 6B:
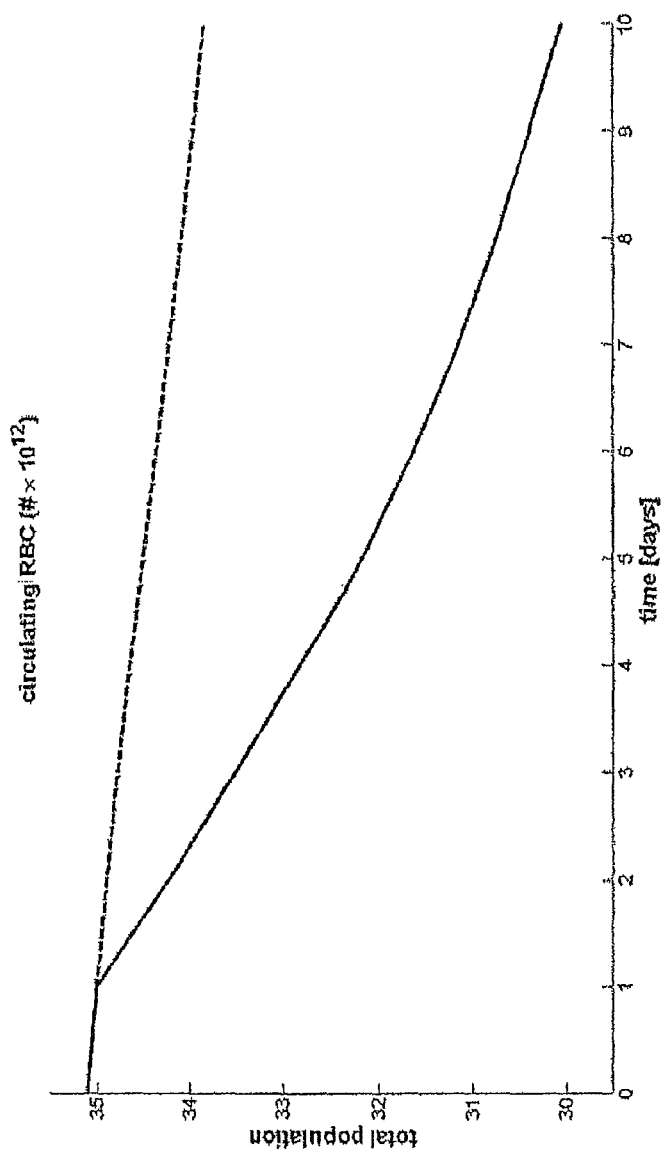
Figure 6C:
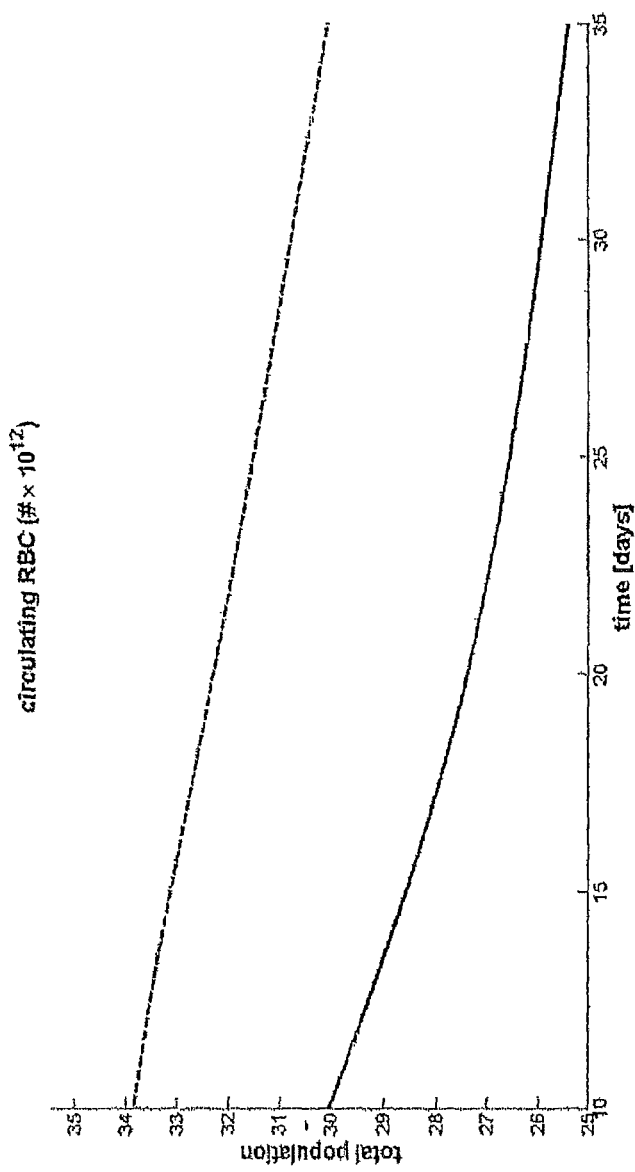

There are several studies concerning neocytolysis in descending high altitude dwellers and astronauts returning from space mission. It was observed that during the first few days (7-10 days), erythrocyte population was reduced by 9-18%. Thus, the order of magnitude in change in red cell mass is well beyond what could be explained by a reduced erythropoiesis. If further adaptation is necessary, it progresses slower and it seems to be controlled mainly through adaptation of the number of erythroid cells developing in the bone marrow. In FIGS. 6A-6C, a simulation for a 75 kg man descending from high altitude to sea level is presented. It was assumed that the red blood cell population was 40% increased, due to the oxygen poor environment. FIG. 6A shows the development of the red cell mass during the first 5 weeks. Further, it was compared how the system reacts considering neocytolysis (solid line) and without considering neocytolysis (dashed line). The predicted reduction of red cell mass, if considering neocytolysis, lies within a physiological meaningful range. After 7 days a decrease in RBCs of 11.3% can be observed and after 10 days the reduction from the original value accumulates to 14.5%. It can be clearly seen that without neocytolysis the model output is nowhere near the observed behavior of the body. In 6B the difference in the behavior of the model with and without neocytolysis is emphasized. In the first 10 days, the simulations for the two versions of the model differ distinctly, whereas in the following 25 days it can be observed that the slopes of the two curves are relatively similar, as shown in FIG. 6C. This observation is in agreement with the suggestion that neocytolysis is only a prominent factor in the first few days (see Rice 2005). In the simulations, the influence of the destruction of young erythrocytes plays a key role during the first days but gets almost negligible in comparison to the influence of a reduced erythropoiesis later on.

Blood Donation

In this subsection some simulations are presented, which show the recovery of the erythrocyte population after blood donation. The results are compared to several data sets from literature.

FIGS. 7A-7C show a simulation of a standard blood donation of about 550 ml obtained from a person weighing 75 kg. The simulation starts in the steady state and after one day 9% of the erythrocytes population is lost, due to blood donation. In FIG. 7A, it is illustrated how erythropoiesis adapts to this stress situation and drives the system back to the original state. Almost immediately after the oxygen carrying capacity is reduced, because of the loss of RBC, more EPO is released into the blood (see FIG. 7A). Interestingly, the EPO level peaks after about 5 days and thereafter declines continuously although the erythrocyte population is far from back to normal at this time (see FIG. 7C). Maeda et al., (see H. Maeda, Y. Hitomi, R. Hirata, H. Tohyama, J. Suwata, S. Kamata, Y. Fujino, and N. Murata. The effect of phlebotomy on serum erythropoietin levels in normal healthy subjects. *Int J Hematol*, 55(2):111-115, April 1992), observed a similar behavior when studying the erythropoietin level after a 400 ml phlebotomy in 14 normal subjects. EPO concentration peaked after about 7 days, and soon afterwards started to decline slightly. Also almost immediately after phlebotomy, a small reaction in the number of reticulocytes can be observed (see FIG. 7B). Their number increases slightly appearing as a small "step". But the dominant effect can be seen only within a few days. Due to the increased erythropoietin concentration more progenitor cells survive, and thus more cells enter the precursor cells class, and as a consequence more reticulocytes mature. The population of circulating erythrocytes increases continuously after blood donation, shown in the FIG. 7C. At first the recovery is very small, but gets more prominent once the reticulocyte population increase distinctly because of the better surviving probabilities of the CFU-E cells. Less than 40 days after blood donation, the erythrocyte population reaches its initial value.

These simulation results coincide with the findings in a study by Pottgiesser et al. (see T. Pottgiesser, W. Specker, M. Umhau, H.-H. Dickhuth, K. Roecker, and Y. O. Schumacher. Recovery of hemoglobin mass after blood donation. *Transfusion*, 48:1390-1397, 2008). In this study, the recovery of total hemoglobin (tHb) after a standard blood donation in 29 male volunteers (mean±standard deviation: 76.6±11.2 kg weight, 30±10 years old, 181±7 cm height) was investigated: "After donation of approximately 550 ml of whole blood, the lost amount of tHb of 75±15 g (8.8±1.9% tHb baseline) was recovered after a mean of 36±11 days (range: 20-59 days) . . . . In many subjects a delay of approximately 5 days was observed after blood donation in which no or only a minor increase in tHb occurred. After this short delay, a continuous restoration of tHb was noted . . . ". See Pottgiesser et al. In this study first-time, rare and multiple-donors were included. It is generally agreed that iron stores decrease after blood donation. Therefore, in some test subjects, a slight iron deficiency could be an explanation for a prolonged recovery period. Fowler et al. (see W. M. Fowler and A. P. Barner. Rate of hemoglobin regeneration in blood donors. *The Journal of American Medical Association*, 118 (6):421-427, 1942) found that the mean recovery period in young men, who donated blood several times, was 49 days, but could be shortened to 35 days when supplementary iron was administered.

Figure 8A:
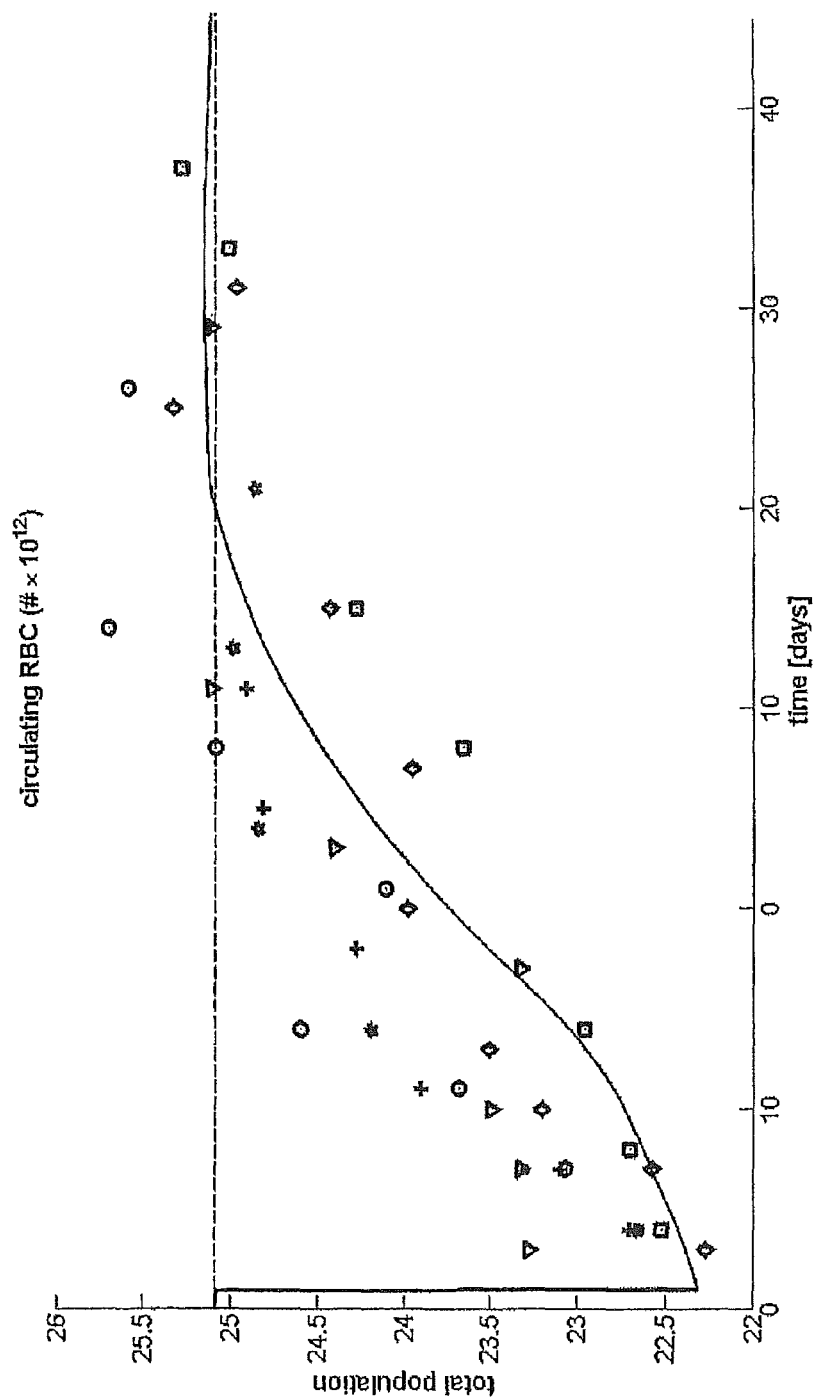
FIG. 8A sets forth a graph of the total population of RBC as a function of time for six patients, comparing data from Pottgiesser et al., citation below, to a prediction according to the model of this invention.

Pottgiesser et al. also presented individual data of 6 test subjects. The data is given in percentages of the individual tHb baseline (=100%) at the beginning of the trial, i.e., before blood donation. The inventors defined the steady state of the model to be the red cell mass baseline, and plotted the relative changes in tHb observed by Pottgiesser et al. together with the model prediction. The results are presented in FIG. 8A. The model fits the data not only qualitatively but also quantitatively very well.

Figure 8B:
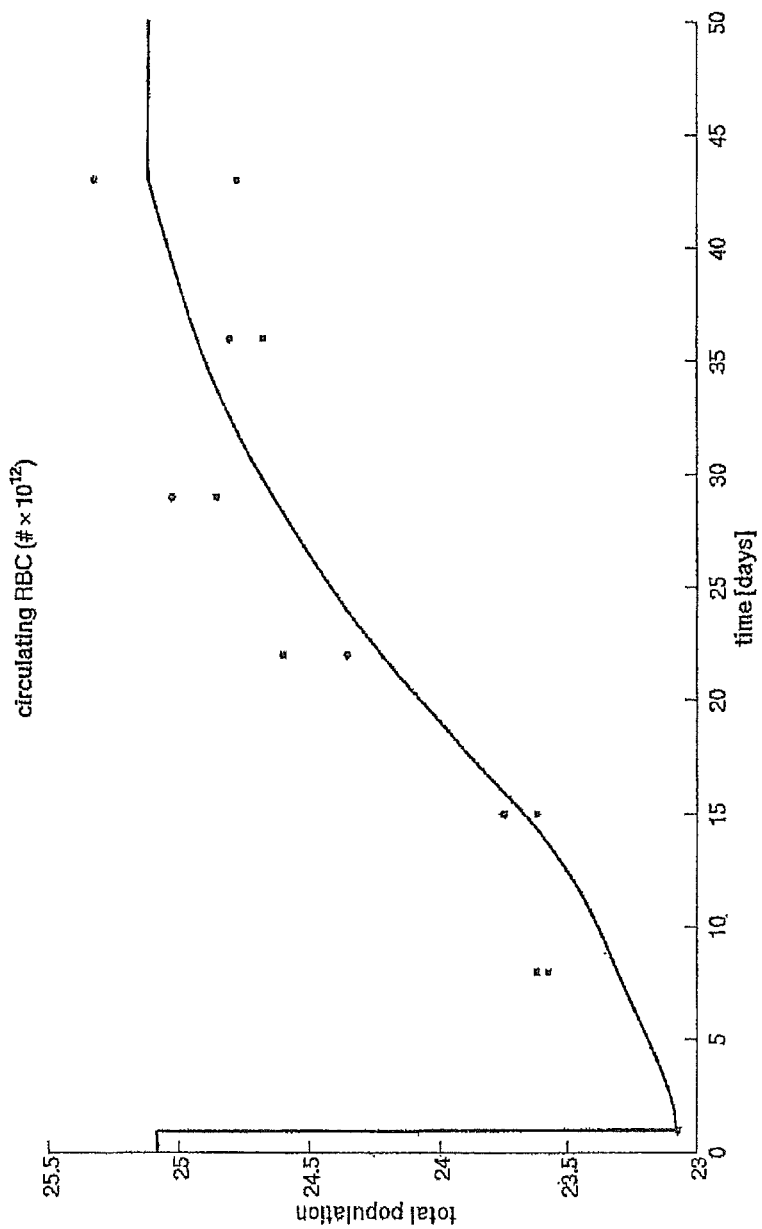
FIG. 8B sets forth a graph of the total population of RBC as a function of time for a donation of 8% blood volume, comparing data from Wadsworth, citation below, to a prediction according to the model of this invention.

Furthermore, the inventors compared the model output to a study done by Wadsworth. (see G. R. Wadsworth. Recovery from acute haemorrhage in normal men and women. *The Journal of Physiology*, 129:583-593, 1955). The author compared the mean recovery of 7 females to 7 males after the subjects were bled of about 8% of their blood volume. The data in Wadsworth is given in percentage of Hb baseline and again the inventors plotted the relative changes measured in the study together with the model simulation, see FIG. 8B. Again the model prediction fits the data quite well.

Although a comparison of the model simulation and the data collected in the two studies, Pottgiesser et al., and Wadsworth, can be only done with some reservations, the results indicate that the model is sufficient to simulate modest phlebotomy of a healthy adult. Note, the inventors compare the total number of RBC to the total hemoglobin or the hemoglobin concentration, respectively. Measurements for tHb and Hb are affected by, e.g., vigorous excitement, dehydration, smoking, severe vomiting, etc. Thus, these measurements need not be consistently directly proportional to the total number of erythrocytes. Nevertheless, the results are very promising, especially with regard to the fact that the model parameters were not adapted to fit these special data sets but the standard (guessed) parameter set was used for all simulations, see FIG. 4A. The predicted recovery period coincides with the mean recovery in Pottgiesser et al. and Fowler et al. (after iron supplementation) and the individual data seem to correspond to the simulations of average behavior in adults. (See Fowler et al.).

Figure 9A:
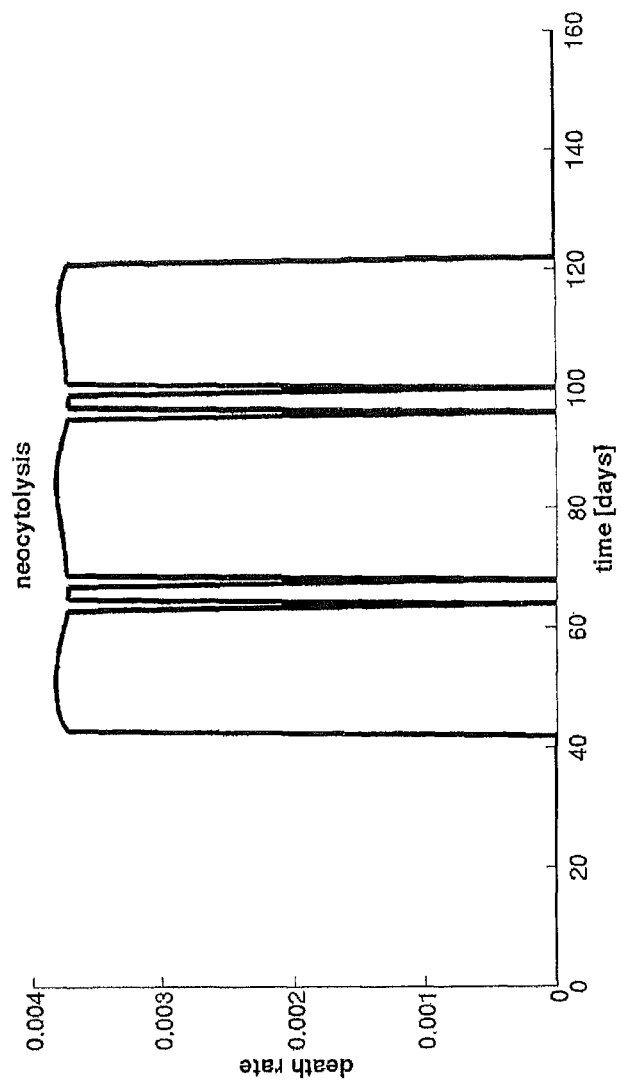
FIG. 9A sets forth a graph of the death rate for neocytes as a function of time illustrating the effect of neocytolysis on the death rate during the recovery period after a blood donation of 550 ml, according to the model of this invention.
Figure 9B:
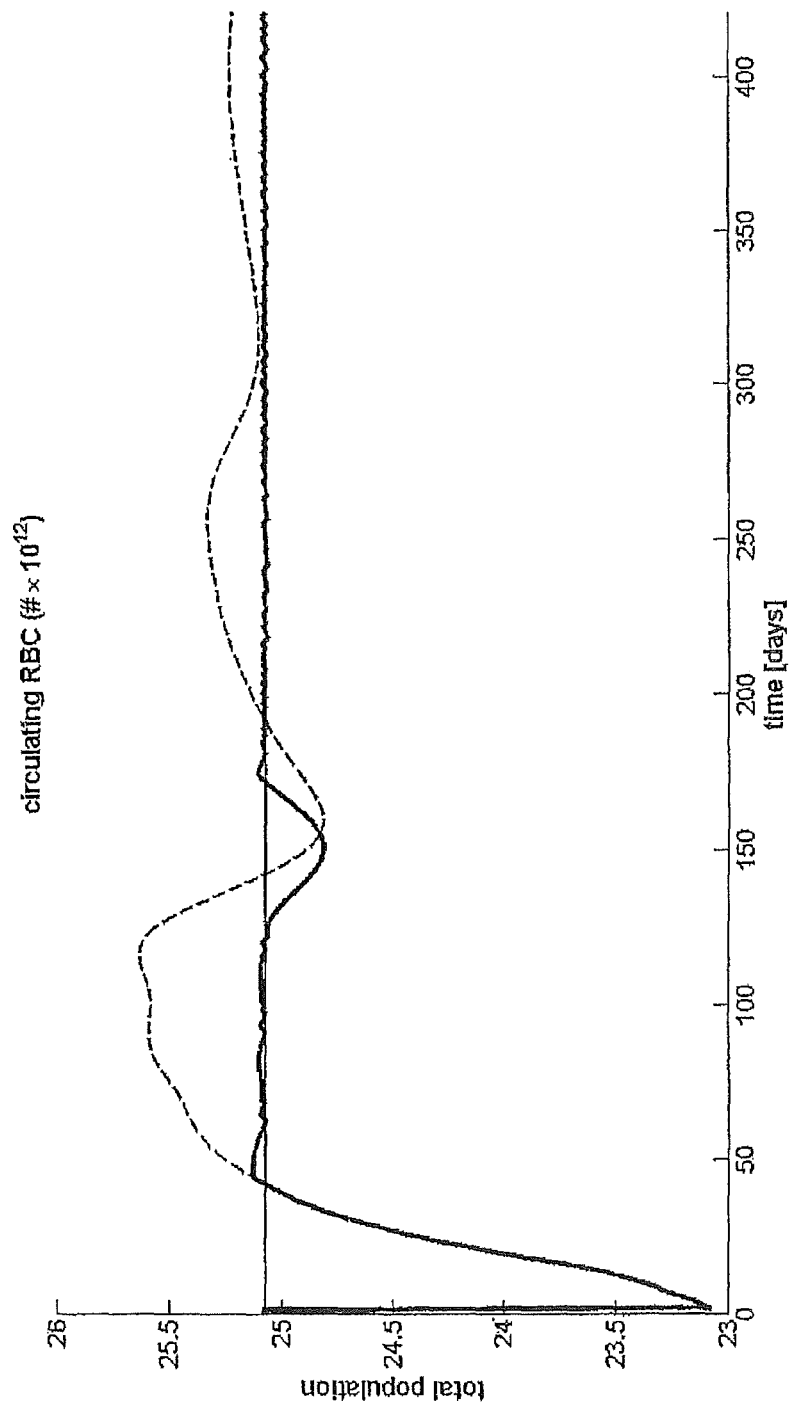
FIG. 9B sets forth a graph of the total population of circulating RBC as a function of time in a long run simulation with the model of this invention for blood donation (solid line with neocytolysis, dashed line without neocytolysis).

Another fact that could be observed in the model—which is possibly more of theoretical importance—is that the system without neocytolysis would tend to over compensate for the loss of red cell mass. The negative feedback loop through erythropoietin affects mainly the numbers of CFU-E cells. The indirect effect on the number of erythrocytes is relatively slow, because it takes some days until progenitor cells mature to erythrocytes. The cells entering the blood stream are mature CFU-E cells that survived under a certain level of EPO days ago. Consequently, more cells than normal enter the blood stream during a period of a few days when the level of erythropoietin decreases to normal. In the simulations, neocytolysis is triggered because of a small excess of red cell mass after day 42. The plot in FIG. 9A shows the rate of neocytolysis after a blood donation of 550 ml. The mortality rate is very small throughout the simulation ($<0.004$), but continues over a considerable time. Even though the effect seems very small at first sight, comparing the behavior of the model with and without neocytolysis makes it clear that neocytolysis allows for a tighter and more stable control of the erythrocyte population. See FIG. 9B for a comparison of the two simulations. The solid line shows the model output with neocytolysis and the dashed line without neocytolysis. Whereas the dashed line overshoots the steady state (horizontal solid line), the solid line keeps very tightly to the baseline value after recovery of the blood loss. A slight drop in the number of erythrocytes can be observed around day 120 in both simulations. In the curve illustrating the model without neocytolysis, this drop is more pronounced (about $1 \times 10^{12}$ cells compared to about $0.4 \times 10^{12}$ cells). Both systems react to this drop and slightly increase erythropoiesis. Again the system without neocytolysis overcompensates and shows small oscillations around the steady state in the long-term behavior. With neocytolysis, a small drop is observed in the number of erythrocytes at some point but this remains the only drop and afterwards the system stays in the steady state.

A drop in the RBC population was observed in both simulations, because after the blood loss, the model predicts a considerable elevation of erythroid cells in the bone marrow. Hence, the number of cells entering blood circulation at a special time $\bar{t}$ is higher than usual. Assumption 19 of the model implies that all the cells that entered the erythrocyte class at time $\bar{t}$ die precisely at time $\bar{t}+120$. Now, because the production rate of new RBC after blood donation was higher (day 1-50), more cells reach the maximum age at day 120-170 and die. This causes the erythrocyte population to drop and the regulatory mechanisms start to compensate for the profuse loss of cells.

Preoperative Administration of Erythropoiesis Stimulating Agents

Administration of ESAs is common practice not only in treatment of anemia but it is also used to elevate the number of RBCs in patients that have to undergo major elective surgeries, like for instance, hip arthroplasty. The increase in hemoglobin levels in patients reduces the need for allergenic blood transfusions after surgery and it further allows the subjects to donate blood preoperatively for autologous blood transfusions. Allergenic blood transfusions are accompanied by risks like transfer of pathogens, fever, dyspnea and an anaphylactic shock. However, acquisition costs of erythropoiesis stimulating agents are high and it is in the hospitals interest to choose a most cost-effective administration scheme. (D. Jaspan. Erythropoietic therapy: cost efficiency and reimbursement. *American Journal of Health-System Pharmacy*, 64(16 Suppl 11):19-29, August 2007).

Figure 10A:
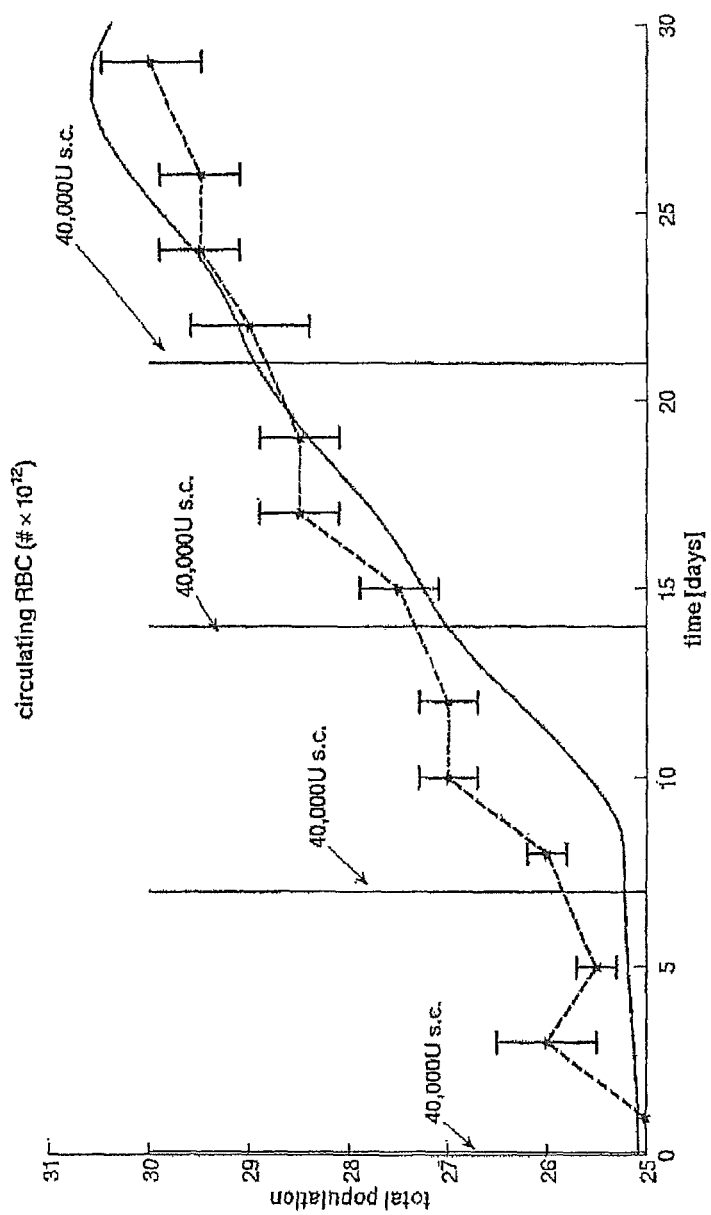
FIG. 10A sets forth a graph of a simulation with the model of this invention of preoperative administration of EPO. Data points are taken from Cheung et al., (citation below). Mean values (denoted by stars) ±2 standard errors are plotted and connected with a dashed line. The solid line shows the model simulation for the administration scheme of 40000 U q.w. s.c.

Different from dialysis patient in healthy persons, the common administration route of ESAs is subcutaneous (s.c.) administration. Cheung et al., (see W. Cheung, N. Minton, and K. Gunawardena. Pharmocokinetics and pharmacodynamics of epoetin alfa once weekly and three times weekly. *European Journal of Clinical Pharmacology*, 57:411-418, 2001), published data concerning pharmacokinetics and pharmacodynamics of Epoetin alfa for a drug administration of 40,000 U once weekly (q.w.) s.c. for four weeks in healthy persons. The pharmacokinetic profile was used to asses the model parameters describing exogenous erythropoietin. Cheung et al evaluated that the mean peak in serum erythropoietin concentrations was 861±445.1 mU/ml after 16.1±4.27 h after administration with a mean half-life value of 15.0±6.12 h. Obviously, there is a huge variability in the pharmacokinetic profile of Epoetin alfa in healthy persons. The mean values (a peak in serum EPO levels of 861 mU/ml and a half-life of 15 h) were used as model parameters. A comparison of a model simulation using the described administration scheme of 40,000 U q.w. s.c. for four weeks and the pharmacodynamic data published in Cheung et al., can be found in FIG. 10A. Overall the model fits the data nicely. Qualitatively and quantitatively the average behavior of the test subjects seems to be predicted well, especially with regard to the fact that the model parameters have not been adjusted for this special situation but the standard parameter set (shown in FIG. 4A) was used. Nevertheless, in the first few days of treatment the model underestimates the red cell mass, but it provides a satisfactory fit during the third and fourth week of ESA administration.

Figure 10B:
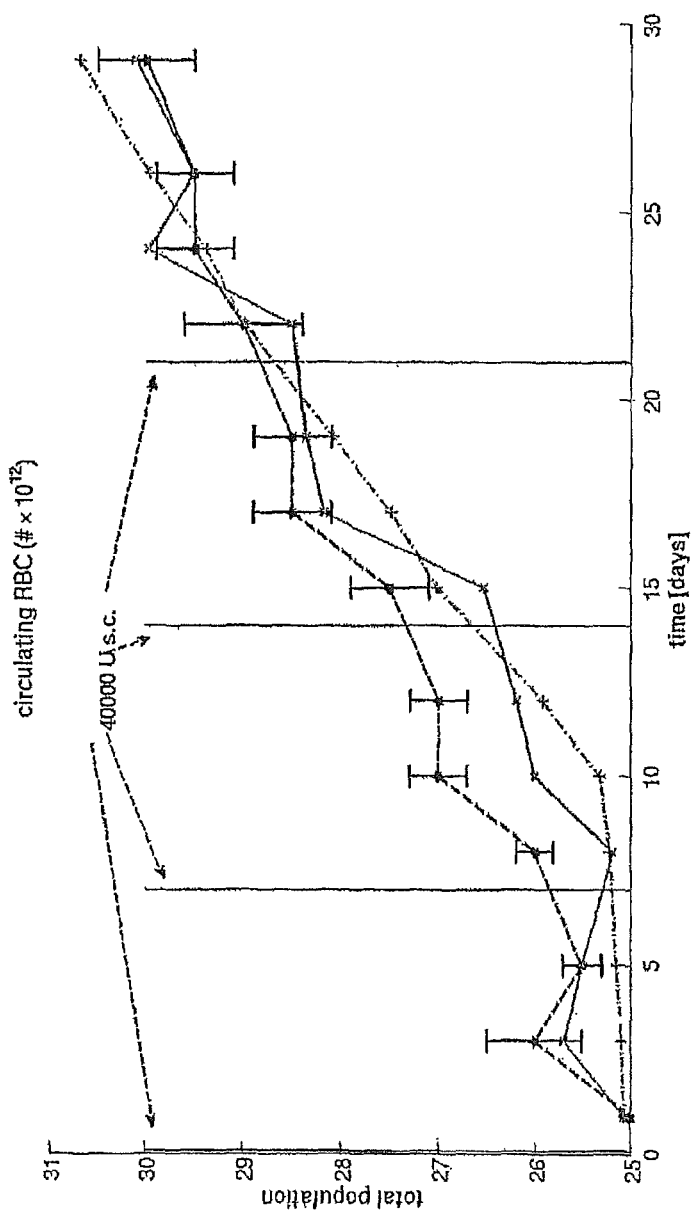
FIG. 10B sets forth a graph of a simulation with the model of this invention of preoperative administration of EPO. Data points are taken from Cheung et al., (citation below). Mean values (denoted by stars) ±2 standard errors are plotted and connected with a dashed line. The solid and dashed lines without error bars show the model simulation for the administration scheme of 40000 U q.w. s.c. with (solid) and without (dash-dotted) considering the release of stress reticulocytes.

The delayed reaction of the model could eventually be explained by an underestimated ability of the body to release stress reticulocytes and a bit long transit time of progenitor cells. Both concepts are mentioned among others for a revisited model above. The idea of a very fast release of premature reticulocytes from the bone marrow was relatively easy to include in the model. It only requires minor changes for the population equation describing the reticulocyte class (Assumption 12 is replaced by Assumption 26), but apart from that, the model assumptions and parameters can be left unaltered. Therefore, the inventors were able to run simulations comparing the model performance considering on one hand a variable maturation velocity for reticulocytes (Assumption 12), and on the other hand the release of stress reticulocytes under high levels of EPO (Assumption 27). In FIG. 10B, these simulations are presented together with the pharmacodynamical data from Cheung et al. Mean values, denoted by stars, ±2 standard errors are again plotted and connected with a dashed black line. For an easier comparison of the model with the measured data, the inventors only plotted those points of the simulation where data was ascertained. The points were connected with a solid line for the model considering the release of stress reticulocytes and a dash-dotted line for the standard model. It is clearly evident that the behavior of the model considering stress reticulocytes is qualitatively superior to the standard model. Further, the solid line lies more often within the standard error bars of the measured data than the dash-dotted line. The only point of criticism is that the altered model declines instead of rising between day 5 to 7. This could be due to an overestimation of the transit time of BFU-E and CFU-E cells and should be further investigated.

The inventors further compared the model output to another study by Feagan et al. concerning pre-surgical administration of Epoetin alfa. (See C. J. Feagan, B. G. and Wong, A. Kirkley, D. W. Johnston, F. C. Smith, P. Whitsitt, S. Wheeler, and C. Y. Lau. Erythropoietin with iron supplementation to prevent allogeneic blood transfusion in total hip joint arthroplasty. *Annals of Internal Medicine*, 133:845-854, 2000). Patients undergoing primary hip joint arthroplasty were treated with ESAs starting four weeks prior to the surgery. Similar to Cheung et al., patients were administered four doses of Epoetin alfa q.w. s.c. Three groups had been distinguished: a low dose group—receiving 20,000 U Epoetin alfa q.w. s.c., a high dose group—receiving 40,000 U Epoetin alfa q.w. s.c., and a control group—receiving a placebo. Although in Cheung et al. and in Feagan et al.—in the high dose group—a similar administration scheme was used, the pharmacodynamic reaction differs slightly, probably because the demographics of the patients enrolled are quite different. For instance, a mean age of 28.1±6.51 in Cheung et al. compared to a mean age of 68.9±10.8 and 67.3±11.0 in the low-dose and high-dose group, respectively in Feagan et al.; 53% men in Cheung et al. compared to 7.6% and 11.4% women in the low-dose and high-dose group, respectively in Feagan et al.

Figure 11A:
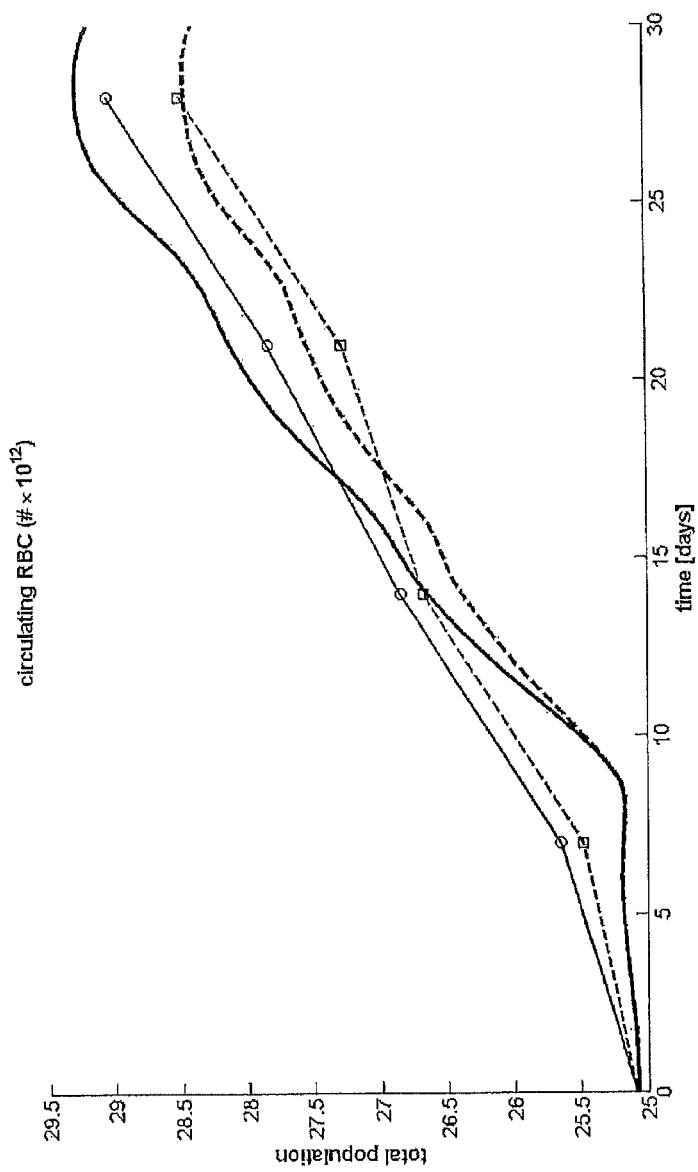
FIG. 11A sets forth a graph of simulations with the model of this invention of preoperative administration of EPO. Data points are taken from Feagan et al., (citation below). Squares connected by dashed straight lines represent the mean values of observed data for the "low dose group" (20,000 U/week), whereas circles connected by solid straight lines represent the mean values of observed data for the "high dose group" (40,000 U/week). The dashed and solid curves depict the corresponding model simulations, respectively.
Figure 11B:
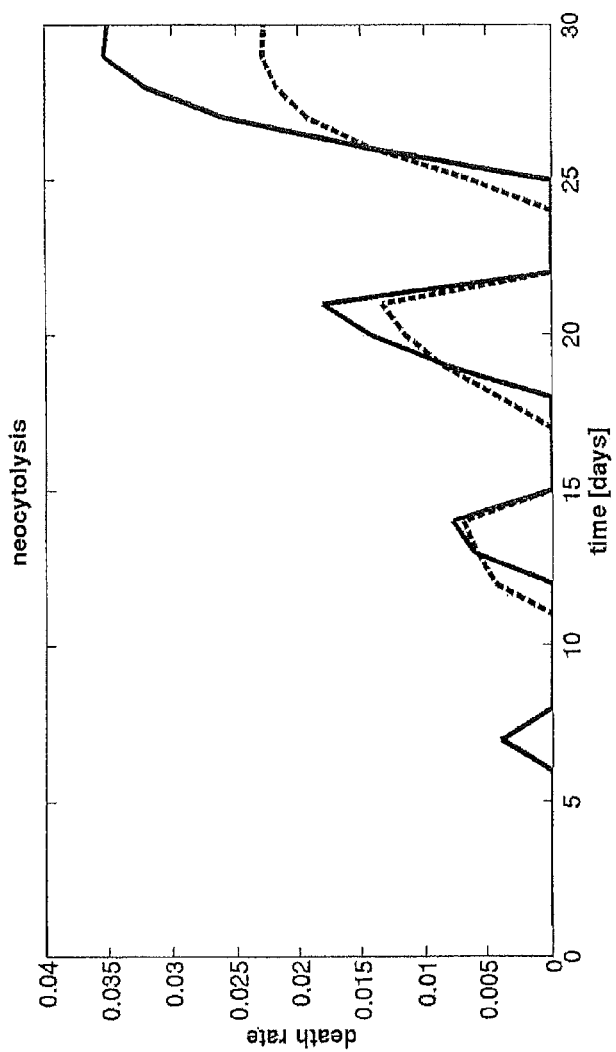
FIG. 11B sets forth a graph of the death rate for neocytes as a function of time illustrating the effect of neocytolysis during pre-surgical ESA administration. The dashed and solid curves depict the death rate for neocytes for the low dose group and the high dose group shown in FIG. 11A, respectively.

All three groups in the study by Feagan et al. were treated with supplementary iron. Hence, the assumptions for the model are valid and simulations should be comparable with observed data. In Feagan et al., no pharmacokinetic data was published. Thus, the inventors orientated themselves by the data published in Cheung et al. The half-life of Epoetin alfa was slightly reduced to 13 h, which lies well in between the data's standard deviation. In order to incorporate the data measured (hemoglobin concentration) into the plots, a method similar to the method described above was used. In FIG. 11A, model simulations and data are compared. The model predicts well the average reaction to treatment, both in the low dose and in the high dose group. Again, during the first few days the gain in red cell mass is underestimated by the model, but afterwards the predictions of the model seem to be accurate. Interestingly, doubling the dose from 20,000 U to 40,000 U leads only to a slight increase in RBCs. The inventors observed that neocytolysis gets more prominent in the intermediate phases from week to week, as shown in FIG. 11B. The rising cell mass, i.e., an unnatural high oxygen carrying capacity of the blood, leads to a suppression of endogenous erythropoietin. The short half-life of Epoetin alfa, results in almost complete decomposition of exogenous erythropoietin within 4 days. Therefore, EPO levels drop beneath the threshold where neocytolysis is triggered.

Figure 12A:
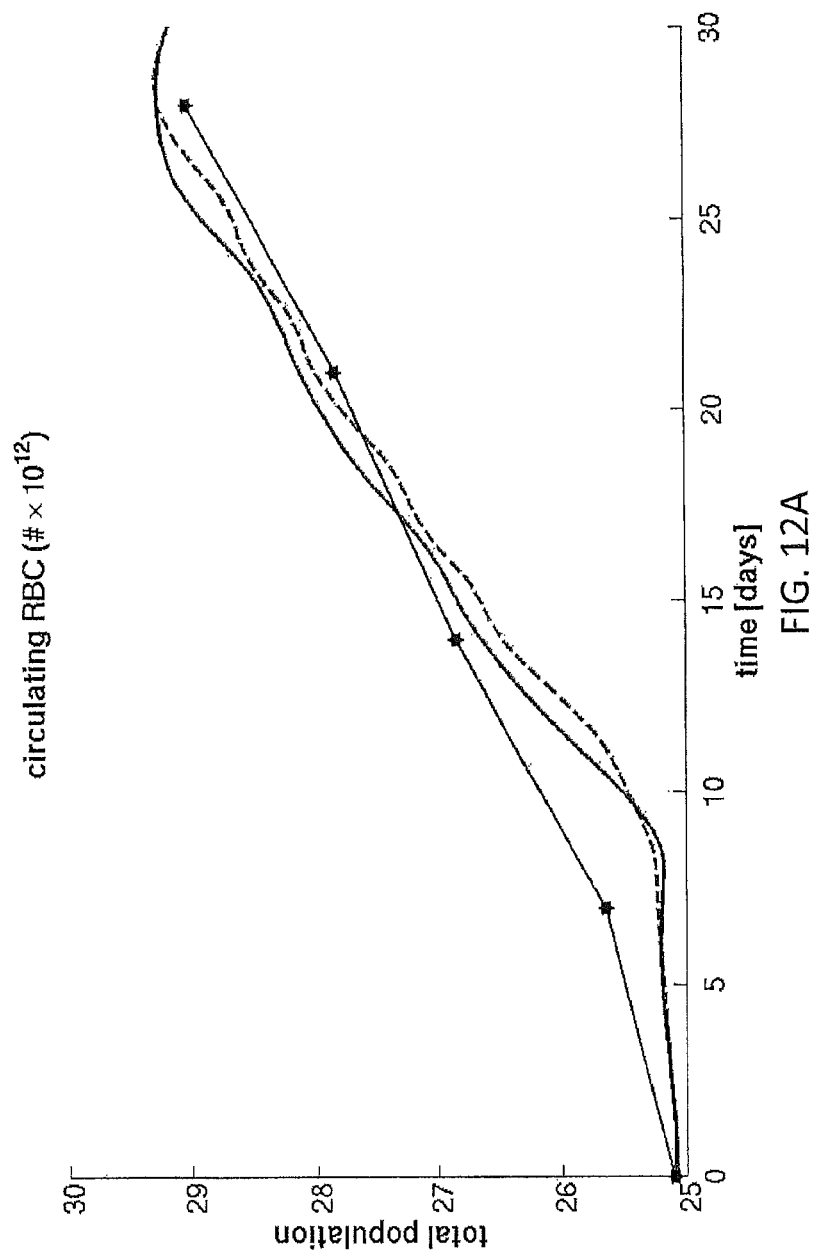
FIG. 12A sets forth a graph of simulations with the model of this invention of preoperative administration of EPO illustrating the consequence of different administration schemes. Data points (denoted by stars) are taken from Feagan et al., (citation below). The solid line represents the simulation result when the ESA is administered q.w (=80,000 U total) and the dashed line shows the model output when the ESA is administered twice per week (=16,000 U total).
Figure 12B:
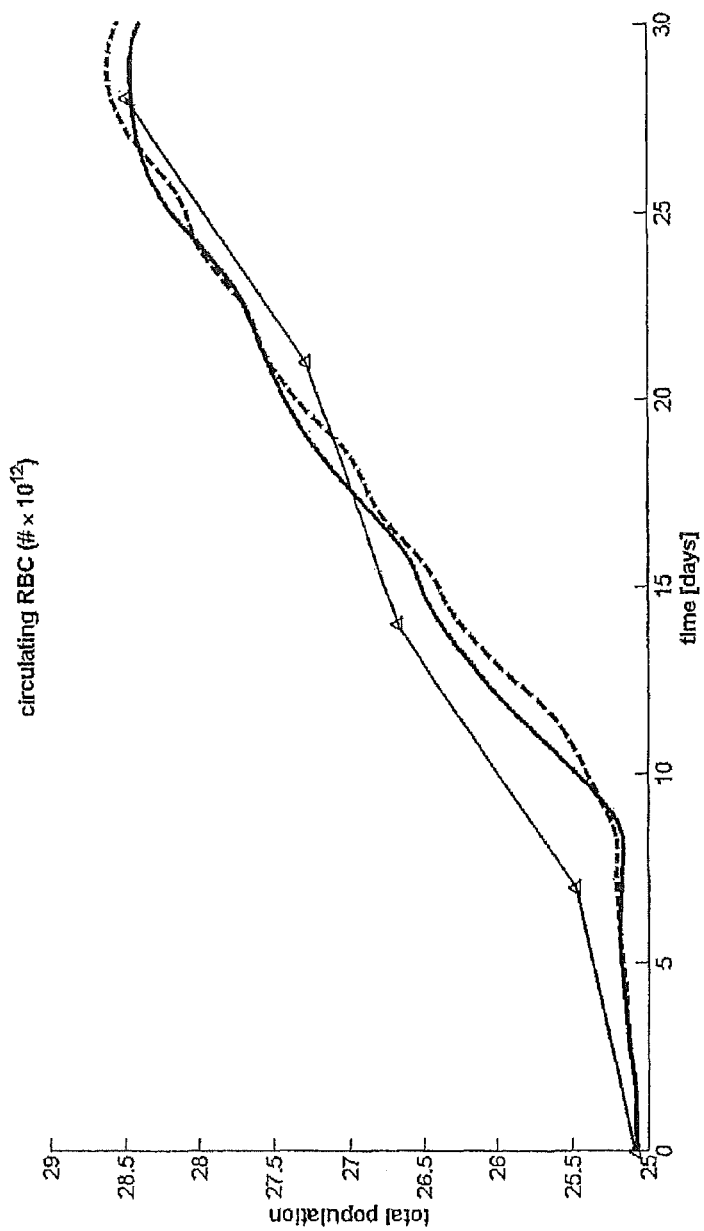
FIG. 12B sets forth a graph of simulations with the model of this invention of preoperative administration of EPO illustrating the consequence of changing administration frequency. Data points (denoted by triangles) are taken from Feagan et al., (citation below). The solid line represents the simulation result when the Epoetin α is administered q.w (=80,000 U total) and the dashed line shows the model output when the Epoetin α is administered twice per week (=16,000 U total).

In the previous section the model was compared to data available from literature. Throughout the simulations the model showed a very satisfying qualitative and quantitative behavior. This indicates that the model is valid in subjects where erythropoiesis is not impaired because of a reduced iron availability. Now, the inventors wanted to do some hypothetical simulations and consider situations where no experimental data is available. Of particular interest was the influence on ESA doses with regard to different administration schemes and also how demands of ESAs increase when the maximal lifespan of RBC decreases and/or the intrinsic mortality rate $\alpha_r^m$ increases, as it is the case in a majority of the dialysis patients Pre-surgical administration of EPO were considered above. Both studies, from which the inventors took data to compare it to the model output, used very high doses of EPO administered once a week. In Feagan et al., the authors compared the reaction to ESA prescription in a "high-dose" and "low-dose" group, where the "low-dose" group received only half the EPO dose than the "high-dose" group. Nevertheless, there was only a slight difference between the hemoglobin levels of those two groups. An interesting question is whether ESA doses can be reduced while achieving the same hemoglobin concentrations, when the frequency is increased to twice per week. In FIG. 12A, the stars represent mean values of the data points of Feagan et al., which were observed when administering 20,000 U/week during four weeks prior to the surgery. The data points are connected by straight lines. The lines show simulations with the model: the dashed line representing an administration of 20,000 U Epoetin α once a week for four weeks (=80,000 U total), whereas the solid line corresponds to an administration of 2,000 U Epoetin α twice a week for four weeks (=16,000 U total). Although the dose is less than a quarter, the effect on the number of RBC is similar. FIG. 12B sets forth graphs comparing two different administration schemes. Again, the triangles depict mean values observed in Feagan et al., during an administration of 40,000 U Epoetin α once a week for four weeks prior to the surgery. The lines represent model output for a simulation of 40,000 U/week Epoetin α (dashed line) for four weeks (=160,000 U total) and for a simulation of an administration of 3,000 U Epoetin α (solid line) twice a week for four weeks (=24,000 U total). The cumulative EPO dose is less than a sixth, when the drug is administered more often, but results in almost the same number of RBC. These findings suggest that a tremendous amount of Epoetin α could be saved by slightly increasing the administration frequency.

Testing Anemia Algorithms Using the Model

Simulations with the model of various rather different situations (RBC-recovery after blood donation, preoperative administration of EPO and relocation of high-altitude dwellers to lower altitudes) have demonstrated that the model is capable to describe the average dynamics of erythropoiesis in subgroups of the general population adequately just by adapting some of the parameters of the model to the subgroup considered. For this the following assumption is indispensable and has to be met by the subgroup:

(A) There is sufficient iron available in plasma such that erythropoiesis of subjects in the subgroup is not impaired because of lack of iron.

Since condition (A) can also be satisfied by administration of iron, the applicability of the model is not restricted to the subgroup of healthy people, for which the simulations mentioned above have been conducted, but is also applicable to a number of subgroups, including dialysis patients as long as the individuals of the subgroup can be characterized by an appropriate choice of the model parameters. Examples of such conditions are represented by reduced expected life span of RBCs and/or by reduced responsiveness of the precursor cells in bone marrow to EPO or ESAs.

The simulations mentioned at the beginning provided important results with respect to validation of the model. As far as clinical applications of the model are concerned the preoperative administration of EPO is certainly of interest, because simulations with the model showed that more frequent administrations of EPO (for instance three times per week versus one time per week through four consecutive weeks) will reduce the cumulative EPO-dose drastically without decreasing the attained hemoglobin level at the end of the treatment. However, clinical applications include the much larger group of dialysis patients satisfying Assumption (A). In the following it is always understood that only subgroups of dialysis patients are considered which satisfy Assumption (A). To be more specific, the model can be used for testing and comparison of EPO-administration algorithms (also called Anemia Algorithms). In addition the model can be used to simulate modifications of anemia algorithms and adaptations of anemia algorithms to specific subgroups of dialysis patients. Simple modifications will just replace two week intervals for changing administration doses by shorter time intervals, which are now possible because of availability of data on hemoglobin levels for every treatment session by the CritLine monitor (see U.S. Pat. No. 5,803,908 issued to Steuer et al. on Sep. 8, 1998) and leaving the decision criteria of the anemia algorithm otherwise unchanged. More sophisticated modifications will also base decisions on changes of doses on rates of change of the measured hemoglobin levels over some time interval.

That the model is capable of simulating the average hemoglobin dynamics in groups of dialysis patients sufficiently accurately is supported by the following observation. The model simulations show that for a specific algorithm, in general, fewer dose changes are needed and smaller cumulative EPO-doses can be administered if weekly changes of the doses are allowed compared to the situation where a change of the dose is only allowed every other week. This behavior of the simulations done for concrete algorithms (as for instance the anemia algorithm shown in Appendix D), but not referring to patient data, is confirmed by data on anemia algorithms which are indeed used at clinics and allow weekly changes of EPO-doses.

Erythropoiesis stimulating agents have been used to treat anemia in patients suffering from chronic renal failure for almost three decades. Studies have shown that a partial correction of anemia is preferable to a full correction (see e.g. Singh et al.; Strippoli et al.; Foley et al.). Optimal hemoglobin targets are still a matter of discussion and recommendations by the National Kidney Foundation changed several times over the last few years.

At the moment EPO doses in dialysis centers are prescribed using empirical algorithms. Changing the hemoglobin target always implies an adaptation of the algorithm which is used to prescribe EPO doses. In general, these algorithms are charts where the physician can look up what EPO dose to prescribe for a patient for the next one or two weeks using a current hemoglobin measurement. Most of them work in the following way: if this is the Hgb value of the patient, then administer that EPO dose. Some additional data are taken into account, such as whether there occurred any fast Hgb changes over the last few weeks. This approach bears some limitations and level of hemoglobin tends to fluctuate greatly and cycling phenomena are observed. An analysis of 31.267 patients on hemodialysis in the Fresenius Medical Care-North America database found that only 5% of patients persistently remained within a desired Hgb range of 11-12 g/dl for a period of 6 months. (See Collins et al.). Fishbane et al. analyzed data of dialysis patients collected over five years in a hospital and came to a similar conclusion. More than 90% of the patients experienced hemoglobin cycling. The authors state that changes in ESA dose were the most important driver and were associated with hemoglobin excursion in about 80% of cases.

There is not one standardized algorithm but there are hundreds of them used in clinics. Changing or adapting an existing algorithm is in general a matter of extensive discussion among medical doctors. Suggestions are made because of prior experience and then the most promising algorithm has to be tested in clinical use and after several months it can be analyzed if the adapted/changed algorithm performs satisfactorily. Thus, at the moment algorithms are changed and tested in a simple trial and error principle. This is an arduous path and can occasion high costs and even worsen patient outcomes.

Here, the mathematical model of erythropoiesis can be put to good use. Different ESA treatment regimen can be tested easily and their effects on hemoglobin levels observed over the next few months. Algorithms can be rated, for instance, with regard to the number of EPO changes and the cumulative EPO dose that is required over a given time period and whether they kept the "patient", i.e. the model simulation, within certain limits around the hemoglobin target value. The most promising algorithm can then be used in a clinical setting.

FIGS. 13-16 show what such a test for an algorithm could look like. Here, the anemia algorithm described in Tables A1-A8, called the FMS algorithm, was tested. This algorithm prescribes EPO doses using Hgb measurements every two weeks. The desired hemoglobin target value is 11 g/dl. Doses are changed every month if necessary, except one of the exception criteria is met. Then a prescribed dose can be already adapted after two weeks. The inventors compare this anemia algorithm to a slightly modified version. In the modified version doses are prescribed in the exact same way as in the FMS algorithm but for one thing: now it is checked every week (compared to every two weeks) if an exception criterion is met. If necessary, doses can be adapted weekly. Many physicians are very skeptical concerning allowing more frequent dose changes because they believe that this results in a larger number of dose changes over a given time. A large number of dose changes are thought to induce and amplify cycling phenomena. Interestingly enough, in almost all the simulations done, the modified FMS algorithm made as many or fewer dose changes. Hence, theoretically allowing for more frequent changes often reduced the number of actual dose changes. Further, in almost all simulation runs the modified FMS algorithm showed less pronounced hemoglobin cycling and could achieve this by using less EPO.

TABLE 2

Comparison of two different anemia algorithms over 200 days

Figure 13:
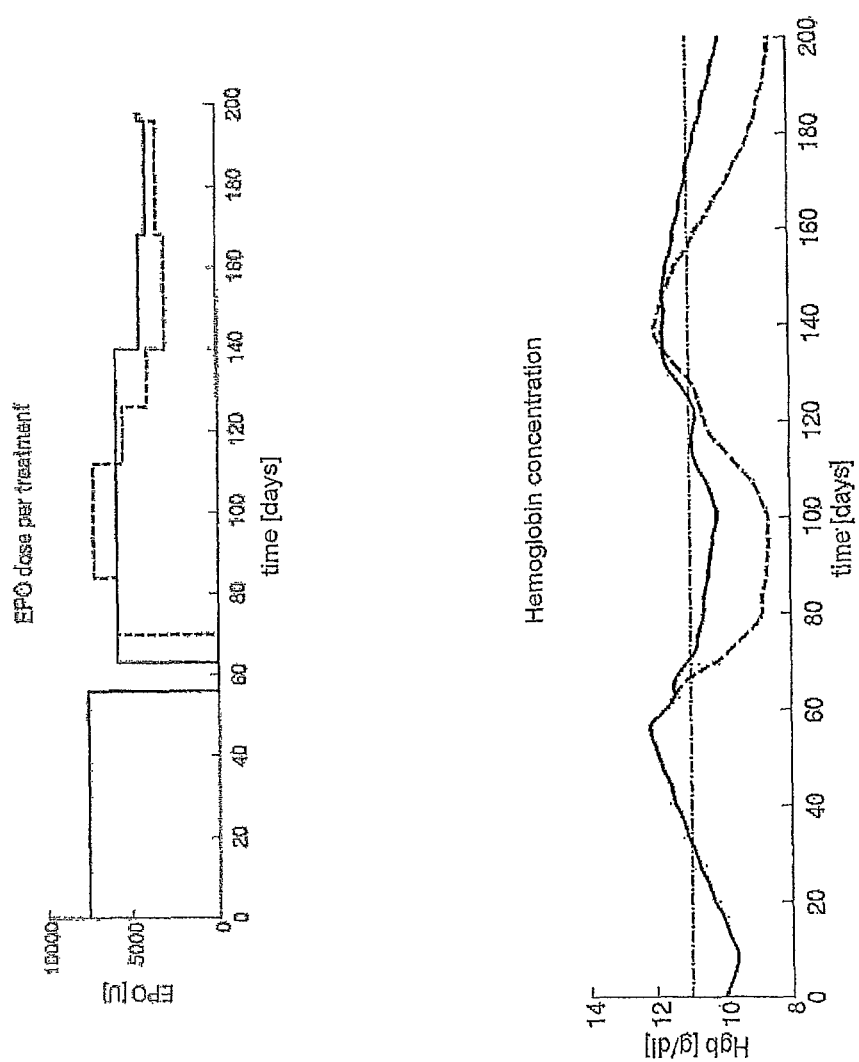
FIG. 13 sets forth graphs of EPO [U] administration and resulting hemoglobin concentration HgB [g/dl] as a function of time [days] for the administration algorithm described in Tables A1-A8 and as modified with the model of this invention with an RBC lifespan of 60 days and slightly suppressed reaction to EPO.
Figure 14:
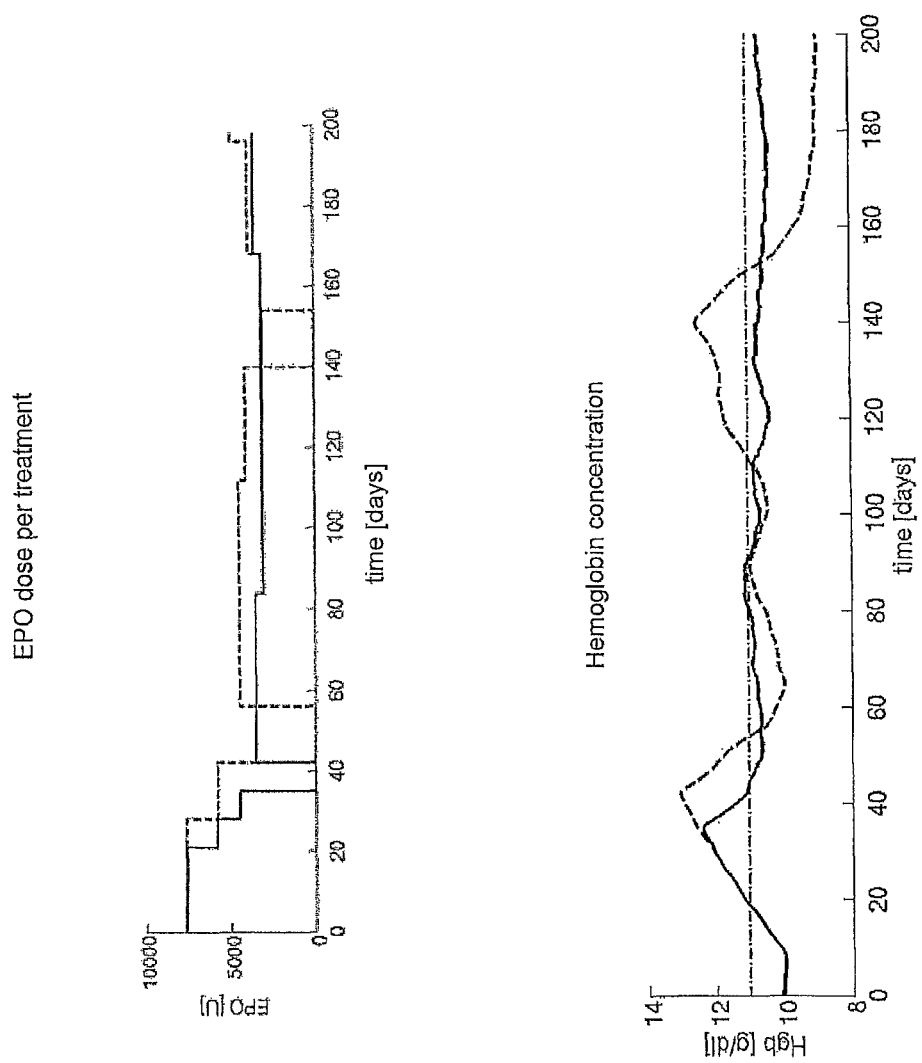
FIG. 14 sets forth graphs of EPO [U] administration and resulting hemoglobin concentration HgB [g/dl] as a function of time [days] for the administration algorithm described in Tables A1-A8 and as modified with the model of this invention with an RBC lifespan of 80 days and slightly suppressed reaction to EPO.
Figure 15:
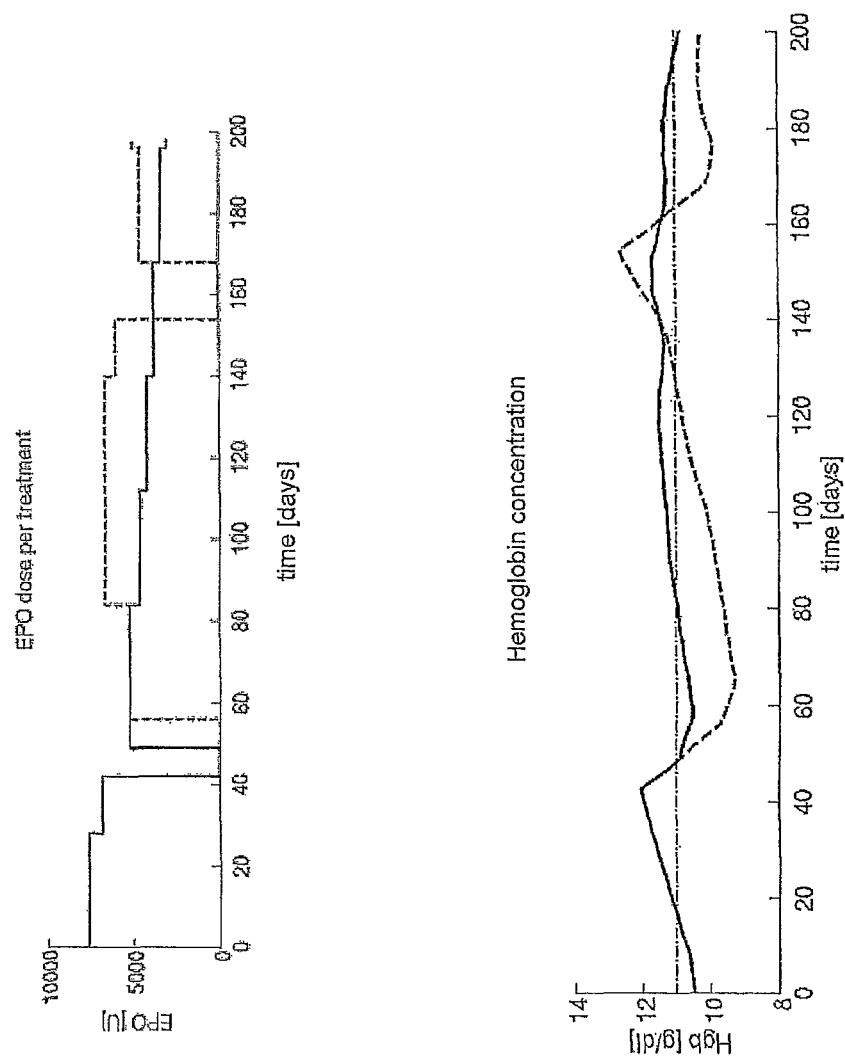
FIG. 15 sets forth graphs of EPO [U] administration and resulting hemoglobin concentration HgB [g/dl] as a function of time [days] for the administration algorithm described in Tables A1-A8 and as modified with the model of this invention with an RBC lifespan of 120 days and severely suppressed reaction to EPO.
Figure 16:
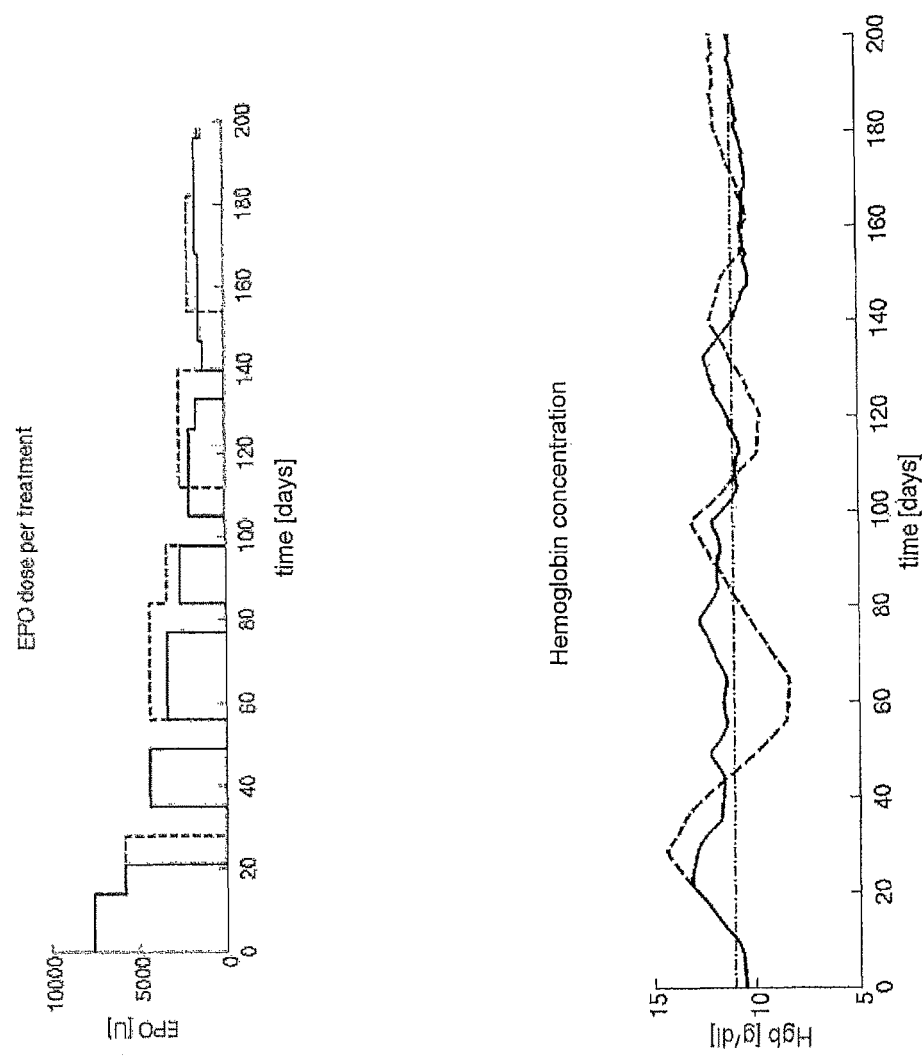
FIG. 16 sets forth graphs of EPO [U] administration and resulting hemoglobin concentration HgB [g/dl] as a function of time [days] for the administration algorithm described in Tables A1-A8 and as modified with the model of this invention with an RBC lifespan of 120 days and normal reaction to EPO.

| Anemia protocol | Bone marrow | RBC lifespan | Number of Dose changes | Cumulative EPO dose | Figure |
|---|---|---|---|---|---|
| FMS algorithm | Modest suppression | 60 days | 8 | 445200 | FIG. 13 |
| Modified FMS algorithm | | | 5 | 483400 | |
| FMS algorithm | Modest suppression | 80 days | 8 | 352800 | FIG. 14 |
| Modified FMS algorithm | | | 6 | 315800 | |
| FMS algorithm | Modest suppression | 120 days | 12 | 296800 | |
| Modified FMS algorithm | | | 10 | 245200 | |
| FMS algorithm | severe suppression | 60 days | 6 | 1325400 | |
| Modified FMS algorithm | | | 6 | 1325400 | |
| FMS algorithm | severe suppression | 80 days | 5 | 692400 | |
| Modified FMS algorithm | | | 5 | 692400 | |
| FMS algorithm | severe suppression | 120 days | 8 | 454000 | FIG. 15 |
| Modified FMS algorithm | | | 5 | 408000 | |
| FMS algorithm | Normal | 60 days | 10 | 349200 | |
| Modified FMS algorithm | | | 9 | 276600 | |
| FMS algorithm | Normal | 80 days | 9 | 298400 | |
| Modified FMS algorithm | | | 13 | 244200 | |
| FMS algorithm | Normal | 120 days | 10 | 220800 | FIG. 16 |
| Modified FMS algorithm | | | 15 | 196600 | |

In Table 2, one can find a complete list describing what testing the two algorithms involved. Moreover, some of the simulation runs are presented in this section for exemplification. For the simulations a reduced transit time of progenitor cells (see above) was considered. Thus, some of the model parameters changed. See FIG. 4B for a list of the used parameters. Note that these parameters refer to the situation in a healthy person and some of them change in dialysis patients, for instance, the RBC life span is reduced in the majority of them. Further, the response of the bone marrow to EPO is, in general, suppressed. For testing the algorithms, the inventors considered different combinations of RBC life spans, a normal response of the bone marrow, a right shifted EPO-dose response curve for progenitor cells and a reduced mitosis rate for progenitors. If no changes were made, the inventors call the bone marrow reaction normal. If only the EPO-dose response was altered ($k_1$=0.005) the inventors call the bone marrow reaction modestly suppressed and if additionally the mitosis rate was decreased the inventors call the bone marrow reaction severely suppressed ($\beta^q$=1.1). Further, to account for the fact that dialysis patients are over hydrated at the beginning of a dialysis session and that hemoglobin measurements are taken prior to dialysis, the inventors increased the predialysis blood volume from 5000 ml to 6000 ml. Moreover, to compute from the total RBC population the hemoglobin concentration a mean corpuscular hemoglobin of 29 pg was assumed, because, in general, anemia of CKD is normochromic. The duration for all simulations was 200 days.

TABLE A-1

Lab Orders: Hemoglobin weekly

| IF: | THEN: |
|---|---|
| New Patient | Draw Hgb first treatment and then follow weekly Hgb lab draw schedule |
| Post-hospitalization Patient | Draw Hgb first treatment back to facility and then follow weekly Hgb lab draw schedule |
| Hgb available from hospital or other source | Use only facility-drawn and Spectra-resulted Hgb values. Do not use local lab Hgb values (from hospital or other source) in calculating EPO dose |

EPO Cycle: When EPO dose change is indicated per algorithm, dose calculations and EPO order will be entered into the electronic system and documented appropriately in patient's medical record. The calculations will occur prior to the treatment after receipt of the Hgb result and the new EPO dose will be administered at the next treatment following the receipt of the Hgb result. For example:

TABLE A-2

| Facility Collects and Ships Spectra Labs | Spectra Receives, Processes and Transmits Result to Knowledge Center | New Dose Entered in Electronic System No Later Than Day Indicated Below | Patient Receives New Dose |
| --- | --- | --- | --- |
| Monday | Tuesday | Thursday | Friday |
| Tuesday | Wednesday | Friday | Saturday |
| Wednesday | Thursday | Saturday | Monday |
| Thursday | Friday | Monday | Tuesday |

TABLE A-3

| New Patients | |
| --- | --- |
| If Hgb is less than 10.0 g/dL and either TSAT is less than 20% or Ferritin is less than 100 ng/mL | Do not start EPO until the patient has received a one gram iron sequence per algorithm. Upon completion of the 1 gram iron sequence, recheck Hgb at next scheduled facility lab draw. If Hgb less than 10, start EPO according to Starting Dose Chart. |
| Starting Dose | 1. If Hgb is less than 10.0: Begin administration of EPO per Starting Dose Chart
2. If Hgb 10.0 or greater Do not begin administration of EPO. Start EPO when Hgb is less than 10.0 per Starting Dose Chart |

TABLE A-4

| General Orders | |
| --- | --- |
| Converting from patient's existing algorithm to revised algorithm | When converting from the patient's existing algorithm to the revised algorithm, start EPO with the patient's previous EPO dose, using rounding rules. |
| Route of Administration | All IV EPO dose will be administered IVP. |
| Missed Treatments | Administer ordered dose and contact M.D. to determine whether physician wants to order make up of missed EPO dose(s). |
| Frequency of Dose Change | EPO dose changes will be made monthly using Maintenance Dose Chart unless patient meets exception criteria (see Exceptions to Monthly Dose Changes).
EPO doses will not be changed more frequently than every 14 days unless Hgb is greater than or equal to 12.0 or patient is returning from the hospital. |
| Dosing Frequency | All doses based on 3 X/week administrations unless noted otherwise.
If patient is receiving EPO less than 3 X/week, calculate new dose and frequency as follows:
a. Calculate current dose times (X) current frequency (as ordered by physician) to determine the weekly EPO dose.
b. Divide weekly dose by three to use Dosing Chart. Round per rounding rules.
c. Use Maintenance Dose Chart to determine new dose.
d. Multiply new dose times three to determine weekly dose.
e. Divide weekly dose by ordered frequency to calculate the less than 3X per week dose. Round per rounding rules. |
| Minimum Dose per treatment | The minimum dose of EPO is 1000 units per treatment. If the calculated dose is less than 1000 units reduce the frequency by one as indicated in the Maintenance Dose Chart.
If total weekly dose (i.e., dose from Dosing Chart times frequency) is at least 3000 units, the frequency of administration will be 3 X/week unless otherwise ordered by physician. To get correct dose, divide total weekly dose by 3 and follow rounding rules. |
| Maximum Dose | EPO dose is not to exceed 400,000 units per month.
Maximum dose not to exceed Maximum Dose Chart. |
| No open EPO order in last 3 months | If no open EPO order in the last 3 months, when Hgb is less than or equal to 11.8 g/dL restart EPO dose using Starting Dose Chart. If the last Hgb is greater than 14 days old, obtain starting dose from physician (This is to prevent action on an old Hgb value). |
| Patients at maximum EPO dose per kg/body weight per treatment | Patients with a TSAT of equal to or greater than 30% and Ferritin greater than 200 and at maximum EPO dose per kg/body weight per treatment and Hgb is less than 10 g/dL for 3 consecutive months* with no Hgb increase of more than 0.2 g/dL:
a. Continued to follow physician ordered iron algorithm.
b. Decrease EPO dose by 10% using Maintenance Dose Chart. (See Decrease 10% column) |

TABLE A-4-continued

| | General Orders |
|---|---|
| | c. Every month thereafter, if no decrease in Hgb, decrease current dose by 10% using Maintenance Dose Chart until Hgb decreases by more than 0.2 g/dL from the baseline, then resume EPO at previous dose prior to Hgb decrease.<br>d. Discuss evaluation of hyporesponsiveness with physician. |
| Physician order apart from algorithm | Follow the algorithm subsequent to that dose change unless otherwise directed. |
| Consult with Physician | Nurse to consult with physician when nurse believes that, based on assessment of the patient's condition, it may not be appropriate to follow the algorithm. |
| EMP Rules | If the calculated dose cannot be entered into the electronic system due to EMP rules, complete and submit a Remedy ticket to over-ride the rules so calculated dose may be entered into the system. |
| Patient transferring into facility | Obtain starting dose from physician with admission orders. |

*Use Hgb when patient first reaches maximum dose as baseline. Compare that value to Hgb at the end of the third month to determine if it has decreased more than 0.2 g/dL in that period.

TABLE A-5

| Exceptions to Monthly Dose Changes | |
|---|---|
| Hgb greater than or equal to 12.0 g/dL | Hold and re-evaluate with weekly hemoglobin checks |
| Hgb is less than or equal to 11.8 g/dL on Held doses | Restart EPO at 25% decrease (see 25% decrease column) using Maintenance Dose Chart. If no open EPO order in last 3 months, resume EPO using Starting Dose Chart. |
| Hospitalized Patients | Prior to receipt of new Hgb result, continue pre hospitalization EPO dose.<br>If new Spectra Hgb result is received during or immediately following hospitalization, apply Maintenance Dose Chart and change dose immediately. |
| Hgb greater than or equal to 10 and increases by more than 1.0 g/dL over past 2 weeks | Decrease dose 25% using Maintenance Dose Chart |
| Hgb decreases by more than 1.0 g/dL over past 2 weeks and dose not currently on hold | Increase dose using Maintenance Dose Chart<br>(applicable only to pts receiving EPO-not pts on Hold) |
| Hgb is less than 10.5 g/dL AND Hgb decreasing over past 2 weeks | Increase dose using Maintenance Dose Chart |

TABLE A-6

Maintenance Dose Chart

| | | | | | Decrease 25% (Also use this column for Resume from Hold or Rapid Hgb Rise, using | |
|---|---|---|---|---|---|---|
| | Increase 25% | Increase 10% | Maintain | Decrease 10% | Last EPO Dose) | Hold |
| | | | | Latest Hemoglobin Value | | |
| Current Dose | HGB <10 | 10.0-10.4 | 10.5-10.8 | 10.9-11.5 | 11.6-11.9 | HGB >/=12 |
| 1,000 | 1,200 | 1,200 | 1,000 | 1000 at freq reduced per wk | 1000 at freq reduced by one per wk | Hold |
| 1,200 | 1,600 | 1,400 | 1,200 | 1,000 | 1000 at freq reduced by one per wk | Hold |
| 1,400 | 1,800 | 1,600 | 1,400 | 1,200 | 1,000 | Hold |
| 1,600 | 2,000 | 1,800 | 1,600 | 1,400 | 1,200 | Hold |
| 1,800 | 2,200 | 2,000 | 1,800 | 1,600 | 1,400 | Hold |
| 2,000 | 2,600 | 2,200 | 2,000 | 1,800 | 1,600 | Hold |
| 2,200 | 2,800 | 2,400 | 2,200 | 2,000 | 1,600 | Hold |
| 2,400 | 3,000 | 2,600 | 2,400 | 2,200 | 1,800 | Hold |
| 2,600 | 3,200 | 2,800 | 2,600 | 2,400 | 2,000 | Hold |
| 2,800 | 3,600 | 3,000 | 2,800 | 2,600 | 2,200 | Hold |
| 3,000 | 3,800 | 3,400 | 3,000 | 2,800 | 2,200 | Hold |
| 3,200 | 4,000 | 3,600 | 3,200 | 2,800 | 2,400 | Hold |
| 3,400 | 4,200 | 3,800 | 3,400 | 3,000 | 2,600 | Hold |
| 3,600 | 4,600 | 4,000 | 3,600 | 3,200 | 2,800 | Hold |
| 3,800 | 4,800 | 4,200 | 3,800 | 3,400 | 2,800 | Hold |

TABLE A-6-continued

Maintenance Dose Chart

| Current Dose | Increase 25%<br>HGB <10 | Increase 10%<br>10.0-10.4 | Maintain<br>10.5-10.8 | Decrease 10%<br>Latest Hemoglobin Value<br>10.9-11.5 | Decrease 25% (Also use this column for Resume from Hold or Rapid Hgb Rise, using Last EPO Dose)<br>11.6-11.9 | Hold<br>HGB >/=12 |
|---|---|---|---|---|---|---|
| 4,000 | 5,000 | 4,400 | 4,000 | 3,600 | 3,000 | Hold |
| 4,200 | 5,200 | 4,600 | 4,200 | 3,800 | 3,200 | Hold |
| 4,400 | 5,600 | 4,800 | 4,400 | 4,000 | 3,400 | Hold |
| 4,600 | 5,800 | 5,000 | 4,600 | 4,200 | 3,400 | Hold |
| 4,800 | 6,000 | 5,200 | 4,800 | 4,400 | 3,600 | Hold |
| 5,000 | 6,200 | 5,600 | 5,000 | 4,600 | 3,800 | Hold |
| 5,200 | 6,600 | 5,800 | 5,200 | 4,600 | 4,000 | Hold |
| 5,400 | 6,800 | 6,000 | 5,400 | 4,800 | 4,000 | Hold |
| 5,600 | 7,000 | 6,200 | 5,600 | 5,000 | 4,200 | Hold |
| 5,800 | 7,200 | 6,400 | 5,800 | 5,200 | 4,400 | Hold |
| 6,000 | 7,600 | 6,600 | 6,000 | 5,400 | 4,600 | Hold |
| 6,200 | 7,800 | 6,800 | 6,200 | 5,600 | 4,600 | Hold |
| 6,400 | 8,000 | 7,000 | 6,400 | 5,800 | 4,800 | Hold |
| 6,600 | 8,200 | 7,200 | 6,600 | 6,000 | 5,000 | Hold |
| 6,800 | 8,600 | 7,400 | 6,800 | 6,200 | 5,200 | Hold |
| 7,000 | 8,800 | 7,800 | 7,000 | 6,400 | 5,200 | Hold |
| 7,200 | 9,000 | 8,000 | 7,200 | 6,400 | 5,400 | Hold |
| 7,400 | 9,200 | 8,200 | 7,400 | 6,600 | 5,600 | Hold |
| 7,600 | 9,600 | 8,400 | 7,600 | 6,800 | 5,800 | Hold |
| 7,800 | 9,800 | 8,600 | 7,800 | 7,000 | 5,800 | Hold |
| 8,000 | 10,000 | 8,800 | 8,000 | 7,200 | 6,000 | Hold |
| 8,200 | 10,000 | 9,000 | 8,200 | 7,400 | 6,200 | Hold |
| 8,400 | 11,000 | 9,200 | 8,400 | 7,600 | 6,400 | Hold |
| 8,600 | 11,000 | 9,400 | 8,600 | 7,800 | 6,400 | Hold |
| 8,800 | 11,000 | 9,600 | 8,800 | 8,000 | 6,600 | Hold |
| 9,000 | 11,000 | 10,000 | 9,000 | 8,200 | 6,800 | Hold |
| 9,200 | 12,000 | 10,000 | 9,200 | 8,200 | 7,000 | Hold |
| 9,400 | 12,000 | 10,000 | 9,400 | 8,400 | 7,000 | Hold |
| 9,600 | 12,000 | 11,000 | 9,600 | 8,600 | 7,200 | Hold |
| 9,800 | 12,000 | 11,000 | 9,800 | 8,800 | 7,400 | Hold |
| 10,000 | 13,000 | 11,000 | 10,000 | 9,000 | 7,600 | Hold |
| 11,000 | 14,000 | 12,000 | 11,000 | 10,000 | 8,200 | Hold |
| 12,000 | 15,000 | 13,000 | 12,000 | 11,000 | 9,000 | Hold |
| 13,000 | 16,000 | 14,000 | 13,000 | 12,000 | 9,800 | Hold |
| 14,000 | 18,000 | 15,000 | 14,000 | 13,000 | 11,000 | Hold |
| 15,000 | 19,000 | 17,000 | 15,000 | 14,000 | 11,000 | Hold |
| 16,000 | 20,000 | 18,000 | 16,000 | 14,000 | 12,000 | Hold |
| 17,000 | 21,000 | 19,000 | 17,000 | 15,000 | 13,000 | Hold |
| 18,000 | 23,000 | 20,000 | 18,000 | 16,000 | 14,000 | Hold |
| 19,000 | 24,000 | 21,000 | 19,000 | 17,000 | 14,000 | Hold |
| 20,000 | 25,000 | 22,000 | 20,000 | 18,000 | 15,000 | Hold |
| 21,000 | 26,000 | 23,000 | 21,000 | 19,000 | 16,000 | Hold |
| 22,000 | 28,000 | 24,000 | 22,000 | 20,000 | 17,000 | Hold |
| 23,000 | 28,000 | 25,000 | 23,000 | 21,000 | 17,000 | Hold |
| 24,000 | 28,000 | 26,000 | 24,000 | 22,000 | 18,000 | Hold |
| 25,000 | 28,000 | 28,000 | 25,000 | 23,000 | 19,000 | Hold |
| 26,000 | 28,000 | 28,000 | 26,000 | 23,000 | 20,000 | Hold |
| 27,000 | 28,000 | 28,000 | 27,000 | 24,000 | 20,000 | Hold |
| 28,000 | 28,000 | 28,000 | 28,000 | 25,000 | 21,000 | Hold |

TABLE A-7

Starting Dose Chart (Starting Dose versus Body Weight)

| Weight (kg) | Starting Dose (U) Based on 100 U/kg 3x/Week, or equivalent | | | Weight (kg) | Starting Dose (U) Based on 100 U/kg 3x/Week, or equivalent | | | Weight (kg) | Starting Dose (U) Based on 100 U/kg 3x/Week, or equivalent (maximum of 28,000 units/administration) | | |
|---|---|---|---|---|---|---|---|---|---|---|---|
| | Dose if 3x/Week | Dose if 2x/Week | Dose if 1x/Week | | Dose if 3x/Week | Dose if 2x/Week | Dose if 1x/Week | | Dose if 3x/Week | Dose if 2x/Week | Dose if 1x/Week |
| 25 | 3,000 | 4,000 | 8,000 | 50 | 5,000 | 8,000 | 15,000 | 75 | 8,000 | 11,000 | 23,000 |
| 26 | 3,000 | 4,000 | 8,000 | 51 | 5,000 | 8,000 | 15,000 | 76 | 8,000 | 11,000 | 23,000 |

TABLE A-7-continued

Starting Dose Chart (Starting Dose versus Body Weight)

| Weight (kg) | Starting Dose (U) Based on 100 U/kg 3x/Week, or equivalent | | | Weight (kg) | Starting Dose (U) Based on 100 U/kg 3x/Week, or equivalent | | | Weight (kg) | Starting Dose (U) Based on 100 U/kg 3x/Week, or equivalent (maximum of 28,000 units/administration) | | |
|---|---|---|---|---|---|---|---|---|---|---|---|
| | Dose if 3x/Week | Dose if 2x/Week | Dose if 1x/Week | | Dose if 3x/Week | Dose if 2x/Week | Dose if 1x/Week | | Dose if 3x/Week | Dose if 2x/Week | Dose if 1x/Week |
| 27 | 3,000 | 4,000 | 8,000 | 52 | 5,000 | 8,000 | 16,000 | 77 | 8,000 | 12,000 | 23,000 |
| 30 | 3,000 | 5,000 | 9,000 | 55 | 6,000 | 8,000 | 17,000 | 80 | 8,000 | 12,000 | 24,000 |
| 31 | 3,000 | 5,000 | 9,000 | 56 | 6,000 | 8,000 | 17,000 | 81 | 8,000 | 12,000 | 24,000 |
| 32 | 3,000 | 5,000 | 10,000 | 57 | 6,000 | 9,000 | 17,000 | 82 | 8,000 | 12,000 | 25,000 |
| 35 | 4,000 | 5,000 | 11,000 | 60 | 6,000 | 9,000 | 18,000 | 85 | 9,000 | 13,000 | 26,000 |
| 36 | 4,000 | 5,000 | 11,000 | 61 | 6,000 | 9,000 | 18,000 | 86 | 9,000 | 13,000 | 26,000 |
| 37 | 4,000 | 6,000 | 11,000 | 62 | 6,000 | 9,000 | 19,000 | 87 | 9,000 | 13,000 | 26,000 |
| 40 | 4,000 | 6,000 | 12,000 | 65 | 7,000 | 10,000 | 20,000 | 90 | 9,000 | 14,000 | 27,000 |
| 41 | 4,000 | 6,000 | 12,000 | 66 | 7,000 | 10,000 | 20,000 | 91 | 9,000 | 14,000 | 27,000 |
| 42 | 4,000 | 6,000 | 13,000 | 67 | 7,000 | 10,000 | 20,000 | 92 | 9,000 | 14,000 | 28,000 |
| 45 | 5,000 | 7,000 | 14,000 | 70 | 7,000 | 11,000 | 21,000 | 95 | 10,000 | 14,000 | 28,000 |
| 46 | 5,000 | 7,000 | 14,000 | 71 | 7,000 | 11,000 | 21,000 | 96 | 10,000 | 14,000 | 28,000 |
| 47 | 5,000 | 7,000 | 14,000 | 72 | 7,000 | 11,000 | 22,000 | 97 | 10,000 | 15,000 | 28,000 |
| 50 | 5,000 | 8,000 | 15,000 | 75 | 8,000 | 11,000 | 23,000 | >=10 | 10,000 | 15,000 | 28,000 |

TABLE A-8

Maximum Dose Chart (Maximum Dose versus Body Weight)

| Weight (kg) | Maximum Dose (U) Based on 300 U/kg 3x/Week, or equivalent | | | Weight (kg) | Maximum Dose (U) Based on 300 U/kg 3x/Week, or equivalent | | | Weight (kg) | Maximum Dose (U) Based on 300 U/kg 3x/Week, or equivalent | | |
|---|---|---|---|---|---|---|---|---|---|---|---|
| | Dose if 3x/Week | Dose if 2x/Week | Dose if 1x/Week | | Dose if 3x/Week | Dose if 2x/Week | Dose if 1x/Week | | Dose if 3x/Week | Dose if 2x/Week | Dose if 1x/Week |
| 25 | 8,000 | 11,000 | 23,000 | 50 | 15,000 | 23,000 | 45,000 | 75 | 23,000 | 34,000 | 68,000 |
| 26 | 8,000 | 12,000 | 23,000 | 51 | 15,000 | 23,000 | 46,000 | 76 | 23,000 | 34,000 | 68,000 |
| 27 | 8,000 | 12,000 | 24,000 | 52 | 16,000 | 23,000 | 47,000 | 77 | 23,000 | 35,000 | 69,000 |
| 30 | 9,000 | 14,000 | 27,000 | 55 | 17,000 | 25,000 | 50,000 | 80 | 24,000 | 36,000 | 72,000 |
| 31 | 9,000 | 14,000 | 28,000 | 56 | 17,000 | 25,000 | 50,000 | 81 | 24,000 | 36,000 | 73,000 |
| 32 | 10,000 | 14,000 | 29,000 | 57 | 17,000 | 26,000 | 51,000 | 82 | 25,000 | 37,000 | 74,000 |
| 35 | 11,000 | 16,000 | 32,000 | 60 | 18,000 | 27,000 | 54,000 | 85 | 26,000 | 38,000 | 77,000 |
| 36 | 11,000 | 16,000 | 32,000 | 61 | 18,000 | 27,000 | 55,000 | 86 | 26,000 | 39,000 | 77,000 |
| 37 | 11,000 | 17,000 | 33,000 | 62 | 19,000 | 28,000 | 56,000 | 87 | 26,000 | 39,000 | 78,000 |
| 40 | 12,000 | 18,000 | 36,000 | 65 | 20,000 | 29,000 | 59,000 | 90 | 27,000 | 40,000 | 80,000 |
| 41 | 12,000 | 18,000 | 37,000 | 66 | 20,000 | 30,000 | 59,000 | 91 | 27,000 | 40,000 | 80,000 |
| 42 | 13,000 | 19,000 | 38,000 | 67 | 20,000 | 30,000 | 60,000 | 92 | 28,000 | 40,000 | 80,000 |
| 45 | 14,000 | 20,000 | 41,000 | 70 | 21,000 | 32,000 | 63,000 | 95 | 28,000 | 40,000 | 80,000 |
| 46 | 14,000 | 21,000 | 41,000 | 71 | 21,000 | 32,000 | 64,000 | 96 | 28,000 | 40,000 | 80,000 |
| 47 | 14,000 | 21,000 | 42,000 | 72 | 22,000 | 32,000 | 65,000 | 97 | 28,000 | 40,000 | 80,000 |
| 50 | 15,000 | 23,000 | 45,000 | 75 | 23,000 | 34,000 | 68,000 | >=10 | 28,000 | 40,000 | 80,000 |

The relevant teachings of all patents, published patent applications and literature references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of adjusting a patient's undesired hematocrit and/or hemoglobin concentration to a value within a desired range at a predetermined time with an erythropoiesis stimulating agent (ESA) regimen comprising:
   a) obtaining patient parameters required for input into a model for predicting the patient's hematocrit and/or hemoglobin concentration at a predetermined time with a selected ESA administration regimen;
   b) employing the patient parameters and an initially selected ESA administration regimen in the model to predict the patient's hematocrit and/or hemoglobin concentration at the predetermined time with the initially selected ESA administration regimen, wherein the model comprises the functions:

$$\frac{\partial}{\partial t} p(t, \mu^p) + \frac{\partial}{\partial \mu^p} p(t, \mu^p) = \beta^p p(t, \mu^p),$$

$$\frac{\partial}{\partial t} q(t, \mu^q) + \frac{\partial}{\partial \mu^q} q(t, \mu^q) = (\beta^q - \alpha^q(E(t))) q(t, \mu^q),$$

-continued $$\frac{\partial}{\partial t}r(t, \mu^r) + \frac{\partial}{\partial \mu^r}r(t, \mu^r) = \beta^r r(t, \mu^r),$$

$$\frac{\partial}{\partial t}s(t, \mu^s) + v^s(E(t))\frac{\partial}{\partial \mu^s}s(t, \mu^s) = -\alpha^s s(t, \mu^s),$$

$$\frac{\partial}{\partial t}m(t, \mu^m) + \frac{\partial}{\partial \mu^m}m(t, \mu^m) = -\alpha^m(E(t), \mu^m)m(t, \mu^m),$$

and $$\frac{d}{dt}E^{end}(t) = \frac{1}{TBV}E_{in}^{end}(t) - c_{deg}^{end}E^{end}(t)$$

$$\frac{d}{dt}E^{ex}(t) = \frac{1}{TBV}E_{in}^{ex}(t) - c_{deg}^{ex}E^{ex}(t),$$

where $$\alpha^q(E(t)) = \frac{a_1 - b_1}{1 + e^{k_1 E(t) - c_1}} + b_1$$

$$\alpha^q(E(t)) = \frac{a_1 - b_1}{1 + e^{-k_1 E(t) - c_1}} + b_1,$$

$$\alpha^m(E(t), \mu^m) = \begin{cases} \gamma^m + \min\left(\frac{c_E}{E(t)^{k_E}}, b_E\right) & \text{for } E(t) < \tau_E, \mu_{min}^{m,n} \leq \mu^m \leq \mu_{max}^{m,n}, \\ \gamma^m & \text{otherwise,} \end{cases}$$

where $$\tilde{M}(t) = 10^{-8}M(t)/TBV,$$

$$M(t) = \int_0^{\mu_{max}^m} m(t, \mu^m)d\mu^m, \text{ and}$$

$$TBV = \text{total blood volume},$$

wherein $p(t,\mu^p)$ is a population density of a BFU-E cell class at time t with maturity $\mu^p$, $\beta^p$ is a proliferation rate for BFU-E cells, $q(t,\mu^q)$ is a population density of a CFU-E cell class at time t with maturity $\mu^q$, $\beta^q$ is a proliferation rate for CFU-E cells, $\alpha^q(E(t))$ is an apoptosis rate for CFU-E cells which depends on erythropoietin(EPO)-concentration E(t) at time t, $r(t, \mu^r)$ is a population density of an erythroblast class at time t with maturity $\mu^r$, $\beta^r$ is a proliferation rate for erythroblasts, $s(t,\mu^s)$ is a population density of a marrow reticulocytes class at time t with maturity $\mu^s$, $v^s(E(t))$ is a maturation velocity of cells leaving the erythroblast class an entering the reticulocytes population class which depends on EPO-concentration E(t) at time t, $\alpha^s$ is an apoptosis rate for marrow reticulocytes, $m(t, \mu^m)$ is a population density of an erythrocyte class at time t with maturity $\mu^m$, $\alpha^m(E(t), \mu^m)$ is an apoptosis rate for erythrocytes which depends on EPO-concentration E(t) at time t and maturity $\mu^m$, $E^{end}(t)$ is an endogenous EPO concentration at time t, $E_{in}^{end}(t)$ is an amount of EPO released by a patient's kidneys, $c_{deg}^{end}$ is a degradation rate of endogenous EPO, $E^{ex}(t)$ is an exogenous EPO concentration at time t, $E_{in}^{ex}(t)$ is an amount of EPO administered to the patient, $c_{deg}^{ex}$ is a degradation rate of exogenous EPO, $a_1$, $b_1$, $c_1$ and $k_1$ are constants for the apoptosis rate for CFU-E cells, $a_2$, $b_2$, $c_2$, and $k_2$ are constants for the maturation velocity for marrow reticulocytes, $\gamma^m$ is a mortality rate of erythrocytes, $b_E$, $c_E$, and $k_E$ are constants in the mortality rate of erythrocytes, $\tau_E$ is a threshold beneath which neocytolysis is triggered, $\mu^m$ is a erythrocyte maturity; $\mu_{min}^{m,n}$ is a lower bound of erythrocytes which are possibly exposed to neocytolysis, $\mu_{max}^{m,n}$ is an upper bound of erythrocytes which are possibly exposed to neocytolysis, M(t) is a total population of erythrocytes;

c) employing the model with one or more different ESA administration regimens until the model predicts that the patient's hematocrit and/or hemoglobin concentration will be in the desired range at the predetermined time; and d) administering ESA to the patient according to the different ESA administration regimen predicted to adjust the patient's hematocrit and/or hemoglobin concentration to a value within the desired range at the predetermined time.

2. The method of claim 1, wherein the patient parameters include starting hematocrit and/or hemoglobin concentration in the patient's blood, total blood volume of the patient, lifespan of red blood cells (RBCs) of the patient, mean corpuscular volume of the RBCs, and rate of neocytolysis in the patient's blood.

3. The method of claim 1, wherein the predetermined time is in a range of between about 5 days and about 200 days into the ESA administration regimen.

4. The method of claim 1, wherein the patient is a dialysis patient and the desired hematocrit is in the range of between about 28 percent and about 36 percent and the desired hemoglobin concentration is in a range of between about 9.5 g/dL and about 12 g/dL.

5. A system for adjusting a patient's undesired hematocrit and/or hemoglobin concentration to a value within a desired range at a predetermined time with an erythropoiesis stimulating agent (ESA) regimen the system comprising:

a) an input means for determining patient parameters of the patient;

b) a digital processor coupled to receive determined patient data from the input means, wherein the digital processor executes a modeling system in working memory, wherein the modeling system is configured to:
  i) employ the patient parameters and an initially selected ESA administration regimen in the model to predict the patient's hematocrit and/or hemoglobin concentration at the predetermined time with the initially selected ESA administration regimen, wherein the model comprises the functions:

$$\frac{\partial}{\partial t}p(t, \mu^p) + \frac{\partial}{\partial \mu^p}p(t, \mu^p) = \beta^p p(t, \mu^p),$$

$$\frac{\partial}{\partial t}q(t, \mu^q) + \frac{\partial}{\partial \mu^q}q(t, \mu^q) = (\beta^q - \alpha^q(E(t)))q(t, \mu^q),$$

$$\frac{\partial}{\partial t}r(t, \mu^r) + \frac{\partial}{\partial \mu^r}r(t, \mu^r) = \beta^r r(t, \mu^r),$$

$$\frac{\partial}{\partial t}s(t, \mu^s) + v^s(E(t))\frac{\partial}{\partial \mu^s}s(t, \mu^s) = -\alpha^s s(t, \mu^s),$$

$$\frac{\partial}{\partial t}m(t, \mu^m) + \frac{\partial}{\partial \mu^m}m(t, \mu^m) = -\alpha^m(E(t), \mu^m)m(t, \mu^m),$$

and $$\frac{d}{dt}E^{end}(t) = \frac{1}{TBV}E_{in}^{end}(t) - c_{deg}^{end}E^{end}(t)$$

$$\frac{d}{dt}E^{ex}(t) = \frac{1}{TBV}E_{in}^{ex}(t) - c_{deg}^{ex}E^{ex}(t),$$

where $$\alpha^q(E(t)) = \frac{a_1 - b_1}{1 + e^{k_1 E(t) - c_1}} + b_1$$

-continued $$v^s(E(t)) = \frac{a_2 - b_2}{1 + e^{-k_2 E(t) + c_2}} + b_2,$$

$$\alpha^m(E(t), \mu^m) = \begin{cases} \gamma^m + \min\left(\frac{c_E}{E(t)^{k_E}}, b_E\right) & \text{for } E(t) < \tau_E, \mu_{min}^{m,n} \leq \mu^m \leq \mu_{max}^{m,n}, \\ \gamma^m & \text{otherwise,} \end{cases}$$

where $$\tilde{M}(t) = 10^{-8} M(t)/TBV,$$

$$M(t) = \int_0^{\mu_{max}^m} m(t, \mu^m) d\mu^m, \text{ and}$$

$TBV$ = total blood volume, wherein $p(t,\mu^p)$ is a population density of a BFU-E cell class at time t with maturity $\mu^p$, $\beta^p$ is a proliferation rate for BFU-E cells, $q(t,\mu^q)$ is a population density of a CFU-E cell class at time t with maturity $\mu^q$, $\beta^q$ is a proliferation rate for CFU-E cells, $\alpha^q(E(t))$ is an apoptosis rate for CFU-E cells which depends on erythropoietin (EPO)-concentration E(t) at time t, $r(t,\mu^r)$ is a population density of an erythroblast class at time t with maturity $\mu^r$, $\beta^r$ is a proliferation rate for erythroblasts, $s(t,\mu^s)$ is a population density of a marrow reticulocytes class at time t with maturity $\mu^s$, $v^s(E(t))$ is a maturation velocity of cells leaving the erythroblast class an entering the reticulocytes population class which depends on EPO-concentration E(t) at time t, $\alpha^s$ is an apoptosis rate for marrow reticulocytes, $m(t, \mu^m)$ is a population density of an erythrocyte class at time t with maturity $\mu^m$, $\alpha^m(E(t), \mu^m)$ is an apoptosis rate for erythrocytes which depends on EPO concentration E(t) at time t and maturity $\mu^m$, $E^{end}(t)$ is an endogenous EPO concentration at time t, $E_{in}^{end}(t)$ is an amount of EPO released by a patient's kidneys, $c_{deg}^{end}$ is a degradation rate of endogenous EPO, $E^{ex}(t)$ is an exogenous EPO concentration at time t, $E_{in}^{ex}(t)$ is an amount of EPO administered to the patient, $c_{deg}^{ex}$ is a degradation rate of exogenous EPO, $a_1$, $b_1$, $c_1$ and $k_1$ are constants for the apoptosis rate for CFU-E cells, $a_2$, $b_2$, $c_2$, and $k_2$ are constants for the maturation velocity for marrow reticulocytes, $\gamma^m$ is a mortality rate of erythrocytes, $b_E$, $c_E$, and $k_E$ are constants in the mortality rate of erythrocytes, $\tau_E$ is a threshold beneath which neocytolysis is triggered, $\mu^m$ is a erythrocyte maturity; $\mu_{min}^{m,n}$ is a lower bound of erythrocytes which are possibly exposed to neocytolysis, $\mu_{max}^{m,n}$ is an upper bound of erythrocytes which are possibly exposed to neocytolysis, M(t) is a total population of erythrocytes; and ii) employ the model with one or more different ESA administration regimens until the model predicts that the patient's hematocrit and/or hemoglobin concentration will be a value within in the desired range at the predetermined time; and c) a dialysis machine coupled to the digital processor, wherein the digital processor is further configured to control administration of the ESA according to an ESA administration regimen that adjusts the patient's hematocrit and/or hemoglobin concentration to a value that is within the desired range at the predetermined time.

6. The system of claim 5, wherein the patient parameters include starting hemoglobin concentration in the patient's blood, total blood volume of the patient, lifespan of red blood cells (RBCs) of the patient, mean corpuscular volume of the RBCs, and rate of neocytolysis in the patient's blood.

7. The system of claim 5, wherein the predetermined time is in a range of between about 5 days and about 200 days into the ESA administration regimen.

8. The system of claim 5, wherein the patient is a dialysis patient and the desired hematocrit is in the range of between about 28 percent and about 36 percent and the desired hemoglobin concentration is in a range of between about 9.5 g/dL and about 12 g/d L.

9. A method of determining an erythropoiesis stimulating agent (ESA) administration regimen to bring a patient's hematocrit and/or hemoglobin concentration into a desired range at a predetermined time comprising:

a) obtaining patient parameters required for input into a model for predicting the patient's hematocrit and/or hemoglobin concentration at a predetermined time with a selected ESA administration regimen;

b) employing the patient parameters and an initially selected ESA administration regimen in the model to predict the patient's hematocrit and/or hemoglobin concentration at the predetermined time with the initially selected ESA administration regimen, wherein the model comprises the functions:

$$\frac{\partial}{\partial t} p(t, \mu^p) + \frac{\partial}{\partial \mu^p} p(t, \mu^p) = \beta^p p(t, \mu^p),$$

$$\frac{\partial}{\partial t} q(t, \mu^q) + \frac{\partial}{\partial \mu^q} q(t, \mu^q) = (\beta^q - \alpha^q(E(t))) q(t, \mu^q),$$

$$\frac{\partial}{\partial t} r(t, \mu^r) + \frac{\partial}{\partial \mu^r} (t, \mu^r) = \beta^r r(t, \mu^r),$$

$$\frac{\partial}{\partial t} s(t, \mu^s) + v^s(E(t)) \frac{\partial}{\partial \mu^s} s(t, \mu^s) = -\alpha^s s(t, \mu^s),$$

$$\frac{\partial}{\partial t} m(t, \mu^m) + \frac{\partial}{\partial \mu^m} m(t, \mu^m) = -\alpha^m(E(t), \mu^m) m(t, \mu^m), \text{ and}$$

$$\frac{d}{dt} E^{end}(t) = \frac{1}{TBV} E_{in}^{end}(t) - c_{deg}^{end} E^{end}(t)$$

$$\frac{d}{dt} E^{ex}(t) = \frac{1}{TBV} E_{in}^{ex}(t) - c_{deg}^{ex} E^{ex}(t), \text{ where}$$

$$\alpha^q(E(t)) = \frac{a_1 - b_1}{1 + e^{k_1 E(t) - c_1}} + b_1$$

$$\alpha^q(E(t)) = \frac{a_1 - b_1}{1 + e^{k_1 E(t) - c_1}} + b_1$$

$$\alpha^m(E(t), \mu^m) = \begin{cases} \gamma^m + \min\left(\frac{c_E}{E(t)^{k_E}}, b_E\right) & \text{for } E(t) < \tau_E, \mu_{min}^{m,n} \leq \mu^m \leq \mu_{max}^{m,n}, \\ \gamma^m & \text{otherwise} \end{cases},$$

where $$\tilde{M}(t) = 10^{-8} M(t)/TBV,$$

$$M(t) = \int_0^{\mu_{max}^m} m(t, \mu^m) d\mu^m, \text{ and}$$

$TBV$ = total blood volume, wherein $p(t,\mu^p)$ is a population density of a BFU-E cell class at time t with maturity $\mu^p$, $\beta^p$ is a proliferation rate for BFU-E cells, $q(t,\mu^q)$ is a population density of a CFU-E cell class at time t with maturity $\mu^q$, $\beta^q$ is a proliferation rate for CFU-E cells, $\alpha^q(E(t))$ is an apoptosis rate for CFU-E cells which depends on erythropoietin(EPO)-concentration E(t) at time t, r(t, $\mu^r$) is a population density of an erythroblast class at time t with maturity $\mu^r$, $\beta^r$ is a proliferation rate for erythroblasts, $s(t,\mu^s)$ is a population density of a marrow reticulocytes class at time t with maturity $\mu^s$, $v^s(E(t))$ is a maturation velocity of cells leaving the erythroblast class an entering the reticulocytes population class which depends on EPO-concentration E(t) at time t, $\alpha^s$ is an apoptosis rate for marrow reticulocytes, $m(t, \mu^m)$ is a population density of an erythrocyte class at time t with maturity $\mu^m$, $\alpha^m(E(t), \mu^m)$ is an apoptosis rate for erythrocytes which depends on EPO-concentration E(t) at time t and maturity $\mu^m$, $E^{end}(t)$ is an endogenous EPO concentration at time t, $E_{in}^{end}(t)$ is an amount of EPO released by a patient's kidneys, $c_{deg}^{end}$ is a degradation rate of endogenous EPO, $E^{ex}(t)$ is an exogenous EPO concentration at time t, $E_{in}^{ex}(t)$ is an amount of EPO administered to the patient, $c_{deg}^{ex}$ is a degradation rate of exogenous EPO, $a_1$, $b_1$, $c_1$ and $k_1$ are constants for the apoptosis rate for CFU-E cells, $a_2$, $b_2$, $c_2$, and $k_2$ are constants for the maturation velocity for marrow reticulocytes, $\gamma^m$ is a mortality rate of erythrocytes, $b_E$, $c_E$, and $k_E$ are constants in the mortality rate of erythrocytes, $\tau_E$ is a threshold beneath which neocytolysis is triggered, $\mu^m$ is a erythrocyte maturity; $\mu hd min^{m,n}$ is a lower bound of erythrocytes which are possibly exposed to neocytolysis, $\mu_{max}^{m,n}$ is an upper bound of erythrocytes which are possibly exposed to neocytolysis, M(t) is a total population of erythrocytes; and c) employing the model with one or more different ESA administration regimens until the model predicts that the patient's hematocrit and/or hemoglobin concentration will be in the desired range at the predetermined time; and d) administering ESA to the patient according to the different ESA administration regimen predicted to adjust the patient's hematocrit and/or hemoglobin concentration to a value within the desired range at the predetermined time.

10. The method of claim 1, wherein the patient undergoes a medical procedure prior to, during, or after initiation of the ESA administration regimen, the medical procedure selected from the group consisting of blood donation, surgery, and dialysis, or any combination thereof.

* * * * *

UNITED STATES PATENT AND TRADEMARK OFFICE
CERTIFICATE OF CORRECTION

PATENT NO. : 10,319,478 B2
APPLICATION NO. : 14/343464
DATED : June 11, 2019
INVENTOR(S) : Doris Helene Fuertinger et al.

It is certified that error appears in the above-identified patent and that said Letters Patent is hereby corrected as shown below:

In the Claims

In Claim 1, Column 45, Line 18, delete:
"$\alpha^q(E(t)) = \frac{a_1 - b_1}{1 + e^{-k_1 E(t) - c_1}} + b_1$,"
And insert:
-- $v^s(E(t)) = \frac{a_2 - b_2}{1 + e^{-k_2 E(t) + c_2}} + b_2$, --.

In Claim 9, Column 48, Line 46, delete:
"$\alpha^q(E(t)) = \frac{a_1 - b_1}{1 + e^{k_1 E(t) - c_1}} + b_1$"
And insert:
-- $\alpha^q(E(t)) = \frac{a_1 - b_1}{1 + e^{k_1 E(t) - c_1}} + b_1$, --.

In Claim 9, Column 48, Line 48, delete:
"$\alpha^q(E(t)) = \frac{a_1 - b_1}{1 + e^{k_1 E(t) - c_1}} + b_1$,"
And insert:
-- $v^s(E(t)) = \frac{a_2 - b_2}{1 + e^{-k_2 E(t) + c_2}} + b_2$, --.

Signed and Sealed this
Nineteenth Day of November, 2019

Andrei Iancu
*Director of the United States Patent and Trademark Office*